(12) United States Patent
Tyler et al.

(10) Patent No.: US 11,518,779 B2
(45) Date of Patent: Dec. 6, 2022

(54) INHIBITORS OF DNMT1 AS ANTICANCER THERAPEUTIC AGENTS

(71) Applicants: Victoria Link Limited, Wellington (NZ); Albert Einstein College of Medicine, Bronx, NY (US); Timothy Dravitzki, Porirua (NZ)

(72) Inventors: Peter Charles Tyler, Wellington (NZ); Farah Lamiable-Oulaidi, Lower Hutt (NZ); Anthony David Woolhouse, Porirua (NZ); Shivali Ashwin Gulab, New York, NY (US); Karl Jürgen Shaffer, Lower Hutt (NZ); Ashna Ashneen Khan, Auckland (NZ); Douglas Ronald Crump, Wellington (NZ); Vern L. Schramm, New Rochelle, NY (US); Quan Du, San Diego, CA (US)

(73) Assignees: Victoria Link Limited, Wellington (NZ); Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 17/250,330

(22) PCT Filed: Jul. 9, 2019

(86) PCT No.: PCT/NZ2019/050080
§ 371 (c)(1),
(2) Date: Jan. 6, 2021

(87) PCT Pub. No.: WO2020/013712
PCT Pub. Date: Jan. 16, 2020

(65) Prior Publication Data
US 2021/0206795 A1    Jul. 8, 2021

Related U.S. Application Data

(60) Provisional application No. 62/695,281, filed on Jul. 9, 2018.

(51) Int. Cl.
*C07H 19/16*    (2006.01)

(52) U.S. Cl.
CPC .................................. *C07H 19/16* (2013.01)

(58) Field of Classification Search
CPC ...................................................... C07H 19/16
See application file for complete search history.

(56) References Cited

U.S. PATENT DOCUMENTS

| 8,822,146 B2* | 9/2014 | Klimasauskas ...... C12Q 1/6827 435/6.1 |
| 8,889,352 B2* | 11/2014 | Klimasauskas ........ C07H 21/00 435/6.1 |
| 9,505,797 B2* | 11/2016 | Klimasauskas .......... C12Q 1/48 |

FOREIGN PATENT DOCUMENTS

| WO | 2006/078752 A2 | 7/2006 |
| WO | 2010/115846 A1 | 10/2010 |
| WO | 2017/211958 A1 | 12/2017 |

* cited by examiner

*Primary Examiner* — Layla D Berry
(74) *Attorney, Agent, or Firm* — Fox Rothschild LLP

(57) ABSTRACT

Provided herein are inhibitors of DNA methyltransferase 1 (an enzyme responsible for the maintenance of DNA CpG methylation marks in human cells) and their use for inhibiting DNA methyltransferase 1. The invention relates to compounds, pharmaceutical compositions, and methods for inhibiting DNA methyltransferase 1. The inhibitors are compounds of the general formula:

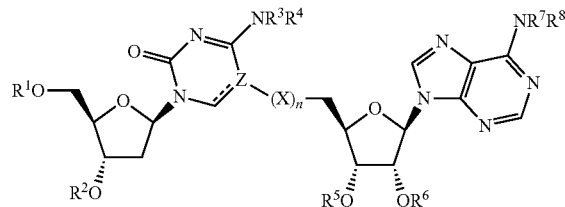

16 Claims, 1 Drawing Sheet

Specification includes a Sequence Listing.

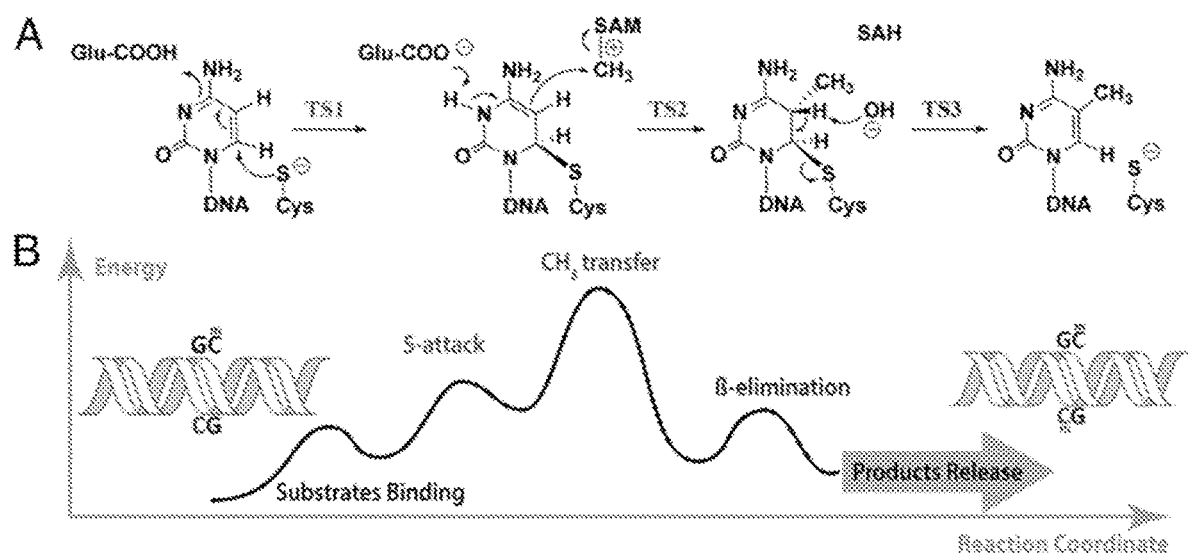

SEQUENCE LISTING

```
<160> NUMBER OF SEQ ID NOS: 2

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide - synthesised in
      laboratory

<400> SEQUENCE: 1
ctaccttggt atcgattggt atgagt                                              26

<210> SEQ ID NO 2
<211> LENGTH: 26
<212> TYPE: DNA
<213> ORGANISM: Artificial
<220> FEATURE:
<223> OTHER INFORMATION: Synthetic oligonucleotide - synthesised in
      laboratory
<220> FEATURE:
<221> NAME/KEY: modified_base
<222> LOCATION: (13)..(13)
<223> OTHER INFORMATION: m5c - (i.e., 5-methyl-C base)

<400> SEQUENCE: 2
actcatacca atcgatacca aggtag                                              26
```

INHIBITORS OF DNMT1 AS ANTICANCER THERAPEUTIC AGENTS

CROSS-REFERENCE TO RELATED APPLICATIONS

The present application is a National Stage Application under 35 U.S.C. § 371 of International Application No. PCT/NZ19/50080 filed Jul. 9, 2019, which claims the benefit of priority to U.S. Provisional Patent Application Ser. No. 62/695,281 filed Jul. 9, 2018, the disclosures of all of which are hereby incorporated in their entireties.

TECHNICAL FIELD

This invention relates generally to novel compounds and their use as anticancer therapeutic agents. In particular, the invention relates to certain compounds that are inhibitors of DNA methyltransferase 1 and are therefore potential therapeutic agents against various cancers.

BACKGROUND OF THE INVENTION

Cytosines in CpG dinucleotides can be methylated to form 5-methylcytosine. This methylation of cytosines at CpG sites in the gene of a mammal can alter the expression of the gene. Enzymes that catalyse the addition of a methyl group to a cytosine are known as DNA methyltransferases (DNMTs). DNA methylation is involved in transcriptional silencing, cellular differentiation, genomic imprinting, and X-chromosome inactivation. In addition, hypermethylation of CpG islands at gene promoter regions has been associated with carcinogenesis.

DNA methyltransferase 1 (DNMT1) is the major enzyme responsible for the maintenance of DNA CpG methylation marks in human cells. The enzyme is a validated target for cancer.

Enzymes catalyse reactions by forming short-lived transition states from their reactants. Transition state analysis based on experimental kinetic isotope effects has provided detailed insights into the catalytic mechanisms of enzymes acting mostly on small molecules and has led to the design of powerful enzyme inhibitors. The transition state of human DNMT1 has recently been published (Du, Q., Wang, Z., Schramm, V. L., Proc. Natl. Acad. Sci. USA, 113, 2916-2921, 2016).

Although inhibitors of human DNMT have been used in cancer therapy, because elevated CpG methylation in tumour repressors can result in carcinogenesis, all DNMT inhibitors currently approved by the US Food and Drug Administration are cytotoxic and mutagenic. These inhibitors (e.g. 5-aza-cytidine and 5-aza-2'-deoxycytidine—Decitabine) inhibit DNA methylation by being incorporated into host DNA. They inhibit DNMTs by forming covalent adducts with them. Further DNMT inhibitors have been identified from chemical library screening, but they often lack specificity against DNMTs. Accordingly, there is an ongoing need to find improved DNMT inhibitors.

PCT patent application PCT/EP2017/063978 (published as WO 2017/211958) describes compounds similar in chemical structure to the compounds of the present invention. However, these compounds act on different target substrates. The compounds are said to be inhibitors of protein arginine N-methyltransferase (PRMT) in the treatment of cancer. The structure of these compounds has a cytosine part and an adenosine part. They do not possess a deoxyribose moiety which is considered to be an important structural feature of the compounds of the present invention for activity against DNMTs.

A series of related PCT patent applications (PCT/US2012/062157, WO 2013/063417; PCT/US2014/034118, WO 2014/172330; PCT/US2016/058100, WO 2017/070464; PCT/US2017/051858, WO 2018/053313) describe compounds that are active against protein methyl transferases. Inhibitors of protein methyl transferases would not be expected to be active against DNMTs due to different steric and electronic interactions within the active sites of the enzymes. The compounds described in these patent applications do not possess a deoxycytidine moiety which is considered essential for activity of DNMT1 inhibitors.

The applicants have now found that certain compounds having deoxycytidine and adenosine moieties are effective inhibitors of DNMT1. It is therefore an object of the invention to provide a novel inhibitor of DNMT1, or to at least provide a useful choice.

SUMMARY OF THE INVENTION

In a first aspect of the invention there is provided a compound of formula (I):

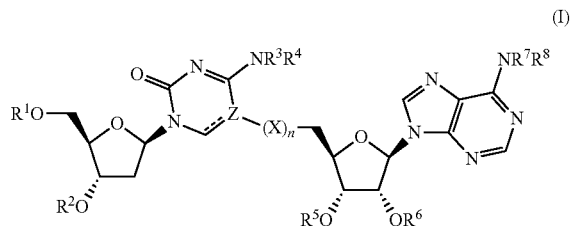

(I)

wherein:

each X is independently selected from the group comprising $CH_2$, CHY, NH, NY, and S, provided that no more than one X is CHY or NY, where Y is:

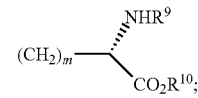

$R^1$ to $R^{10}$ are each independently selected from the group comprising H, $C_1$-$C_3$ alkyl, and acyl;

Z is C or N, where - - - represents a double bond when Z is C or a single bond when Z is N;

m is 1, 2 or 3; and n is 2, 3, 4, 5 or 6.

In some embodiments of the invention, Z is C. In other embodiments, Z is N.

In some embodiments of the invention, at least one X is $CH_2$ or CHY. In other embodiments, at least one X is NH or NY. In other embodiments, at least one X is S.

In some embodiments, the compound of the invention has the formula (II):

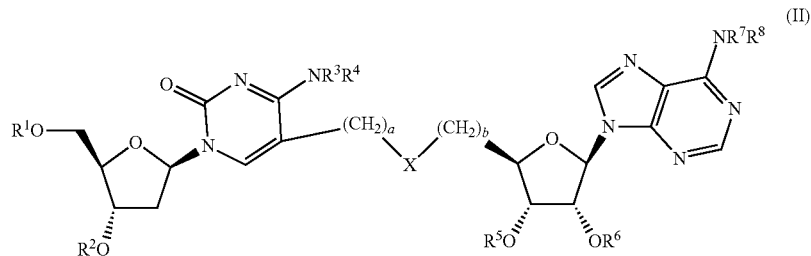

wherein:
X is NH or NY;
a and b are each 1, 2 or 3; and
Y and $R^1$ to $R^8$ are as defined above.
In some embodiments of the invention, a and b are both 1, or a is 2 or 3 and b is 1, or a is 1 and b is 2 or 3. Preferably, X is NY.
In some other embodiments, the compound has the formula (III):

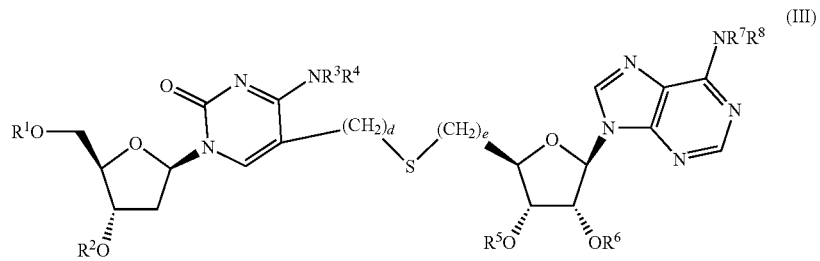

wherein:
d is 0 or 1;
e is 0, 1, 2 or 3; and
Y and $R^1$ to $R^8$ are as defined above.
In some embodiments of the invention, d is 1 and e is 3.
In some compounds of formula (I), one X is S and another X is NY. Alternatively, one X is NH and another X is CHY.
In some embodiments of the invention, one of $R^1$ to $R^8$ is H and the others are $C_1$-$C_3$ alkyl or acyl.
In some embodiments of the invention, two of $R^1$ to $R^8$ are H and the others are $C_1$-$C_3$ alkyl or acyl.
In some embodiments of the invention, three of $R^1$ to $R^8$ are H and the others are $C_1$-$C_3$ alkyl or acyl.
In some embodiments of the invention, four of $R^1$ to $R^8$ are H and the others are $C_1$-$C_3$ alkyl or acyl.
In some embodiments of the invention, five of $R^1$ to $R^8$ are H and the others are $C_1$-$C_3$ alkyl or acyl.
In some embodiments of the invention, six of $R^1$ to $R^8$ are H and the others are $C_1$-$C_3$ alkyl or acyl.
In some embodiments of the invention, seven of $R^1$ to $R^8$ are H and the others are $C_1$-$C_3$ alkyl or acyl.
In some embodiments of the invention, all of $R^1$ to $R^8$ is H.
In a second aspect, the invention provides a pharmaceutical composition comprising a compound of the formula (I) and a pharmaceutically acceptable carrier.
In a third aspect, the invention provides a method for inhibiting DNA methyltransferase 1 in a subject which comprises administering to a subject a therapeutically effective amount of a compound of formula (I).

In a further aspect, the invention provides a method of treating cancer which comprises administering to a subject a therapeutically effective amount of a compound of formula (I).

In a further aspect, the invention provides the use of a compound of formula (I) in the manufacture of a medicament for the inhibition of DNA methyltransferase 1.

In a further aspect, the invention provides a pharmaceutical composition comprising a compound of formula (I) for use as an inhibitor of DNA methyltransferase 1.

BRIEF DESCRIPTION OF THE FIGURE

FIG. 1 shows DNA methylation catalysed by DNMT1.

DETAILED DESCRIPTION

The invention provides certain compounds as inhibitors of DNMT1 and their use for the treatment of cancer. The invention is based on the finding that specific compounds of general formula (I) are effective inhibitors of DNMT1.
Definitions
The term "alkyl" as used herein refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.
The term "acyl" as used herein refers to the C(=O)R' group, where R' is a $C_1$-$C_3$alkyl group, where $C_1$-$C_3$alkyl means any saturated hydrocarbon radical having up to 3 carbon atoms, and is intended to include straight chain alkyl groups. Examples include acetyl group.

The term "pharmaceutical composition" as used herein refers to a mixture of one or more of the compounds of formula (I), or pharmaceutically acceptable salts, or hydrates thereof, with other chemical components, such as physiologically acceptable carriers and excipients. The purpose of a pharmaceutical composition is to facilitate administration of a compound to an organism.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carrier may also be saline, gum acacia, gelatin, starch paste, talc, keratin, colloidal silica, urea, and the like. In addition, auxiliary, stabilizing, thickening, lubricating, and coloring agents may be used. Other examples of suitable pharmaceutical carriers are described in "Remington's Pharmaceutical Sciences" by E. W. Martin, herein incorporated by reference.

The term "pharmaceutically acceptable salt" as used herein refers to any salt of a compound provided herein which retains its biological properties and which is not toxic or otherwise undesirable for pharmaceutical use and is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of formula (I).

The terms "treatment", "treating" and the like include the alleviation of one or more symptoms, or improvement of a state associated with the disease or disorder, for example, improvement in cognition, improvement in memory function.

The terms "preventing", "prevention" and the like include the prevention of one or more symptoms associated with the disease or disorder.

The compounds of the invention are useful in both free base form and in the form of salts and/or solvates.

Compounds of the Invention

The compounds of the invention have the general formula (I):

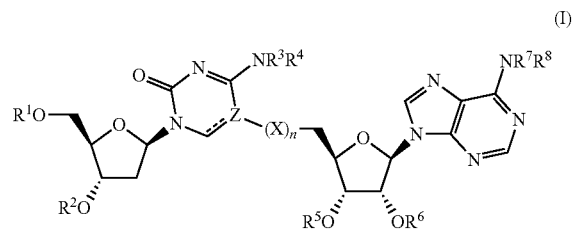

wherein:

each X is independently selected from the group comprising $CH_2$, CHY, NH, NY, and S, provided that no more than one X is CHY or NY,
where Y is:

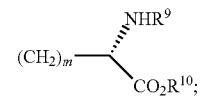

$R^1$ to $R^{10}$ are each independently selected from the group comprising H, alkyl, and acyl;

Z is C or N, where - - - represents a double bond when Z is C or a single bond when Z is N;

m is 1, 2 or 3; and n is 2, 3, 4, 5 or 6.

It will be appreciated that the linker moiety identified as "$(X)_n$" may be an alkyl chain or may comprise one or more N or S heteroatoms. The length of the linker chain may comprise 2 to 6 atoms. Some compounds of the invention comprise one CHY or NY group. Other compounds of the invention do not have a y group.

Some compounds of the invention having a nitrogen atom in the linker chain have the formula (II):

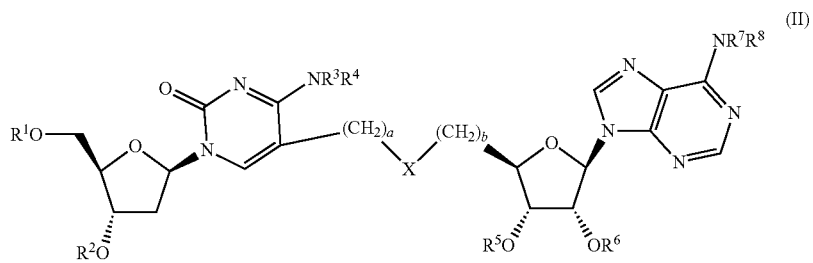

wherein:

X is NH or NY;

a and b are each 1, 2 or 3; and

Y and $R^1$ to $R^8$ are as defined above.

Each of a and b may be 1, 2 or 3. However, in preferred compounds of the invention, a and b are both 1. In other preferred compounds, a is 2 or 3 and b is 1, or a is 1 and b is 2 or 3. Preferably, X is NY.

Some compounds of the invention having a sulfur atom in the linker chain have the formula (III):

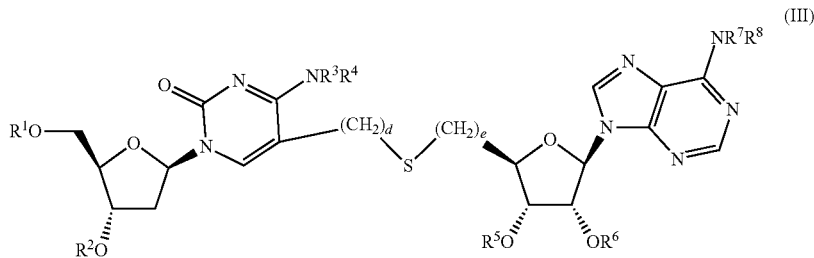

wherein:
d is 0 or 1;
e is 0, 1, 2 or 3; and
Y and $R^1$ to $R^8$ are as defined above.

In some preferred embodiments of the invention, d is 1 and e is 3.

In some preferred compounds of formula (I), one X is S and another X is NY. In other preferred compounds of formula (I), one X is NH and another X is CHY.

It will be appreciated that any combination of $R^1$ to $R^8$ being H, $C_1$-$C_3$ alkyl or acyl are contemplated as part of the invention. For example, 1, 2, 3, 4, 5, 6, 7, or all 8 of $R^1$ to $R^8$ may be H. Those $R^1$ to $R^8$ groups that are not H, may be either $C_1$-$C_3$ alkyl or acyl. 1.

Some specific compounds of the invention include the following:

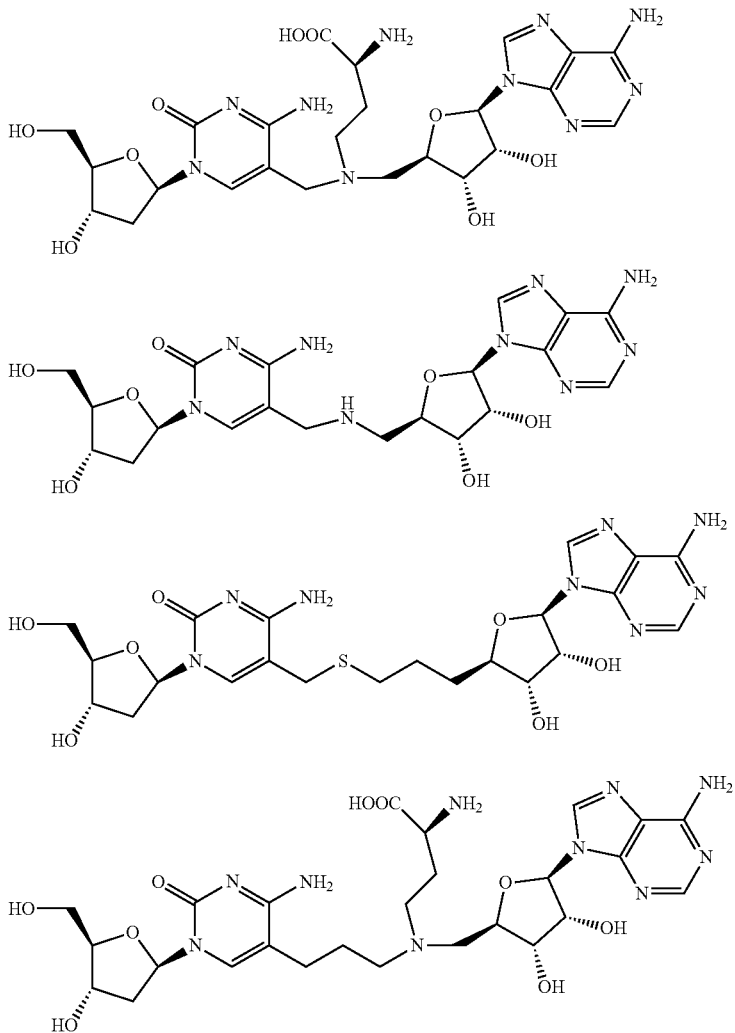

-continued

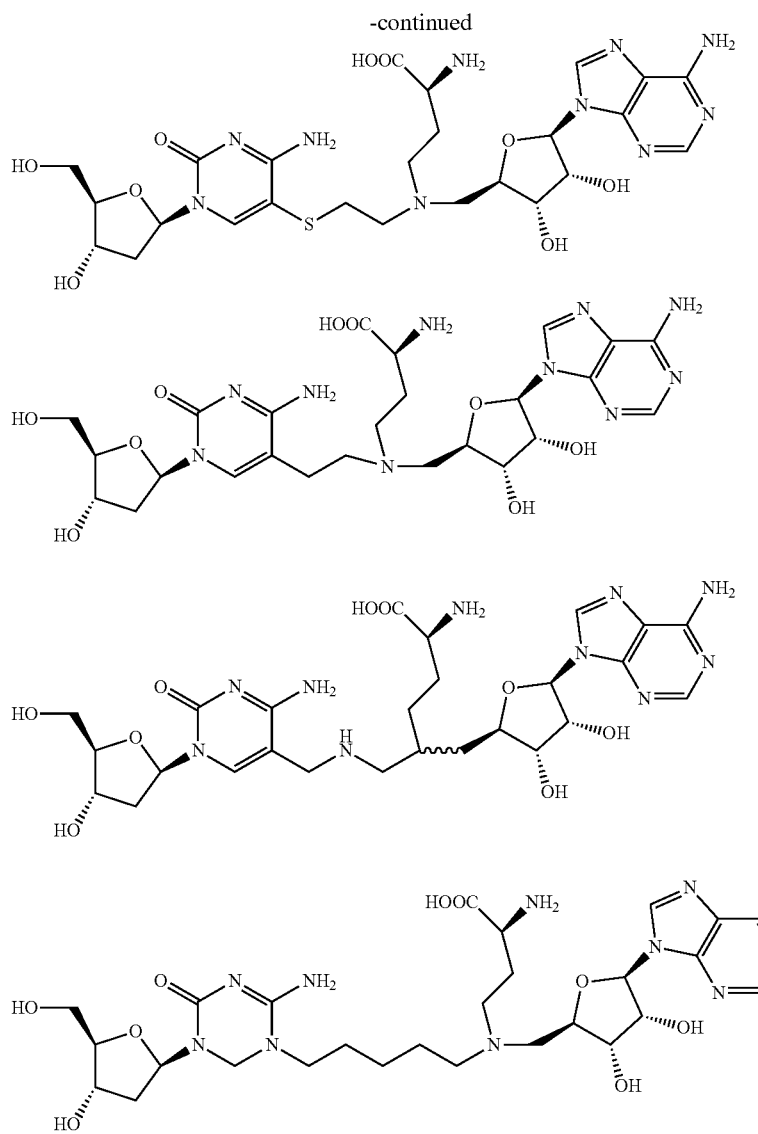

and

The compounds of the invention are, or are expected to be, effective inhibitors of DNA methyltransferase 1. They therefore have potential as therapeutic agents against a range of cancers.

The compounds of formula (I) may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomer usually produces a mixture whose chemical and physical properties are consistent with a mixture of compounds. The position of the equilibrium is dependent on chemical features within the molecule. The compounds of the invention may also include salts, hydrates and/or solvates thereof.

Preparation of Compounds

The compounds of the invention may be prepared according to the methods described in the Examples. It will be appreciated that the methods used for preparing the compounds of the Examples may also be used for other compounds of the invention together with standard techniques and procedures as would be understood by those skilled in the art.

Formulations and Administration

The compounds of the invention may be administered to a patient by a variety of routes, including orally, parenterally, by inhalation spray, topically, rectally, nasally, buccally or via an implanted reservoir. For parenteral administration, injections may be given intravenously, intra-arterially, intramuscularly or subcutaneously.

The amount of a compound of the invention to be administered to a patient will vary widely according to the nature of the patient and the nature and extent of the disorder to be treated. Typically the dosage for an adult human will be in the range of about 0.01 μg/kg to about 1 g/kg, and preferably about 0.01 mg/kg to about 100 mg/kg. The specific dosage required for any particular patient will depend upon a variety of factors, such as the patient's age, body weight, general health, gender and diet. Optimal doses will depend on other factors such as mode of administration and level of progression of the disease or disorder. Doses may be given once daily, or two or more doses may be required per day. For example, a dosage regime for a malaria patient might require one dose in the morning and one in the evening. Alternatively, a dosage regime for such a patient might require four hourly doses.

For oral administration the compounds can be formulated into solid or liquid preparations, for example tablets, capsules, granules, powders, solutions, suspensions, syrups, elixirs and dispersions. Such preparations are well known in the art as are other oral dosage regimes not listed here.

For parenteral administration, compounds of the invention can be formulated into sterile solutions, emulsions and suspension.

Compounds of the invention may be mixed with suitable vehicle and then compressed into the desired shape and size. The compounds may be tableted with conventional tablet bases such as lactose, sucrose and corn starch, together with a binder, a disintegration agent and a lubricant. The binder may be, for example, corn starch or gelatin, the disintegrating agent may be potato starch or alginic acid, and the lubricant may be magnesium stearate. For oral administration in the form of capsules, diluents such as lactose and dried cornstarch may be employed. Other components such as colourings, sweeteners or flavourings may be added. Tablets, capsules or powders for oral administration may contain up to about 99% of a compound of the invention.

When liquid preparations are required for oral use, a compound of the invention may be combined with a pharmaceutically acceptable carriers such as water, an organic solvent such as ethanol, or a mixture of both, and optionally other additives such as emulsifying agents, suspending agents, buffers, preservatives, and/or surfactants may be used. Colourings, sweeteners or flavourings may also be added.

The compounds may also be administered by injection in a pharmaceutically acceptable diluent such as water or saline. The diluent may comprise one or more other ingredients such as ethanol, propylene glycol, an oil or a pharmaceutically acceptable surfactant.

The compounds of the invention may also be administered topically. Carriers for topical administration of the compounds include mineral oil, liquid petrolatum, white petrolatum, propylene glycol, polyoxyethylene, polyoxypropylene compound, emulsifying wax and water. The compounds may be present as ingredients in lotions or creams, for topical administration to skin or mucous membranes. Such creams may contain the active compounds suspended or dissolved in one or more pharmaceutically acceptable carriers. Suitable carriers include mineral oil, sorbitan monostearate, polysorbate 60, cetyl ester wax, cetearyl alcohol, 2-octyldodecanol, benzyl alcohol, and water.

The compounds of the invention may further be administered by means of sustained release systems. For example, they may be incorporated into a slowly dissolving tablet or capsule.

DNA Methyl Transferases

The compounds of this invention are designed to inhibit DNMT1. Human DNA methyltransferases (DNMTs) catalyse the formation of 5-methylcytosine (5mC) at CpG sites on DNA, a key epigenetic mark present in the human genome. DNA methylation is involved in transcriptional silencing, cellular differentiation, genomic imprinting, and X-chromosome inactivation. In addition, hypermethylation of CpG islands at gene promoter regions has been associated with carcinogenesis. Maintenance of DNA methylation patterns is conducted by human DNMT1, a multidomain protein of 1,616 amino acids. The C-terminal methyltransferase domain shows sequence similarities to the bacterial methyltransferases. Crystal structures of mouse and human DNMT1 complexed with different substrates have provided a structural basis for DNMT1-mediated maintenance DNA methylation. Domain interactions and large conformational changes are responsible for properly positioning hemimethylated DNA within the active site and catalyse methyl transfer from S-adenosyl-L-methionine (SAM) to DNA. Site-directed mutations have offered insights into the structure function relationship of DNMTs, but their transition state (TS) structures have remained unknown. DNMT1 has been proposed to follow a catalytic mechanism shared by bacterial DNA-(cytosine C5)-methyltransferases: nucleophilic attack of cytosine (Cyt) C6 by Cys1226 of DNMT1, methyl transfer from SAM to Cyt C5, and β-elimination of H5 to produce 5mC in the final step. FIG. 1 shows a proposed catalytic mechanism for DNMT1 involving three chemical TSs (TS1, TS2, and TS3). Cys1226 attack (TS1) brings a negative charge (−1) to the Cyt ring, whereas Cys elimination (TS3) restores the aromaticity of the Cyt. Based on the KIE analysis methyl transfer (TS2) is chemically rate-limiting for DNMT1 and has a higher energy barrier than the thiol-attack and β-elimination steps. The combination of kinetic isotope effects (KIEs) and computational chemistry can test predicted reaction mechanisms and can provide a model of the TS structure. The transition state of human DNMT1 has recently been published (Du, Q., Wang, Z., Schramm, V. L., Proc. Natl. Acad. Sci. USA, 113, 2916-2921, 2016).

EXAMPLES

The following examples further illustrate the invention. It is to be appreciated that the invention is not limited to the examples.

Example 1: Synthesis of (S)-2-amino-4-(((4-amino-1-((2R,4S,5R)-4-hydroxy-5-(hydroxy-methyl)tetrahydrofuran-2-yl)-2-oxo-1,2-dihydropyrimidin-5-yl)methyl)-(((2R,3S,4R,5R)-5-(6-amino-9H-purin-9-yl)-3,4-dihydroxytetrahydrofuran-2-yl)methyl)amino)butanoic acid 7

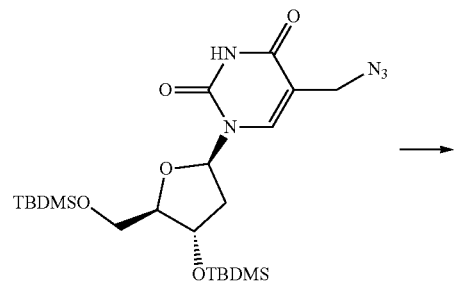

1

-continued
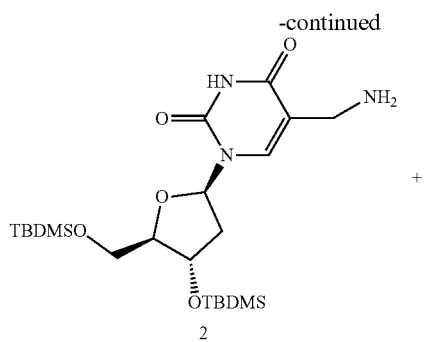
2
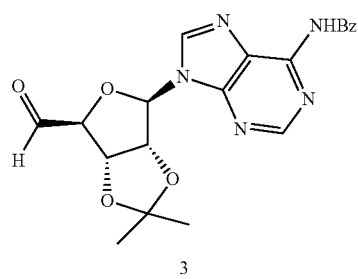
3
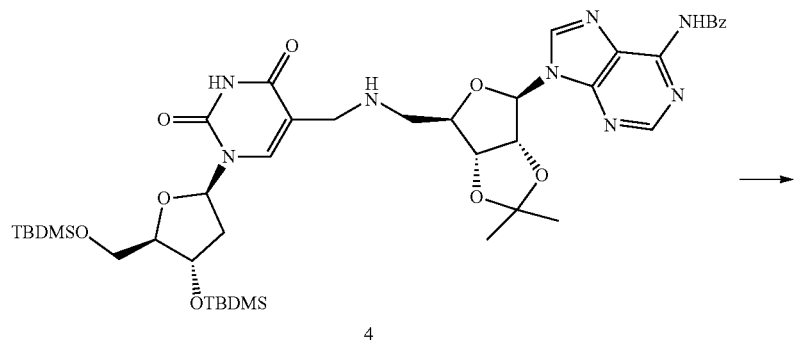
4
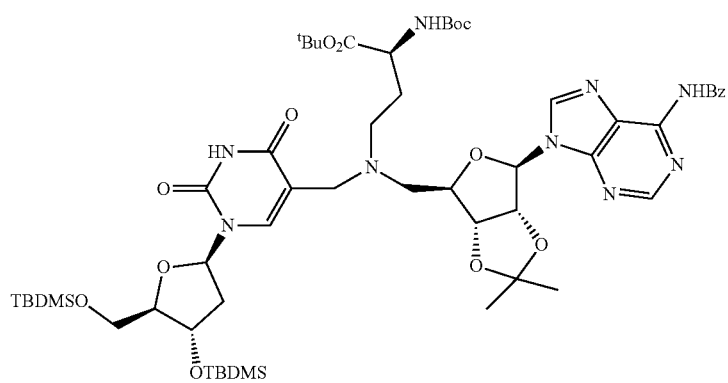
5

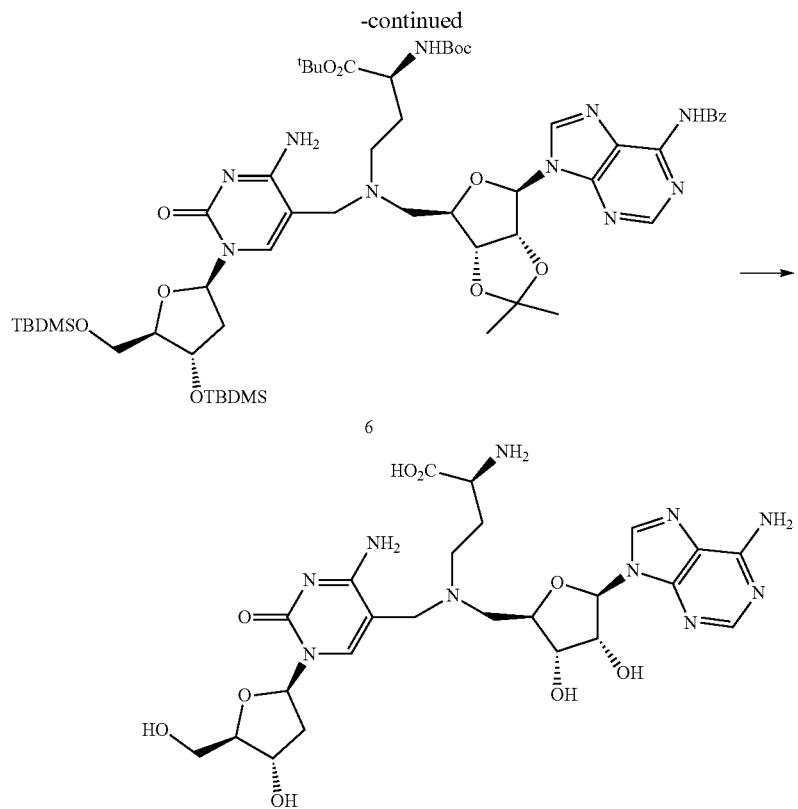

A solution of azide 1 (Miyata, K., Tamamushi, R., Ohkubo, A., Taguchi, H., Seio, K., Santa, T., and Sekine, M., Org. Lett. 2006, 8(8), 1545-1548) (4.56 g, 8.9 mmol) in methanol (100 mL) was stirred under a hydrogen balloon in the presence of 10% Pd/C (500 mg) for 2 hours. The mixture was filtered and evaporated to give 5-(aminomethyl)-1-((2R, 4S,5R)-4-((tert-butyldimethylsilyl)oxy)-5-(((tert-butyldimethylsilyl)oxy)methyl)tetrahydrofuran-2-yl)pyrimidine-2,4 (1, 3H)-dione 2 (3.45 g, 80%) as an oil. $^1$H NMR (500 MHz, MeOD) δ7.50 (s, 1H), 6.15-6.10 (m, 1H), 4.37-4.33 (m, 1H), 3.82-3.78 (m, 1H), 3.71-3.68 (m, 1H), 3.36-3.33 (m, 2H), 2.13-2.02 (m, 2H), 0.81 (s, 18H), 0.00 (s, 12H). $^{13}$C NMR (125 MHz, MeOD) δ166.1, 152.3, 138.2, 115.9, 89.3, 86.5, 74.0, 64.4, 41.4, 40.0, 26.5, 26.3, 19.3, 18.9, 0.0. HRMS (m/z) calcd. for $C_{22}H_{44}N_3O_5Si_2[M+H]^+$ 486.2820, found 486.2828.

To the aldehyde 3 (Ranganathan, R. S., Jones, G. H., and Moffat, J. G., J. Org. Chem., 1974, 39, 290-298) (189 mg, 0.5 mmol) [which had been dehydrated by co-distillation with benzene] in absolute ethanol (20 mL) was added amine 2 (246 mg, 0.5 mmol) and the pH was adjusted to −6.5 with acetic acid. Picoline borane complex (100 mg, 1 mmol) was added and the solution was stirred at room temperature overnight. The mixture was evaporated onto silica gel and chromatographed eluting with dichloromethane, then a gradient of 2%, 5%, 10% 6M methanolic ammonia in dichloromethane, to give N-(9-((3aR,4R,6R,6aR)-6-((((1-((2R,4S, 5R)-4-((tert-butyldimethylsilyl)oxy)-5-(((tert-butyldimethylsilyl)oxy)methyl)tetrahydrofuran-2-yl)-2,4-dioxo-1,2,3,4-tetrahydropyrimidin-5-yl)methyl)amino) methyl)-2,2-dimethyltetrahydrofuro[3,4-d][1,3]dioxol-4-yl)-9H-purin-6-yl)benzamide 4 (274 mg, 68%) as a foam. $^1$H NMR (500 MHz, MeOD) δ8.63-8.42 (m, 2H), 8.04-7.98 (m, 2H), 7.59-7.54 (m, 1H), 7.50-7.45 (m, 3H), 6.23-6.19 (m, 1H), 6.13-6.08 (m, 1H), 5.50-5.27 (m, 1H), 5.03-4.95 (m, 1H), 4.35-4.28 (m, 2H), 3.96-3.81 (m, 1H), 3.73-3.45 (m, 2H), 2.87-2.72 (m, 1H), 2.15-1.94 (m, 2H), 1.55-1.49 (m, 3H), 1.33-1.28 (m, 3H), 0.85-0.78 (m, 18H), 0.00 (m, 12H). $^{13}$C NMR (125 MHz, MeOD) δ168.2, 175.3, 153.1, 152.7, 151.9, 151.1, 145.7, 144.8, 139.6, 134.9, 134.0, 129.8, 129.5, 125.4, 115.5, 115.3, 111.6, 92.7, 92.1, 89.4, 88.8, 87.6, 86.8, 85.7, 85.3, 84.2, 83.0, 74.0, 64.4, 63.4, 51.1, 47.6, 41.6, 27.6, 27.4, 26.5, 26.3, 25.6, 19.3, 18.9, −4.6, −4.9. HRMS (m/z) calcd. for $C_{42}H_{63}N_8O_9Si_2$ $[M+H]^+$ 879.4248, found 879.4257.

To the amine 4 (274 mg, 0.3 mmol) in absolute ethanol (10 mL) was added tert-butyl L-2-((tert-butoxycarbonyl) amino)-4-oxobutanoate (Roberts, S. J., Morris, J. C., Dobson, R. C. J., Baxter, C. L., Gerrard, J. A., ARKIVOC 2004, 166-177; http://hdl.handle.net/2440/34486) (85 mg, 0.3 mmol) and then picoline borane complex (66 mg, 0.6 mmol) and the mixture was stirred at room temperature overnight. The mixture was then evaporated onto silica gel and chromatographed eluting with 20%, 50% hexanes-ethyl acetate, 5%, 10% 6M methanolic ammonia in dichloromethane, to give tert-butyl (S)-4-((((3aR,4R,6R,6aR)-6-(6-benzamido-9H-purin-9-yl)-2,2-dimethyltetrahydrofuro[3,4-d][1,3]dioxol-4-yl)methyl)((1-((2R,4S,5R)-4-((tert-butyldimethylsilyl)oxy)-5-(((tert-butyldimethylsilyl)oxy)methyl) tetrahydrofuran-2-yl)-2,4-dioxo-1,2,3,4-tetrahydropyrimidin-5-yl)methyl)amino)-2-((tert-butoxycarbonyl)amino)butanoate 5 (300 mg, 88%) as a foam. $^1$H NMR (500 MHz, CDCl$_3$) δ9.47-8.80 (m, 3H), 8.80-8.74 (m, 1H), 8.22-8.14 (m, 1H), 8.04-8.00 (m, 2H), 7.59-7.35 (m, 4H), 6.12-6.05 (m, 2H), 5.50-5.40 (m, 1H), 5.31-5.20 (m, 1H), 5.01-4.90 (m, 1H), 4.40-4.28 (m, 2H), 4.12-4.02 (m, 1H), 3.89-3.82 (m, 1H), 3.72-3.62 (m, 1H), 3.44-3.17 (m, 2H), 2.76-2.61 (m, 2H), 2.58-2.49 (m, 2H), 2.21-1.64 (m, 3H), 1.63-1.30 (m, 24H), 0.93-0.81 (m, 18H), 0.10-0.00 (m, 12H). $^{13}$C NMR (125 MHz, CDCl$_3$) δ171.5, 164.9, 163.1, 152.7, 151.4, 150.1, 150.0, 142.6, 138.9, 133.6, 132.6, 128.7, 128.2, 123.8, 114.6, 111.1, 90.8, 87.8, 85.6, 84.0, 83.0, 79.6, 72.5, 63.2, 55.7, 52.8, 50.6, 40.4, 29.7, 28.4, 28.0, 27.2, 26.0, 25.7, 25.5, 18.4, 18.0, −0.46, −0.51. HRMS (m/z) calcd. for C$_{55}$H$_{85}$N$_9$O$_{13}$Si$_2$Na [M+Na]$^+$ 1158.5703, found 1158.5701.

To the amine 5 (300 mg, 0.26 mmol) in dichloromethane (15 mL) and 0.1 M sodium carbonate (30 mL) was added tetrabutylammonium bromide (84 mg, 0.26 mmol) and triisopropylbenzenesulfonyl chloride (1.2 g, 4 mmol) and the mixture was stirred vigorously overnight. The reaction mixture was then diluted with dichloromethane and the organic phase was washed with saturated aqueous sodium bicarbonate, brine, dried and evaporated. The excess reagents were removed by silica column chromatography and the product was dissolved in dry 1,4-dioxane (5 mL) and stirred under ammonia gas for 4 hours. The solution was evaporated and silica gel chromatography eluting with dichloromethane, then 2%, 5% 6M methanolic ammonia in dichloromethane gave tert-butyl (S)-4-(((4-amino-1-((2R, 4S,5R)-4-((tert-butyldimethylsilyl)oxy)-5-(((tert-butyldimethylsilyl)oxy)methyl)tetrahydrofuran-2-yl)-2-oxo-1,2-dihydropyrimidin-5-yl)methyl)(((3aR,4R,6R,6aR)-6-(6-benzamido-9H-purin-9-yl)-2,2-dimethyltetrahydrofuro[3,4-d][1,3]dioxol-4-yl)methyl)amino)-2-((tert-butoxycarbonyl)amino)butanoate 6 (84 mg, 28%) as a foam. $^1$H NMR (500 MHz, CDCl$_3$) δ9.53-9.43 (m, 1H), 8.63 (s, 1H), 8.15-8.00 (m, 3H), 7.58-7.36 (m, 4H), 6.30-6.25 (m, 1H), 6.13-6.08 (m, 1H), 5.48-5.40 (m, 1H), 5.07-4.94 (m, 2H), 4.40-4.24 (m, 2H), 4.16-4.05 (m, 2H), 3.92-3.79 (m, 2H), 3.73-3.54 (m, 5H), 3.09-2.74 (m, 2H), 2.60-2.29 (m, 4H), 1.96-1.78 (m, 2H), 1.58-1.20 (m, 24H), 0.90-0.79 (m, 18H), 0.05-0.08 (m, 12H). $^{13}$C NMR (125 MHz, CDCl$_3$) δ171.4, 164.9, 155.4, 152.4, 150.9, 150.4, 142.9, 139.4, 133.5, 132.6, 127.7, 128.2, 128.0, 127.4, 124.9, 114.6, 101.5, 98.9, 90.8, 90.6, 87.5, 85.9, 85.4, 84.3, 83.5, 80.0, 71.6, 70.1, 66.1, 66.0, 62.7, 62.3, 61.2, 55.5, 54.4, 52.3, 50.0, 42.2, 28.3, 28.0, 27.1, 26.1, 26.0, 25.8, 25.3, 18.5, 18.0, −4.4, −4.8, −5.1. HRMS (m/z) calcd. for C$_{55}$H$_{86}$N$_{10}$O$_{12}$Si$_2$Na [M+Na]$^+$ 1157.5852, found 1157.5848.

The amine 6 (84 mg, 0.07 mmol) was treated with ice cold 6M methanolic ammonia (2 mL) and then stirred a room temperature overnight. The released benzamide was removed by silica gel chromatography eluting with 2% to 10% 6M methanolic ammonia in dichloromethane. The product was treated with ice cold 90% aqueous trifluoroacetic acid (1 mL) and stirred at 0° C. for 2 hours. The reaction mixture was evaporated under high vacuum at room temperature and then from ethanol. This product was treated at room temperature with neat trifluoroacetic acid (0.2 mL) for 1 hour and then evaporated. The product was purified on C18 reverse-phase silica gel eluting with water, and then 20%, 40% methanol in water to give (S)-2-amino-4-(((4-amino-1-((2R,4S,5R)-4-hydroxy-5-(hydroxymethyl)tetrahydrofuran-2-yl)-2-oxo-1,2-dihydropyrimidin-5-yl)methyl) (((2R,3S,4R,5R)-5-(6-amino-9H-purin-9-yl)-3,4-dihydroxytetrahydrofuran-2-yl)methyl)amino)butanoic acid 7 as a glass (2 mg). $^1$H NMR (500 MHz, D$_2$O) δ8.20 (s, 1H), 8.16 (s, 1H), 7.68 (s, 1H), 6.11-6.08 (m, 1H), 6.02-5.97 (m, 1H), 4.81-4.79 (m, 1H), 4.32-4.26 (m, 3H), 4.00-3.96 (m, 1H), 3.80-3.64 (m, 4H), 3.54-3.35 (m, 2H), 2.88-2.84 (m, 1H), 2.75-2.69 (m, 1H), 2.30-1.93 (m, 4H). $^{13}$C NMR (125 MHz, D$_2$O) δ174.1, 165.4, 157.0, 155.7, 153.0, 148.8, 140.7, 140.3, 119.2, 104.3, 88.3, 86.6, 86.0, 81.6, 72.8, 72.0, 70.3, 61.0, 55.2, 53.9, 53.2, 50.7, 39.4, 27.2. HRMS (m/z) calcd. for C$_{24}$H$_{35}$N$_{10}$O$_9$ [M+H]$^+$ 607.2588, found 607.2592.

Example 2: Synthesis of 4-amino-5-(((((2R,3S,4R,5R)-5-(6-amino-9H-purin-9-yl)-3,4-dihydroxytetrahydrofuran-2-yl)methyl)amino)methyl)-1-((2R,4S,5R)-4-hydroxy-5-(hydroxymethyl)tetrahydrofuran-2-yl)pyrimidin-2(1H)-one 10

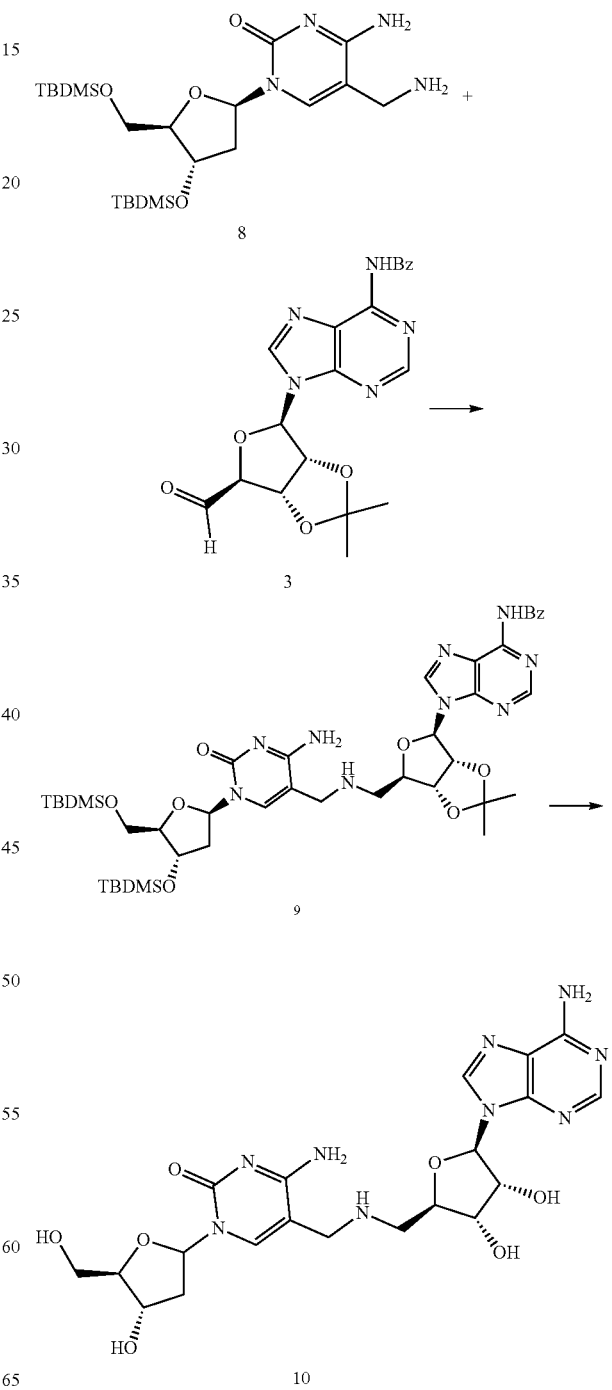

The 5-aminomethylcytidine 8 (0.56 g, 1.2 mmol) was added to aldehyde 3 (0.48 g, 1.2 mmol) and the mixture was dissolved in benzene and concentrated to dryness twice. The residue was dissolved in methanol/acetic acid (13 mL, 10/1 v/v). This solution was stirred and picoline borane (0.13 g, 1.2 mmol) was added. The solution was stirred for 4 days and then concentrated to dryness. Dichloromethane was added and the organic layer washed with saturated aqueous sodium bicarbonate, dried over magnesium sulfate, filtered and concentrated. Chromatography with a gradient elution of 0-10% methanol/ethyl acetate gave N-(9-((3aR,4R,6R,6aR)-6-(((((4-amino-1-((2R,4S,5R)-4-((tert-butyldimethylsilyl)oxy)-5-(((tert-butyldimethylsilyl)oxy)methyl)tetrahydrofuran-2-yl)-2-oxo-1,2-dihydropyrimidin-5-yl)methyl)amino)methyl)-2,2-dimethyltetrahydrofuro[3,4-d][1,3]dioxol-4-yl)-9H-purin-6-yl)benzamide 9 (0.457 g, 46%). $^1$H NMR (500 MHz, CDCl$_3$) δ8.71 (s, 1H), 8.12-8.05 (m, 3H), 7.63-7.58 (m, 1H), 7.57-7.50 (m, 3H), 6.31 (dd, J=7.1, 5.9 Hz, 1H), 6.08 (d, J=2.7 Hz, 1H), 5.55 (dd, J=6.4, 2.7 Hz, 1H), 5.02 (dd, J=6.4, 3.6 Hz, 1H), 4.37-4.31 (m, 2H), 3.92 (q, J=2.9 Hz, 1H), 3.85 (dd, J=11.3, 2.8 Hz, 1H), 3.73 (dd, J=11.3, 2.8 Hz, 1H), 3.60 (dd, J=13.2, 0.9 Hz, 1H), 3.44 (d, J=13.3 Hz, 1H), 2.87 (d, J=5.7 Hz, 2H), 2.42 (ddd, J=13.3, 6.0, 3.4 Hz, 1H), 1.92 (dt, J=13.3, 6.7 Hz, 1H), 1.62 (s, 3H), 1.40 (s, 3H), 0.88 (s, 9H), 0.87 (s, 9H), 0.07 (s, 3H), 0.06 (s, 3H), 0.05 (s, 3H), 0.04 (s, 3H). $^{13}$C NMR (126 MHz, CDCl$_3$) δ165.60, 164.66, 155.65, 152.53, 151.21, 150.13, 142.72, 138.80, 133.47, 132.80, 128.86, 128.01, 124.36, 114.88, 102.46, 91.03, 87.69, 86.09, 85.78, 83.47, 82.50, 71.88, 62.82, 50.11, 48.82, 42.26, 27.27, 25.98, 25.78, 25.39, 18.39, 18.01, −4.54, −4.86, −5.29, −5.35. HRMS (m/z) calcd. for C$_{42}$H$_{64}$N$_9$O$_8$Si$_2$ [M+H]$^+$ 878.4411, found 878.4412.

To a solution of amine 9 (0.02 g, 0.023 mmol) in methanol (0.4 mL) at 0° C., methanolic ammonia (7 mol/L, 1.5 mL) was added and the reaction was stirred at room temperature overnight. The volatiles were removed under vacuum and the reaction mixture was dissolved in 9:1 trifluoroacetic acid:water (1 mL) and stirred at 0° C. for 1 hour followed by 2 hours at room temperature. The reaction mixture was concentrated under vacuum and co-evaporated with ethanol. The residue was subjected to silica gel flash column chromatography employing gradient elution eluting from 100% acetonitrile to acetonitrile:water:methanol 8.5:1.5:1.5 to give 4-amino-5-(((((2R,3S,4R,5R)-5-(6-amino-9H-purin-9-yl)-3,4-dihydroxytetrahydrofuran-2-yl)methyl)amino)methyl)-1-((2R,4S,5R)-4-hydroxy-5-(hydroxymethyl)tetrahydrofuran-2-yl)pyrimidin-2(1H)-one 10 (6.0 mg, 52%) as a white solid. $^1$H NMR (500 MHz, D$_2$O) δ8.22 (s, 1H), 8.11 (s, 1H), 7.80 (s, 1H), 6.14 (t, J=6.79 Hz, 1H), 6.03 (d, J=4.97 Hz, 1H), 4.82 (dd, J=5.08 Hz, 1H), 4.42 (dd, J=5.08, 5.21 Hz, 1H), 4.33 (m, 1H), 4.28 (m, 1H), 3.99 (m, 1H), 3.78 (bs, 2H), 3.74 (dd, J=12.61, 3.45 Hz, 1H), 3.62 (dd, J=12.61, 5.03 Hz, 1H), 3.23-3.11 (m, 2H), 2.32 (ddd, J=14.2, 6.8, 4.1 Hz, 1H), 2.08-2.01 (m, 1H). $^{13}$C NMR (500 MHz, D$_2$O) δ164.9, 156.9, 155.7, 152.7, 148.7, 141.9, 140.8, 119.2, 102.7, 88.8, 86.8, 86.2, 82.0, 73.0, 71.6, 70.4, 61.1, 48.9, 45.2, 39.5. HRMS (m/z) calcd. for C$_{20}$H$_{28}$O$_7$N$_9$Na: [M+Na]$^+$ 506.2106: found 506.2119.

Example 3: Synthesis of 4-amino-5-(((3-((2R,3S,4R,5R)-5-(6-amino-9H-purin-9-yl)-3,4-dihydroxytetrahydrofuran-2-yl)propyl)thio)methyl)-1-((2R,4S,5R)-4-hydroxy-5-(hydroxymethyl)tetrahydrofuran-2-yl)pyrimidin-2(1H)-one 21

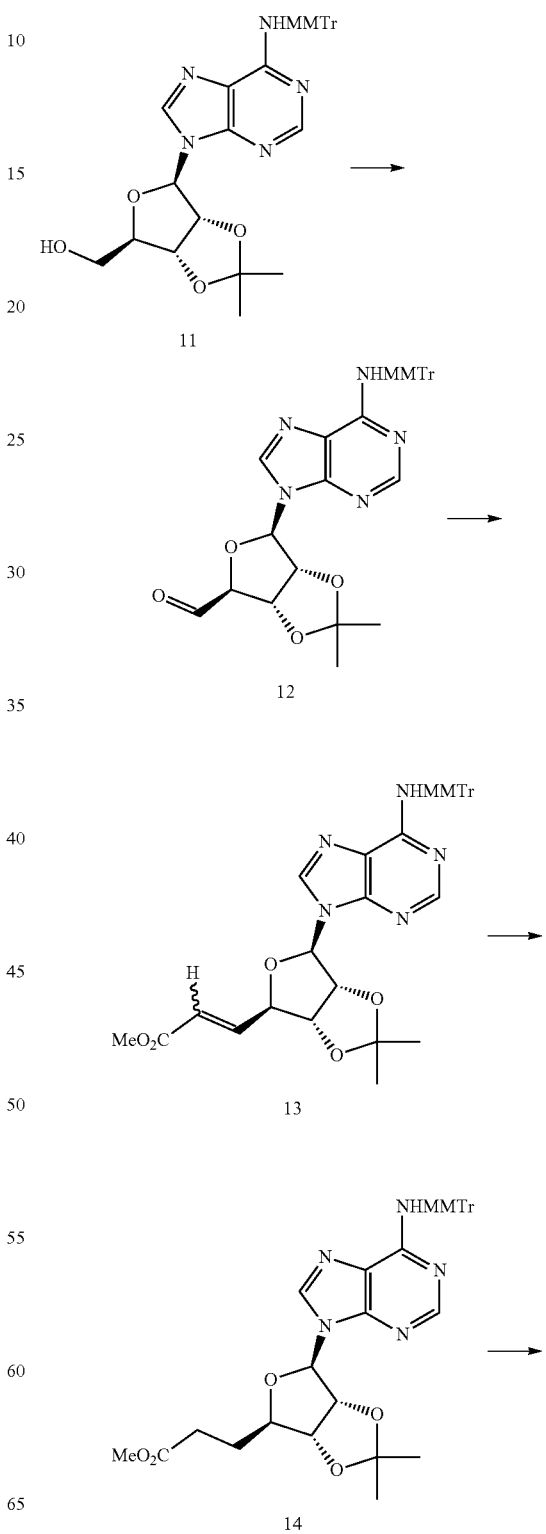

-continued

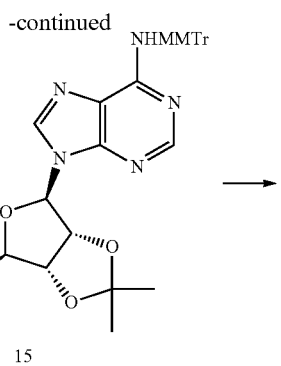

15

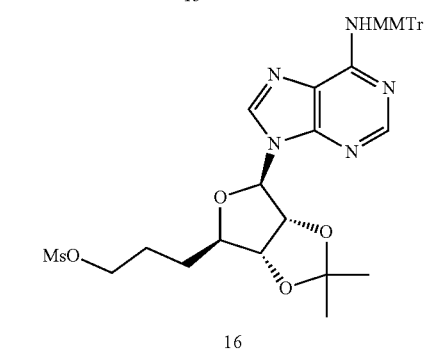

16

11 (2.00 g, 3.46 mmol) (Guillerm, G., Muzard, M., Glapski, C., Pilard, S., De Clercq, E., 3. Med. Chem. 2006, 49 (4), 1223-1226) and Dess-Martin periodinane (3.02 g, 6.91 mmol) were dissolved in dry dichloromethane (40 mL) and stirred at room temperature under argon for 2 hours until TLC showed the reaction was complete. The reaction was diluted with dichloromethane (200 mL) and quenched with 10% aqueous sodium thiosulfate (250 mL). The organic layer was then washed with saturated aqueous sodium bicarbonate (250 mL) then filtered and dried over anhydrous magnesium sulfate. The solvent was removed in vacuo to give (3a S,4S,6R,6a R)-6-(6-(((4-methoxyphenyl)diphenylmethyl)amino)-9H-purin-9-yl)-2,2-dimethyltetrahydrofuro[3,4-d][1,3]dioxole-4-carbaldehyde 12 as an oil which was used directly in the next step. $R_f$=0.21 (60% ethyl acetate/petroleum ether). HRMS (m/z) calcd. for $C_{34}H_{36}N_5O_6Na$ [M+Na]$^+$ 610.2666, found 610.2673.

12 (2.00 g, 3.46 mmol) and methyl (triphenylphosphoranylidene)acetate (1.42 g, 4.15 mmol) were dissolved in dry toluene (40 mL) and stirred at 80° C. under argon for 1 hour until TLC showed the reaction was complete. The reaction mixture was concentrated in vacuo. The residue was purified silica gel flash column chromatography eluting with an ethyl acetate petroleum ether gradient to give methyl (E,Z)-3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)acrylate 13 (1.61 g, 74% yield over two steps) as a white foam. $R_f$=0.70 (60% ethyl acetate/petroleum ether). HRMS (m/z) calcd. for $C_{36}H_{36}N_5O_6$ [M+H]$^+$ 634.2666, found 634.2673.

10% Palladium on carbon (1.61 g) was added to a solution of 13 (1.61 g, 2.55 mmol) in ethyl acetate (20 mL). The reaction was charged with a hydrogen atmosphere by successively evacuating then flushing with hydrogen three times. The reaction was stirred at room temperature under hydrogen for 3 hours until TLC showed the reaction was complete. The reaction mixture was filtered over a Celite pad, washing with additional ethyl acetate. The reaction mixture was concentrated in vacuo to give methyl 3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)propanoate 14 as a white foam which was used directly in the next step. $R_f$=0.27 (40% ethyl acetate/petroleum ether). $^1$H NMR (500 MHz, CDCl$_3$) δ8.04 (s, 1H), 7.81 (s, 1H), 7.43-7.12 (m, 12H), 6.91 (s, 1H), 6.79 (d, J=8.9 Hz, 2H), 5.98 (d, J=2.4 Hz, 1H), 5.43 (dd, J=6.5, 2.4 Hz, 1H), 4.82 (dd, J=6.4, 4.1 Hz, 1H), 4.17 (td, J=6.9, 4.4 Hz, 1H), 3.77 (s, 3H), 3.60 (s, 3H), 2.40 (t, J=7.5 Hz, 2H), 2.04 (q, J=7.7 Hz, 2H), 1.58 (s, 3H), 1.35 (s, 3H). $^{13}$C NMR (126 MHz, CDCl$_3$) δ173.15, 158.34, 154.20, 152.46, 148.28, 145.19, 139.06, 137.22, 130.20, 128.89, 127.86, 126.84, 121.54, 114.78, 113.16, 90.02, 85.55, 83.94, 83.86, 71.03, 55.21, 51.60, 30.10, 28.41, 27.21, 25.42. HRMS (m/z) calcd. for $C_{36}H_{38}N_5O_6Na$ [M+Na]$^+$ 636.2822, found 636.2819.

Lithium aluminium hydride (2.4 mL of a 2M solution in tetrahydrofuran, 4.84 mmol) was added to a solution of 14 (1.54 g, 2.42 mmol) in dry tetrahydrofuran (30 mL), the reaction was stirred at room temperature under argon for 15 minutes until TLC showed the reaction was complete. The reaction mixture was cooled on an ice-water bath then quenched with drop-wise addition of water (1 mL). The reaction mixture was diluted with dichloromethane (100 mL) and filtered over a Celite pad. The organic layer was washed with saturated aqueous brine (100 mL), filtered and dried over anhydrous magnesium sulfate then concentrated in vacuo. The residue was purified by silica gel flash column chromatography eluting with an ethyl acetate—petroleum ether gradient to give 3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)propan-1-ol 15 (1.21 g, 78% yield over two steps) as a white foam. $R_f$=0.22 (60% ethyl acetate/petroleum ether). $^1$H NMR (500 MHz, CDCl$_3$) δ8.04 (s, 1H), 7.83 (s, 1H), 7.45-7.10 (m, 12H), 6.94 (s, 1H), 6.79 (d, J=8.9 Hz, 2H), 5.99 (d, J=2.6 Hz, 1H), 5.43 (dd, J=6.6, 2.6 Hz, 1H), 4.79 (dd, J=6.6, 4.0 Hz, 1H), 4.18 (td, J=7.0, 4.0 Hz, 1H), 3.59 (q, J=5.8 Hz, 2H), 1.84-1.72 (m, 2H), 1.68-1.61 (m, 2H), 1.59 (s, 3H), 1.36 (s, 3H). $^{13}$C NMR (126 MHz, CDCl$_3$) δ158.33, 154.21, 152.48, 148.33, 145.18, 138.98, 137.21, 130.21, 128.90, 127.86, 126.85, 121.54, 114.76, 113.16, 90.12, 86.41, 84.06, 83.90, 71.05, 62.26, 55.22, 29.87, 28.79, 27.20, 25.42. HRMS (m/z) calcd. for $C_{35}H_{38}N_5O_5$ [M+H]$^+$ 608.2873, found 608.2870.

Methanesulfonyl chloride (0.168 mL, 2.15 mmol) was added drop-wise to an ice-cooled solution of 15 (0.873 g, 1.44 mmol) and triethylamine (0.405 mL, 2.87 mmol) in dry dichloromethane (22 mL) under argon. After 5 minutes the ice-bath was removed and the mixture stirred at room temperature for 30 minutes until TLC showed the reaction was complete. The reaction mixture was diluted with dichloromethane (100 mL), washed with saturated aqueous sodium bicarbonate (100 mL) then the organic layer was filtered and dried over anhydrous magnesium sulfate and concentrated in vacuo. The residue was purified by silica gel flash column chromatography eluting with an ethyl acetate—petroleum ether gradient to give 3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)propyl methanesulfonate 16 (0.890 g, 90% yield) as a white foam. R$_f$=0.50 (60% ethyl acetate/petroleum ether). $^1$H NMR (500 MHz, CDCl$_3$) δ8.04 (s, 1H), 7.81 (s, 1H), 7.43-7.15 (m, 12H), 6.92 (s, 1H), 6.79 (d, J=8.9 Hz, 2H), 5.98 (d, J=2.6 Hz, 1H), 5.44 (dd, J=6.6, 2.6 Hz, 1H), 4.83 (dd, J=6.6, 4.2 Hz, 1H), 4.30-4.03 (m, 3H), 3.77 (s, 3H), 2.89 (s, 3H), 1.93-1.76 (m, 4H), 1.59 (s, 3H), 1.35 (s, 3H). $^{13}$C NMR (126 MHz, CDCl$_3$) δ158.35, 154.23, 152.45, 148.26, 145.16, 139.15, 137.18, 130.20, 128.88, 127.88, 126.88, 121.58, 114.88, 113.17, 89.99, 85.88, 83.92, 83.84, 71.04, 69.18, 55.23, 37.39, 29.22, 27.22, 25.55, 25.41. HRMS (m/z) calcd. for C$_{36}$H$_{40}$N$_5$O$_7$S [M+H]$^+$ 686.2648, found 686.2654.

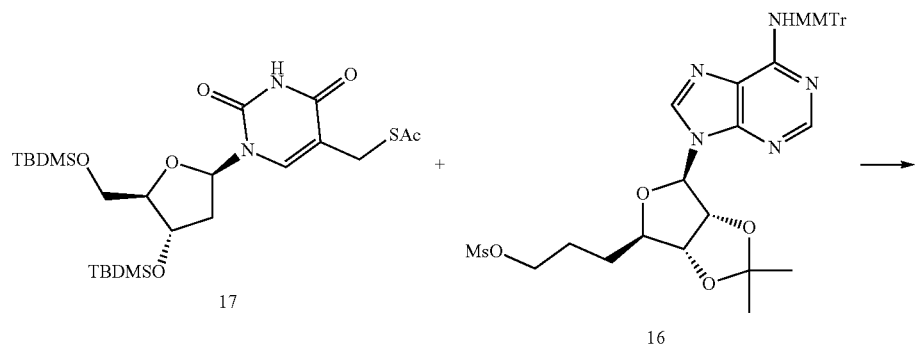

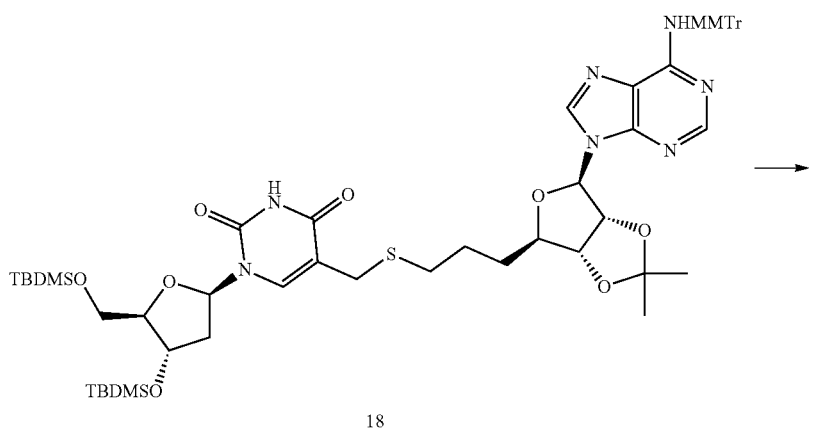

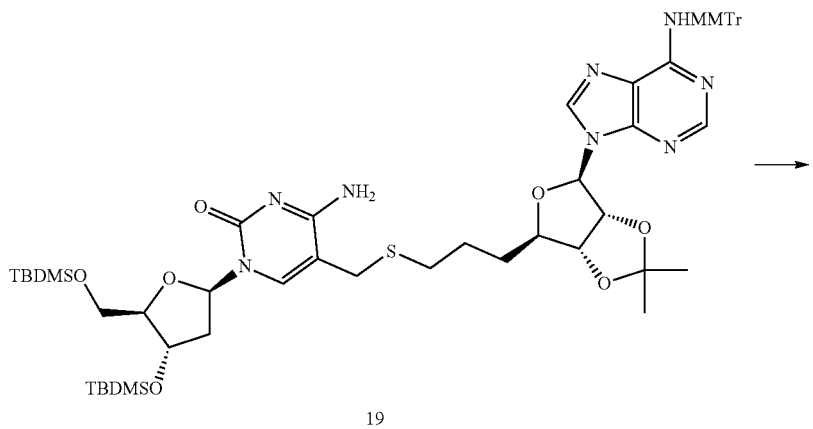

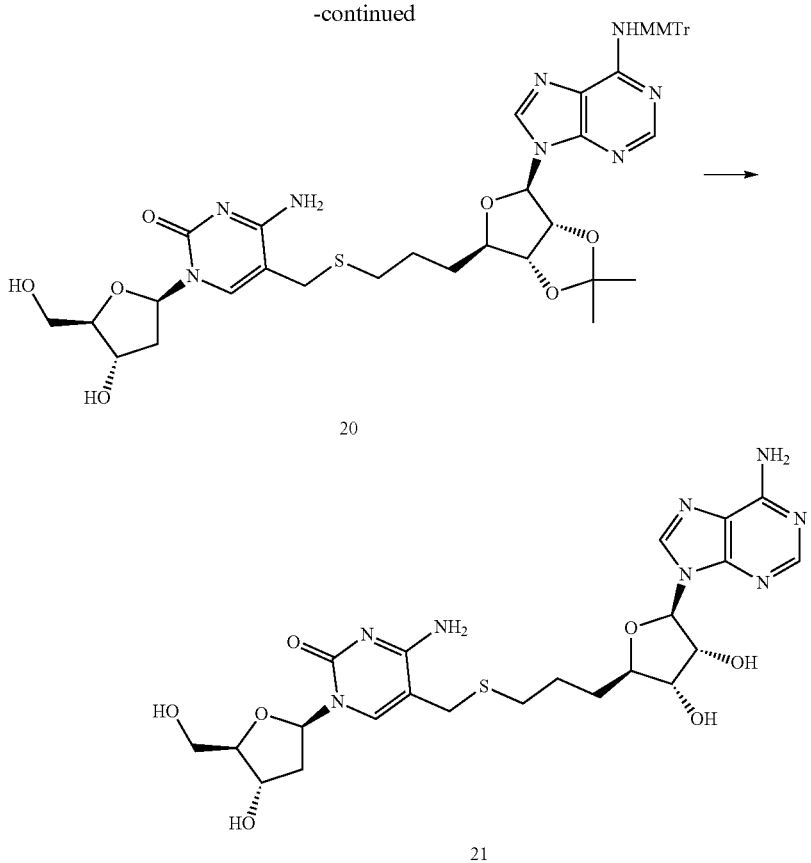

Sodium methoxide (0.20 mL of a 30% solution in methanol, 1.10 mmol) was added to a solution of 17 (0.600 g, 1.10 mmol) (Bornemann, B.; Marx, A., Bioorg. & Med. Chem. 2006, 14 (18), 6235-6238) in dry methanol (12 mL) and the reaction was stirred at room temperature under argon for 30 minutes. The reaction mixture was concentrated in vacuo then 16 (0.755 g, 1.10 mmol) followed by N,N-dimethylformamide (3 mL) and the reaction was stirred at 40° C. under argon for 3 hours. The reaction mixture was diluted with ethyl acetate (200 mL), washed with saturated aqueous sodium bicarbonate (100 mL), saturated aqueous brine (2×100 mL), then filtered and dried over anhydrous magnesium sulfate. The organic layer was concentrated in vacuo and the residue purified by silica gel flash column chromatography eluting with an ethyl acetate-petroleum ether gradient to give 1-((2R,4S,5R)-4-((tert-butyldimethylsilyl)oxy)-5-(((tert-butyldimethylsilyl)oxy)methyl)tetrahydrofuran-2-yl)-5-(((3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)propyl)thio)methyl)pyrimidine-2,4(1H,3H)-dione 18 (0.304 g, 0.28 mmol, 25% yield) as a pale yellow foam. $R_f$=0.20 (40% ethyl acetate/petroleum ether). $^1$H NMR (500 MHz, CDCl$_3$) δ8.61 (s, 1H), 8.05 (s, 1H), 7.87 (s, 1H), 7.58 (s, 1H), 7.42-7.10 (m, 12H), 6.96 (s, 1H), 6.79 (d, J=8.9 Hz, 2H), 6.27 (dd, J=8.0, 5.7 Hz, 1H), 6.00 (d, J=2.7 Hz, 1H), 5.39 (dd, J=6.6, 2.7 Hz, 1H), 4.76 (dd, J=6.6, 4.0 Hz, 1H), 4.47-4.33 (m, 1H), 4.13 (td, J=6.9, 4.0 Hz, 1H), 3.94 (q, J=3.0 Hz, 1H), 3.85-3.68 (m, 5H), 3.39 (q, J=14.0 Hz, 2H), 2.54 (td, J=7.0, 2.3 Hz, 2H), 2.27 (ddd, J=13.2, 5.8, 2.5 Hz, 1H), 1.99 (ddd, J=13.5, 8.0, 5.9 Hz, 1H), 1.85-1.62 (m, 4H), 1.58 (s, 3H), 1.35 (s, 3H), 0.98-0.80 (m, 18H), 0.16-0.02 (m, 12H). $^{13}$C NMR (126 MHz, CDCl$_3$) δ162.43, 158.30, 154.17, 152.48, 149.76, 148.38, 145.21, 138.91, 137.24, 137.15, 130.22, 128.91, 127.82, 126.80, 121.45, 114.78, 113.14, 112.35, 89.90, 87.96, 86.01, 85.26, 84.02, 83.98, 72.40, 71.02, 63.13, 55.20, 41.28, 32.42, 32.24, 27.59, 27.20, 25.98, 25.75, 25.47, 25.41, 18.43, 18.00, −4.65, −4.81, −5.29, −5.38. HRMS (m/z) calcd. for $C_{57}H_{78}N_7O_9SSi_2$ [M+H]$^+$ 1092.5120, found 1092.5117.

p-Toluenesulfonyl chloride (0.175 g, 0.908 mmol) was added to a solution of 18 (0.248 g, 0.227 mmol) and N-methylpiperidine (0.223 mL, 1.82 mmol) in dry acetonitrile (10 mL) and the reaction was stirred at room temperature under argon for 2 hours. The reaction was cooled on an ice-bath then 28% aqueous ammonia (2.5 mL) was added dropwise. The cooling bath was removed and the reaction stirred at room temperature for 2.5 hours. The reaction mixture was diluted with ethyl acetate (100 mL), washed with saturated aqueous brine (2×50 mL), then filtered and dried over anhydrous magnesium sulfate. The organic layer was concentrated in vacuo and the residue purified by silica gel flash column chromatography eluting with a methanol—ethyl acetate gradient to give 4-amino-1-((2R,4S,5R)-4-((tert-butyldimethylsilyl)oxy)-5-(((tert-butyldimethylsilyl)oxy)methyl)tetrahydrofuran-2-yl)-5-(((3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)propyl)thio)methyl)pyrimidin-2(1H)-one 19 (0.131 g, 0.120 mmol, 53% yield) as a white foam. $R_f$=0.58 (100% ethyl acetate). $^1$H NMR (500 MHz, CDCl$_3$) δ8.04 (s, 1H), 7.84 (s, 1H), 7.64 (s, 1H), 7.39-7.15 (m, 13H), 6.92 (s, 1H), 6.79 (d, J=8.9 Hz, 2H), 6.26 (t, J=6.5 Hz, 1H), 5.99 (d, J=2.5 Hz, 1H), 5.43 (dd, J=6.6, 2.6 Hz, 1H), 4.77 (dd, J=6.6, 4.1 Hz, 1H), 4.34 (dt, J=6.4, 3.3 Hz, 1H), 4.11 (ddd, J=7.6, 6.2, 4.1 Hz, 1H), 3.94 (q, J=3.1 Hz, 1H), 3.84 (dd, J=11.3, 3.2 Hz, 1H), 3.77 (s, 3H), 3.75 (dd, J=11.3, 3.0 Hz, 1H), 3.41 (d, J=1.5 Hz, 2H), 2.52-2.37 (m, 3H), 1.94 (dt, J=13.3, 6.6 Hz, 1H), 1.76 (h, J=7.4, 6.9 Hz, 2H), 1.71-1.61 (m, 2H), 1.58 (s, 3H), 1.35 (s, 3H), 0.98 0.80 (m, 18H), 0.15 0.02 (m, 12H); $^{13}$C NMR (126 MHz, CDCl$_3$) δ164.65, 158.34, 155.35, 154.19, 152.46, 148.32, 145.16, 139.80, 139.06, 137.21, 130.18, 128.88, 127.86, 126.85, 121.53, 114.79, 113.16, 100.53, 89.96, 87.79, 86.31, 85.97, 84.02, 83.89, 71.91, 71.02, 62.88, 55.21, 42.23, 32.33, 31.17, 30.59, 27.20, 25.98, 25.76, 25.39, 25.24, 18.41, 17.98, −4.56, −4.87, −5.29, −5.31. HRMS (m/z) calcd. for C$_{57}$H$_{79}$N$_8$O$_8$SSi$_2$ [M+H]$^+$ 1091.5280, found 1091.5278.

Tetrabutylammonium fluoride (0.290 mL of a 1M solution in tetrahydrofuran, 0.287 mmol) was added to a solution of 19 (0.136 g, 0.117 mmol) in dry tetrahydrofuran (5 mL), the reaction was stirred at room temperature for 1 hour until TLC showed the reaction was complete. The reaction mixture was concentrated in vacuo and purified by silica gel flash column chromatography eluting with a methanol ethyl acetate gradient to give 4-amino-1-((2R,4S,5R)-4-hydroxy-5-(hydroxymethyl)tetrahydrofuran-2-yl)-5-(((3-((3aR,4R,6R,6aR)-6-(6-(((4-methoxyphenyl)diphenylmethyl)amino)-9H-purin-9-yl)-2,2-dimethyltetrahydrofuro[3,4-d][1,3]dioxol-4-yl)propyl)thio)methyl)pyrimidin-2(1H)-one 20 (0.101 g, 94% yield) as a white foam. R$_f$=0.46 (10% ethanol/ethyl acetate). $^1$H NMR (500 MHz, MeOD) δ8.25 (s, 1H), 7.97 (s, 1H), 7.91 (s, 1H), 7.39 7.10 (m, 12H), 6.78 (d, J=9.0 Hz, 2H), 6.21 (t, J=6.4 Hz, 1H), 6.10 (d, J=2.4 Hz, 1H), 5.46 (dd, J=6.4, 2.5 Hz, 1H), 4.87-4.78 (m, 1H), 4.35 (dt, J=6.3, 3.9 Hz, 1H), 4.13 (td, J=7.1, 3.5 Hz, 1H), 3.92 (q, J=3.5 Hz, 1H), 3.78 (dd, J=12.0, 3.2 Hz, 1H), 3.73 (s, 3H), 3.72-3.68 (m, 1H), 3.38 (d, J=3.3 Hz, 2H), 3.31 (p, J=1.7 Hz, 2H), 2.45-2.26 (m, 3H), 2.11 (dt, J=13.3, 6.4 Hz, 1H), 1.75-1.63 (m, 2H), 1.63-1.49 (m, 5H), 1.34 (s, 3H). $^{13}$C NMR (126 MHz, MeOD) δ165.93, 159.90, 157.85, 155.43, 153.19, 149.69, 146.42, 141.52, 141.39, 138.39, 131.48, 130.18, 128.72, 127.84, 121.79, 115.63, 114.03, 104.33, 91.09, 88.94, 87.74, 87.62, 85.56, 85.12, 72.38, 71.88, 62.69, 55.76, 42.28, 33.42, 31.56, 29.64, 27.48, 26.32, 25.61. HRMS (m/z) calcd. for C$_{45}$H$_{51}$N$_8$O$_8$S [M+H]$^+$ 863.3551, found 863.3552.

Hydrochloric acid (0.082 mL of a 37% solution in water, 1.00 mmol) was added to a solution of 20 (0.043 g, 0.050 mmol) in methanol (3 mL), the reaction was stirred at room temperature for 4 hours until TLC showed the reaction was complete. The reaction mixture was diluted with methanol (10 mL), neutralised with Amberlyst A26(OH) resin, filtered and concentrated in vacuo and stripped with ethyl acetate. The residue was dissolved in water (50 mL), washed with ethyl acetate (50 mL), then the aqueous layer was filtered and freeze-dried. The residue was purified by silica gel flash column chromatography eluting with a 28% aqueous ammonia—methanol—dichloromethane gradient to give 4-amino-5-(((3-((2R,3S,4R,5R)-5-(6-amino-9H-purin-9-yl)-3,4-dihydroxytetrahydrofuran-2-yl)propyl)thio)methyl)-1-((2R,4S,5R)-4-hydroxy-5-(hydroxymethyl)tetrahydrofuran-2-yl)pyrimidin-2(1H)-one 21 (0.010 g, 36% yield) as an off-white solid. R$_f$=0.07 (20% 7N methanolic ammonia/dichloromethane). $^1$H NMR (500 MHz, DMSO-d6+D$_2$O) δ8.29 (s, 1H), 8.16 (s, 1H), 7.77 (s, 1H), 6.15 (t, J=6.6 Hz, 1H), 5.84 (d, J=5.2 Hz, 1H), 4.64 (t, J=5.3 Hz, 1H), 4.22 (dt, J=6.2, 3.3 Hz, 1H), 4.03 (t, J=5.0 Hz, 1H), 3.85 (dt, J=7.9, 5.0 Hz, 1H), 3.79 (q, J=3.7 Hz, 1H), 3.70-3.50 (m, 3H), 3.45 (d, J=1.7 Hz, 2H), 2.40 (t, J=7.2 Hz, 2H), 2.14 (ddd, J=13.2, 6.1, 3.4 Hz, 1H), 2.03-1.90 (m, 1H), 1.80-1.65 (m, 2H), 1.66-1.50 (m, 2H). $^{13}$C NMR (126 MHz, DMSO-d6+D$_2$O) δ164.12, 156.27, 155.33, 153.12, 149.80, 140.32, 139.89, 119.45, 102.41, 87.94, 87.56, 85.37, 83.77, 73.55, 73.31, 70.73, 61.68, 40.75, 32.74, 30.69, 28.54, 25.54. HRMS (m/z) calcd. for C$_{22}$H$_{31}$N$_8$O$_7$S [M+H]$^+$ 551.2036, found 551.2031.

Example 4: Synthesis of (S)-2-amino-4-((3-(4-amino-1-((2S,4S,514)-4-hydroxy-5-(hydroxymethyl)tetrahydrofuran-2-yl)-2-oxo-1,2-dihydropyrimidin-5-yl)propyl)-(((2R,3S,4R,5R)-5-(6-amino-9H-purin-9-yl)-3,4-dihydroxytetrahydrofuran-2-yl)methyl)amino)butanoic acid 33

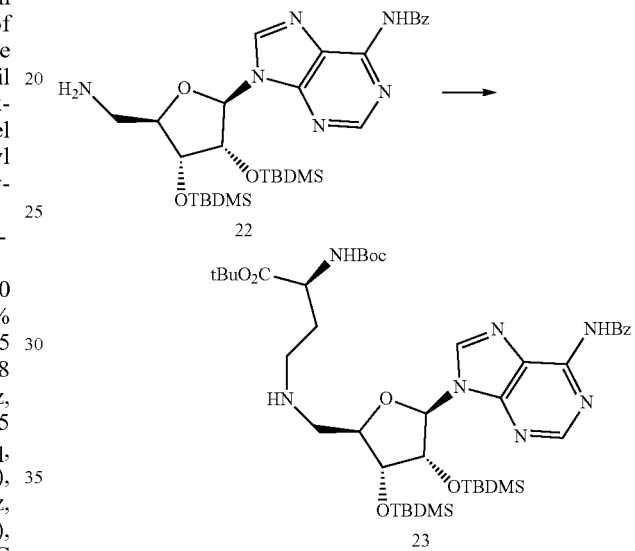

tert-Butyl L-2-((tert-butoxycarbonyl)amino)-4-oxobutanoate (Roberts, S. J., Morris, J. C., Dobson, R. J. C., Baxter, C. L., Gerrard, J. A., ARKIVOC 2004, 166-177; http://hdl.handle.net/2440/34486) (490 mg, 1.82 mmol, 1 equiv.) was added to a solution of 5'-amino-N-benzoyl-5'-deoxy-2',3'-bis-O-[(1,1-dimethylethyl)dimethylsilyl] adenosine 22 (1.11 g, 1.80 mmol) (Kojima, N., Szabo, I. E., Bruice, T. C., Tetrahedron. 2002, 58 (5), 867-879) in dry methanol (10 mL) and the reaction stirred for 5 minutes. 2-Picoline borane complex (411 mg, 1.83 mmol, 2 equiv.) was added and the reaction mixture stirred at room temperature. After 2 hours, the mixture was concentrated, then diluted with ethyl acetate (100 mL), washed with saturated aqueous sodium bicarbonate (100 mL), dried over anhydrous magnesium sulfate and filtered. The concentrated residue was purified by silica gel flash chromatography eluting with a petroleum ether-ethyl acetate gradient to give tert-butyl (S)-4-((((2R,3R,4R,5R)-5-(6-benzamido-9H-purin-9-yl)-3,4-bis((tert butyldimethylsilyl)oxy)tetrahydrofuran-2-yl)methyl)amino)-2-((tert-butoxycarbonyl)amino) butanoate 23 (858 mg, 56% yield) as a white foam. R$_f$=0.30 (60% ethyl acetate/petroleum ether). $^1$H NMR (500 MHz, CDCl$_3$) δ9.05 (s, 1H), 8.67 (s, 1H), 8.06 (s, 1H), 7.98-7.86 (m, 2H), 7.55-7.45 (m, 1H), 7.40 (dd, J=8.4, 7.0 Hz, 2H), 5.81 (d, J=5.9 Hz, 1H), 5.26 (d, J=8.4 Hz, 1H), 4.88 (t, J=5.1 Hz, 1H), 4.17 (dd, J=4.5, 3.0 Hz, 1H), 4.14-4.08 (m, 1H), 2.85 (dd, J=12.6, 3.4 Hz, 1H), 2.77 (dd, J=12.5, 6.2 Hz, 1H), 2.66 (ddd, J=12.4, 7.4, 5.3 Hz, 1H), 2.59 (dt, J=11.9, 7.4 Hz, 1H), 1.90-1.86 (m, 1H), 1.69-1.62 (m, 1H), 1.33 (s, 9H), 1.31 (s, 9H), 0.82 (s, 9H), 0.80-0.72 (m, 2H), 0.66 (s, 9H), 0.00 (s, 6H), −0.18 (s, 3H), −0.47 (s, 3H). $^{13}$C NMR (126 MHz, CDCl$_3$) δ171.92, 164.51, 155.48, 152.46, 151.41, 149.78, 142.96, 133.72, 132.72, 128.82, 127.87, 123.91, 89.84, 85.49, 81.82, 79.50, 74.23, 73.65, 52.42, 51.24, 46.04, 33.25, 28.32, 28.01, 25.84, 25.67, 18.04, 17.82, −4.43, −4.60, −4.64, −5.19. HRMS (m/z) calcd. for C$_{42}$H$_{69}$N$_7$O$_8$Si$_2$ [M+Na]$^+$ 856.4824, found 856.4824.
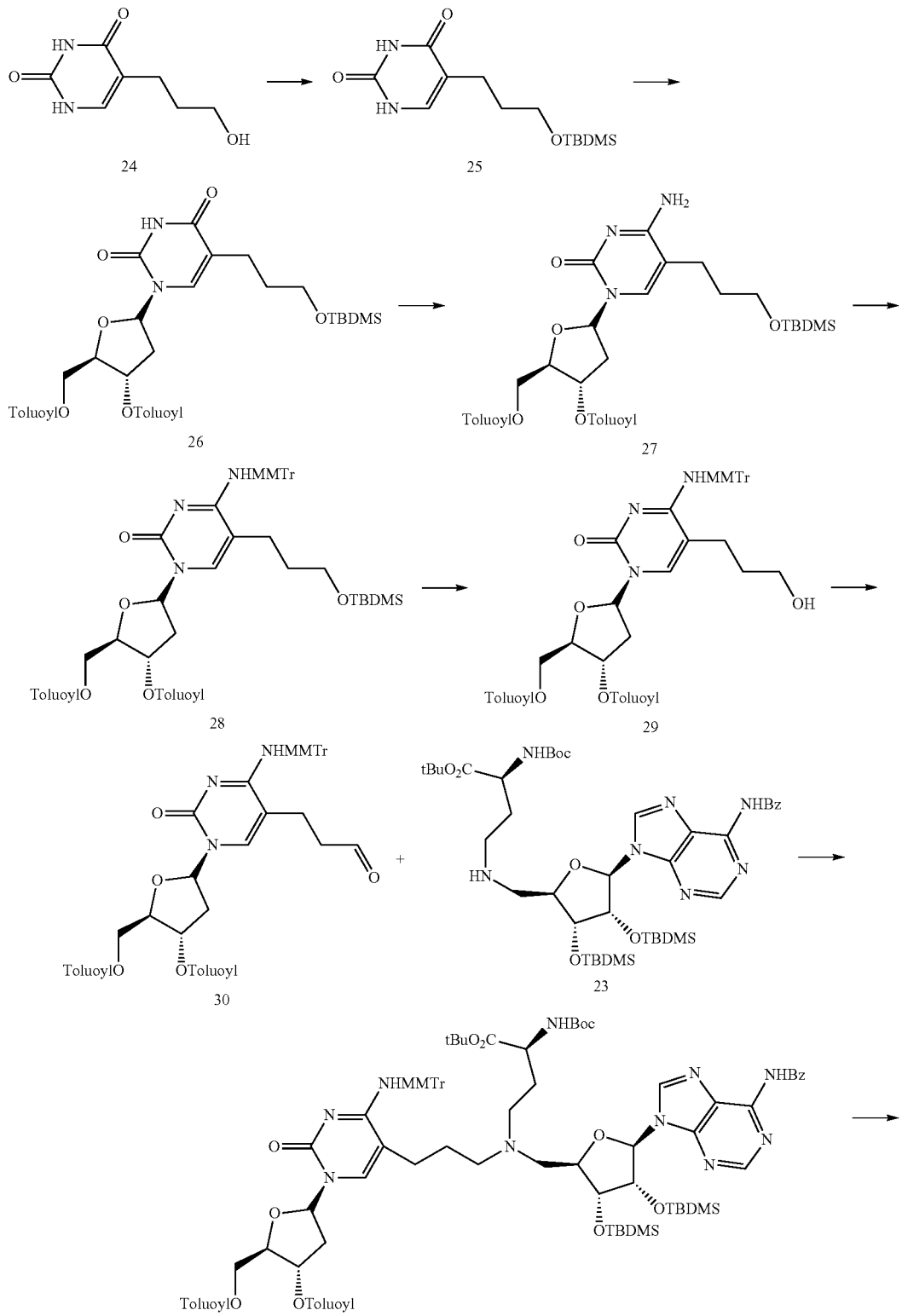

-continued

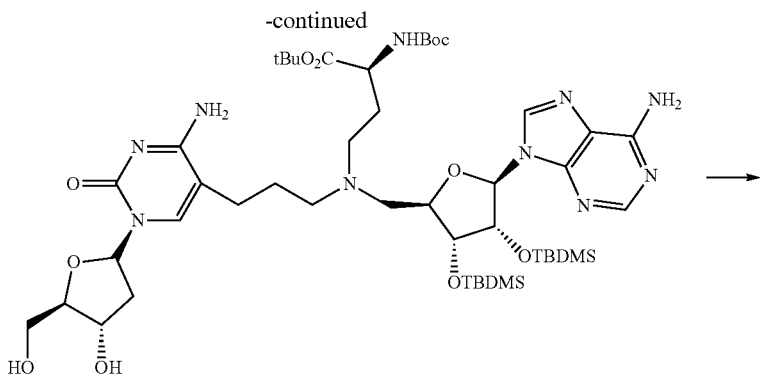

32

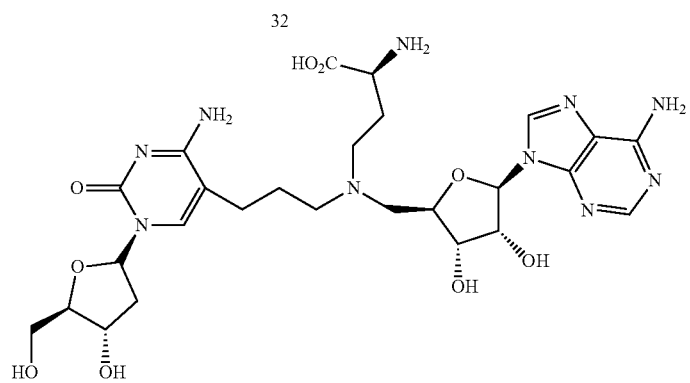

33

5-(3-hydroxypropyl) uracil 24 (Denny, G. H., Ryder, M. A., J. Med. Chem., 1974, 17 (11), 1230-1231) (3.15 g, 18.51 mmol), imidazole (3.81 g, 55.53 mmol) and tert-butyldimethylsilyl chloride (1.89 g, 12.4 mmol) were placed in a round bottom flask. Dry dimethylformamide (31 mL) was added and the mixture was stirred at room temperature under argon for 3 hours. The reaction mixture was then diluted with ethyl acetate (150 mL), washed twice with water (2×100 mL). The organic layer was dried over magnesium sulfate, filtered and concentrated. A white solid of 5-(3-((tert-butyldimethylsilyl)oxy)propyl)pyrimidine-2,4(1H, 3H)-dione 25 was obtained (4.80 g, 91%). $R_f$=0.32 (ethyl acetate/petroleum ether, 5/1). $^1$H NMR $^1$H NMR (500 MHz, Methanol-$d_4$) δ7.11 (s, 1H), 3.60 (t, J=6.2 Hz, 2H), 2.28 (td, J=7.5, 1.0 Hz, 2H), 1.80-1.60 (m, 2H), 0.84 (s, 9H), 0.00 (s, 6H). δ167.05, 153.70, 139.40, 114.45, 63.62, 32.39, 26.48, 24.18, 19.18, −5.11. HRMS (m/z) calcd. for $C_{13}H_{25}N_2O_3Si$ [M+H]$^+$ 285.1634, found 285.1632.

Compound 25 was suspended in hexamethyldisilazane (2.65 mL, 12.30 mmol) and chlorotrimethylsilane (460 μL, 3.50 mmol). The reaction mixture was heated under reflux during 2 hours then concentrated under high vacuum. The residue obtained was dissolved in dry dichloromethane (10 mL) under argon. Then, 1-chloro-3,5-di-O-toluoyl-2-deoxy-D-ribofuranose (Rolland, V., Kotera, M., Lhomme, J. Synth. Commun., 1997, 27 (20), 3505-3511) (700 mg, 1.81 mmol) and trimethylsilyl trifluoromethanesulfonate (20 μL, 0.09 mmol) were added at 0° C. After 30 minutes of stirring, the reaction mixture was allowed to warm to room temperature and stirred for another hour. The organic layer was then washed with water (10 mL), saturated aqueous sodium bicarbonate (10 mL), dried over magnesium sulfate, filtered and concentrated. The residue was purified by silica gel flash chromatography eluting with a petroleum ether-ethyl acetate gradient to give the major (β-anomer (2R,3S,5S)-5-(5-(3-((tert-butyldimethylsilyl)oxy)propyl)-2,4-dioxo-3,4-dihydropyrimidin-1(2H)-yl)-2-(((4-methylbenzoyl)oxy)methyl) tetrahydrofuran-3-yl4-methylbenzoate 26 (601 mg, 54% yield) as a white solid. $R_f$=0.57 (ethyl acetate/petroleum ether, 1/1). $^1$H NMR (500 MHz, CDCl$_3$) 9.86 (s, 1H), 7.92 (dd, J=14.7, 8.2 Hz, 4H), 7.38-7.17 (m, 5H), 6.42 (dd, J=8.8, 5.5 Hz, 1H), 5.61 (d, J=6.6 Hz, 1H), 4.69 (qd, J=12.2, 3.5 Hz, 2H), 4.56-4.48 (m, 1H), 3.47 (t, J=6.2 Hz, 2H), 2.71 (ddd, J=14.3, 5.6, 1.6 Hz, 1H), 2.39 (d, J=3.6 Hz, 6H), 2.20 (dt, J=15.1, 7.7 Hz, 1H), 2.12 (dt, J=14.8, 7.5 Hz, 1H), 1.74-1.50 (m, 2H), 0.85 (s, 9H), 0.00 (d, J=1.8 Hz, 6H). $^{13}$C NMR (126 MHz, CDCl$_3$) δ166.04, 165.95, 163.47, 150.57, 144.40, 144.31, 129.83, 129.55, 129.37, 129.23, 85.27, 82.79, 74.96, 64.27, 62.36, 38.03, 31.34, 25.92, 23.67, 21.68, 21.65, 18.25, −5.33. HRMS (m/z) calcd. for $C_{34}H_{45}N_2O_8Si$ [M+H]$^+$ 637.2945, found 637.2953.

Compound 26 (253 mg, 0.39 mmol), N-methylpiperidine (390 μL, 3.18 mmol), and p-toluenesulfonyl chloride (306 mg, 1.59 mmol), were dissolved in dry acetonitrile (10 mL). The reaction mixture was stirred at room temperature under argon for 4 hours. Then the reaction mixture was cooled in ice bath and 28% aqueous ammonia (5 mL) was added dropwise. After 30 minutes the mixture was allowed to warm to room temperature and stirred for another 2 hours. The reaction mixture was diluted in ethyl acetate. The organic layer was washed with brine (15 mL), dried over magnesium sulfate, filtered and concentrated. The residue was purified by silica gel flash chromatography eluting with a petroleum ether-ethyl acetate gradient followed by ethyl acetate-methanol gradient to give (2R,3S,5S)-5-(4-amino-5-(3-((tert-butyldimethylsilyl)oxy)propyl)-2-oxopyrimidin-1 (2H)-yl)-2-(((4-methylbenzoyl)oxy)methyl)tetrahydrofuran-3-yl4-methylbenzoate 27 (111 mg, 44% yield) as a white foam. $R_f$=0.05 (ethyl acetate/petroleum ether, 1/1). $^1$H NMR (500 MHz, CDCl$_3$) 7.89 (d, J=8.3 Hz, 2H), 7.83 (d, J=8.3 Hz, 2H), 7.33 (s, 1H), 7.22-7.14 (m, 6H), 6.40 (dd, J=8.6, 5.4 Hz, 1H), 5.56-5.54 (m, 1H), 4.74 (dd, J=12.1, 3.0 Hz, 1H), 4.56 (dd, J=12.1, 3.7 Hz, 1H), 4.49 (td, J=3.3, 2.0 Hz, 1H), 3.49 3.41 (m, 2H), 2.87 (ddd, J=14.5, 5.5, 1.5 Hz, 1H), 2.37 (s, 3H), 2.35 (s, 3H), 2.16 (ddd, J=14.7, 8.6, 6.6 Hz, 1H), 2.07 (h, J=7.8 Hz, 2H), 1.46-1.37 (m, 3H), 0.83 (s, 9H), 0.00 (s, 6H). $^{13}$C NMR (126 MHz, CDCl$_3$) δ166.20, 166.04, 165.30, 155.49, 144.41, 144.33, 137.62, 129.85, 129.71, 129.56, 129.36, 129.32, 129.24, 126.69, 126.43, 106.14, 86.57, 83.07, 75.36, 64.39, 61.32, 39.08, 31.67, 25.88, 23.10, 21.71, 21.66, 18.27, −5.40. HRMS (m/z) calcd. for C$_{34}$H$_{46}$N$_3$O$_7$Si [M+H]$^+$ 636.3105, found 636.3096.

To a solution of 27 (90 mg, 0.15 mmol) in dichloromethane (3 mL) were added silver nitrate (72 mg, 0.43 mmol), sym-collidine (57 μL, 0.43 mmol) and 4-methoxytrityl chloride (135 mg, 0.43 mmol). The reaction mixture was stirred at room temperature under argon overnight. The precipitate was filtered through celite and the filtrate diluted with dichloromethane (15 mL). The organic layer was then washed with 5M citric acid (10 mL), sodium bicarbonate (10 mL), brine (10 mL), dried over magnesium sulfate, filtered and concentrated. The residue was purified by silica gel flash chromatography eluting with a petroleum ether-ethyl acetate gradient to give (2R,3S,5S)-5-(5-(3-((tert-butyldimethylsilyl)oxy)propyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 28 (110 mg, 86% yield) as a pale yellow foam. $R_f$=0.18 (ethyl acetate/petroleum ether, 2/1). $^1$H NMR (500 MHz, CDCl$_3$) δ7.93 (dd, J=8.3, 1.3 Hz, 4H), 7.33-7.17 (m, 17H), 6.80 (d, J=9.0 Hz, 2H), 6.41 (dd, J=8.8, 5.3 Hz, 1H), 6.12 (s, 1H), 5.58 (dt, J=6.7, 1.8 Hz, 1H), 4.77 (dd, J=12.0, 3.0 Hz, 1H), 4.60 (dd, J=12.1, 4.0 Hz, 1H), 4.48 (td, J=3.7, 2.6 Hz, 1H), 3.78 (s, 3H), 3.48 (t, J=5.8 Hz, 2H), 2.78 (ddd, J=14.3, 5.4, 1.5 Hz, 1H), 2.43 (s, 3H), 2.42 (s, 3H), 2.28-2.19 (m, 3H), 2.18-2.12 (m, 1H), 1.96 (s, 1H), 1.61-1.51 (m, 2H), 0.86 (s, 9H), 0.00 (s, 3H), −0.00 (s, 3H). $^{13}$C NMR (126 MHz, CDCl$_3$) δ166.16, 166.02, 161.56, 158.24, 154.43, 144.74, 144.34, 144.24, 136.75, 135.81, 130.16, 129.82, 129.63, 129.35, 129.22, 128.66, 127.88, 126.81, 126.76, 126.48, 113.17, 106.72, 85.95, 82.53, 75.17, 71.09, 64.44, 61.89, 55.15, 38.67, 31.32, 25.92, 24.27, 21.70, −5.33. HRMS (m/z) calcd. for C$_{54}$H$_{62}$N$_3$O$_8$Si [M+H]$^+$ 908.4306, found 908.4310.

Tetrabutylammonium fluoride (300 μL of a 1M solution in tetrahydrofuran, 0.29 mmol) was added to a solution of 28 (135 mg, 0.15 mmol) in dry tetrahydrofuran (4 mL), the reaction was stirred at room temperature for 4 hours until TLC showed the reaction was complete. The reaction mixture was concentrated in vacuo and diluted with chloroform (15 mL). The organic layer was washed twice with water (10 mL), dried over magnesium sulfate, filtered and concentrated. The residue was then purified by silica gel flash column chromatography eluting with a petroleum ether ethyl acetate gradient to give (2R,3S,5S)-5-(5-(3-hydroxypropyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 29 (83 mg, 71% yield) as a yellow syrup. $R_f$=0.14 (ethyl acetate/petroleum ether, 1/1). $^1$H NMR (500 MHz, CDCl$_3$) δ7.92 (dd, J=10.0, 7.9 Hz, 4H), 7.43 7.14 (m, 18H), 6.85-6.74 (m, 2H), 6.63 (s, 1H), 6.37 (dd, J=8.5, 5.4 Hz, 1H), 5.56 (d, J=6.5 Hz, 1H), 4.78 (d, J=3.1 Hz, 1H), 4.59 (dd, J=12.1, 4.2 Hz, 1H), 4.47 4.40 (m, 1H), 3.74 (s, 3H), 3.45 (m, 1H), 2.73 (dd, J=14.4, 5.4 Hz, 1H), 2.40 (s, 3H), 2.41 (s, 3H), 2.24 (m, 2H), 2.19 2.11 (m, 1H), 1.61-1.47 (m, 2H). $^{13}$C NMR (126 MHz, CDCl$_3$) δ171.14, 166.20, 161.76, 158.17, 154.52, 144.69, 144.39, 136.74, 136.40, 130.27, 129.81, 129.66, 129.39, 129.23, 128.75, 128.65, 127.74, 126.76, 126.67, 126.42, 113.02, 106.82, 85.87, 82.56, 75.06, 71.08, 64.34, 60.25, 55.15, 38.57, 31.43, 23.35, 21.69. HRMS (m/z) calcd. for C$_{48}$H$_{48}$N$_3$O$_8$ [M+H]$^+$ 794.3437, found 794.3441.

Dess-Martin periodinane (100 mg, 0.24 mmol) was added to a solution of 29 (92 mg, 0.13 mmol) in dry dichloromethane (3 mL) at 0° C. The reaction mixture was stirred under argon for 30 minutes. Then the reaction mixture was allowed to warm to room temperature and stirred for another 30 minutes until TLC showed the reaction was complete. The precipitate was filtered over celite, washed three times with dichloromethane (5 mL) and concentrated. The residue was then engaged into to next step without further purification. The aldehyde 30 obtained was dissolved in dry methanol (3 mL) and a solution of 23 (94 mg, 0.13 mmol) in dry methanol (3 mL) was added. 2-picoline borane complex (22 mg, 0.21 mmol) was added and the mixture stirred at room temperature under argon for 5 hours. The reaction mixture had a pH-5-6. 2-picoline borane complex (22 mg, 0.21 mmol) was added again and the mixture stirred at room temperature under argon overnight. Then the reaction mixture was concentrated, diluted in chloroform (10 mL), washed with saturated aqueous sodium bicarbonate (5 mL), dried over magnesium sulfate, filtered and concentrated. The residue was then purified by silica gel flash column chromatography eluting with a petroleum ether ethyl acetate gradient to give (2R,3S,5S)-5-(5-(3-((((2R,3R,4R,5R)-5-(6-benzamido-9H-purin-9-yl)-3,4-bis((tert-butyldimethylsilyl)oxy)tetrahydrofuran-2-yl)methyl)((S)-4-(tert-butoxy)-3-((tert-butoxycarbonyl)amino)-4-oxobutyl)amino)propyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 31 (50 mg, 27% yield) as a white foam. $R_f$=0.40 (ethyl acetate/petroleum ether, 1/1). $^1$H NMR (500 MHz, CDCl$_3$) δ9.18 (s, 1H), 8.61 (s, 1H), 8.11-7.86 (m, 4H), 7.77 (dd, J=8.1, 5.8 Hz, 4H), 7.50-7.29 (m, 3H), 7.17-7.00 (m, 18H), 6.65 (d, J=9.0 Hz, 2H), 6.30 (dd, J=8.6, 5.4 Hz, 1H), 5.89 (s, 1H), 5.78 (d, J=5.3 Hz, 1H), 5.53-5.34 (m, 1H), 5.17 (s, 1H), 4.96 (s, 1H), 4.65 (d, J=12.1 Hz, 1H), 4.46 (d, J=12.2 Hz, 1H), 4.36 (s, 1H), 4.14-4.01 (m, 4H), 3.62 (s, 3H), 2.87-2.73 (m, 1H), 2.63 (d, J=10.6 Hz, 2H), 2.42 (t, J=7.3 Hz, 2H), 2.29 (s, 6H), 2.27 (s, 3H), 2.07-2.01 (m, 1H), 1.92 (d, J=5.7 Hz, 2H), 1.81-1.71 (m, 2H), 1.55-1.48 (m, 1H), 1.48-1.40 (m, 1H), 1.31 (s, 9H), 1.28 (s, 10H), 0.83 (s, 9H), 0.82-0.74 (m, 3H), 0.69 (s, 9H), 0.01 (s, 3H), 0.00 (s, 3H), −0.15 (s, 3H), −0.38 (s, 3H). $^{13}$C NMR (126 MHz, CDCl$_3$) δ171.56, 166.12, 164.75, 161.43, 158.23, 155.47, 154.73, 152.39, 151.48, 149.98, 144.72, 144.28, 144.20, 142.84, 136.60, 135.92, 133.54, 132.55, 130.11, 129.80, 129.65, 129.32, 129.17, 128.64, 128.18, 127.87, 126.78, 126.46, 124.16, 113.18, 106.46, 90.04, 86.26, 83.84, 82.62, 81.76, 79.56, 75.15, 74.47, 73.65, 71.14, 64.37, 60.36, 56.49, 55.15, 53.95, 52.90, 50.81, 40.90, 38.57, 29.62, 28.34, 28.01, 25.85, 25.71, 23.86, 21.68, 18.04, 17.86, 14.63, 14.19, −0.02, −4.31, −4.44, −4.56, −4.90. HRMS (m/z) calcd. for C$_{90}$H$_{115}$N$_{10}$O$_{15}$Si$_2$ [M+H]$^+$ 1631.8082, found 1631.8075.

A catalytic amount of sodium was added to dry methanol (1.5 mL). After it was all consumed, 31 (33 mg, 0.024 mmol) was added and the reaction mixture stirred at room temperature under argon for 3 hours. Then, resin ion exchange Dowex 50WX8-H$^+$ (160 mg) was added and the reaction mixture stirred slowly at room temperature for 20 minutes (until pH 7 was reached). The resin was filtered, washed with methanol and the filtrate concentrated. TLC showed two products meaning that the deprotection was incomplete. Thus, the residue was dissolved in 7N ammonia in methanol (2 mL) and the reaction mixture stirred at room temperature under argon overnight. The reaction mixture was then concentrated and purified by silica gel flash column chromatography eluting with a dichloromethane-methanol gradient to give tert-butyl (S)-4-((3-(4-amino-1-((2S,4S,5R)-4-hydroxy-5-(hydroxymethyl)tetrahydrofuran-2-yl)-2-oxo-1,2-dihydropyrimidin-5-yl)propyl)(((2R,3R,4R,5R)-5-(6-amino-9H-purin-9-yl)-3,4-bis((tert-butyldimethylsilyl)oxy)tetrahydrofuran-2-yl)methyl)amino)-2-((tert-butoxycarbonyl)amino)butanoate 32 (8 mg, 33% yield) as an colorless oil. $R_f$=0.07 (dichloromethane-methanol, 15/1). $^1$H NMR (500 MHz, MeOD) δ8.12 (s, 1H), 8.05 (s, 1H), 7.69 (s, 1H), 6.08 (t, J=6.5 Hz, 1H), 5.82 (d, J=6.4 Hz, 1H), 4.92 (m, 1H), 4.22 (dt, J=6.3, 3.8 Hz, 1H), 4.11 (br s, 1H), 4.08-4.05 (m, 1H), 3.93-3.87 (m, 1H), 3.81-3.72 (m, 2H), 3.65 (dd, J=12.0, 3.2 Hz, 1H), 3.57 (dd, J=12.0, 3.5 Hz, 1H), 2.86 (m, 1H), 2.76 (dd, J=14.0, 3.9 Hz, 1H), 2.53-2.41 (m, 3H), 2.39-2.37 (m, 1H), 2.25-2.08 (m, 3H), 2.04-1.95 (m, 1H), 1.86-1.77 (m, 1H), 1.62-1.50 (m, 4H), 1.27 (s, 9H), 1.24 (s, 9H), 0.82 (s, 9H), 0.61 (s, 9H), 0.02 (s, 3H), 0.00 (s, 3H), −0.20 (s, 3H), −0.49 (s, 3H). $^{13}$C NMR (126 MHz, MeOD) δ172.16, 165.20, 156.49, 155.99, 152.46, 149.32, 141.11, 138.70, 119.70, 106.61, 88.96, 87.46, 86.27, 84.31, 81.23, 79.08, 74.58, 73.76, 70.54, 63.34, 61.31, 56.34, 53.55, 53.04, 50.88, 40.75, 28.34, 27.37, 26.92, 25.29, 25.08, 24.84, 24.34, 23.84, 17.56, 17.34, −1.46, −5.39, −5.45, −5.69, −6.40. HRMS (m/z) calcd. for $C_{47}H_{83}N_{10}O_{11}Si_2$ [M+H]$^+$ 1019.5781, found 1019.5789.

Tetrabutylammonium fluoride (16 µL of a 1M solution in tetrahydrofuran, 0.016 mmol) and acetic acid (2 µL, 0.020 mmol) were added to a solution of 32 (8 mg, 0.008 mmol) in dry tetrahydrofuran (1 mL). The reaction was stirred at room temperature for 4 hours until TLC showed the reaction was complete. The reaction mixture was concentrated in vacuo and then diluted in a 1:1 mixture of 1,4-dioxane/water (2 mL). Resin ion exchange Dowex 50WX8-H$^+$ (200 mg) was added and the reaction mixture stirred slowly at room temperature overnight. Filtration of the resin was followed by several washing with aqueous ammonia 0.2N and concentrated. The residue was then purified using HPLC: Column=2.7 µm Synergy® Fusion-RP 3×50 mm, Flow=0.5 mL/min; Sample=1 mg/mL in water; Injection volume=1 µL; Solvent A=water+TEEAc; Solvent B=MeCN; Gradient=5-25% B; Wavelength 254 nm. (S)-2-amino-4-((3-(4-amino-1-((2S,4S,5R)-4-hydroxy-5-(hydroxymethyl)tetrahydrofuran-2-yl)-2-oxo-1,2-dihydropyrimidin-5-yl)propyl)(((2R,3S,4R,5R)-5-(6-amino-9H-purin-9-yl)-3,4-dihydroxytetrahydrofuran-2-yl)methyl)amino)butanoic acid 33 (1.5 mg, 31% yield) was obtained as a white solid after freeze-drying. $^1$H NMR (500 MHz, D$_2$O) δ8.36 (s, 1H), 8.30 (s, 1H), 7.74 (s, 1H), 6.18 (t, J=6.3 Hz, 1H), 6.10 (d, J=4.5 Hz, 1H), 4.92 (d, J=4.8 Hz, 1H), 4.52 (d, J=2.7 Hz, 1H), 4.42 (dt, J=6.8, 4.3 Hz, 1H), 4.07 (td, J=4.3, 3.2 Hz, 1H), 3.90 (d, J=5.5 Hz, 1H), 3.84 (m, 2H), 3.78-3.71 (m, 2H), 3.57-3.53 (m, 2H), 3.43-3.35 (m, 2H), 2.45 (ddd, J=14.1, 6.5, 4.5 Hz, 1H), 2.39 (q, J=8.4, 7.6 Hz, 1H), 2.35-2.29 (m, 1H), 2.25 (dt, J=13.1, 6.2 Hz, 1H), 2.20-2.12 (m, 1H), 1.95-1.86 (m, J=6.0 Hz, 0H), 1.84-1.75 (m, 1H). $^{13}$C NMR (126 MHz, D$_2$O) δ173.04, 160.70, 153.79, 151.14, 150.26, 148.50, 141.75, 140.21, 119.22, 118.88, 105.47, 89.54, 87.13, 86.54, 72.48, 72.07, 70.12, 60.88, 54.84, 53.08, 52.89, 39.72, 25.15, 22.73. HRMS (m/z) calcd. for $C_{26}H_{39}N_{10}O_9$ [M+H]$^+$ 635.2901, found 635.2897.

Example 5: Synthesis of (S)-2-amino-4-((2-((4-amino-1-((2S,4S,5R)-4-hydroxy-5-(hydroxymethyl)tetrahydrofuran-2-yl)-2-oxo-1,2-dihydropyrimidin-5-yl)thio)ethyl)-(((2R,3S,4R,5R)-5-(6-amino-9H-purin-9-yl)-3,4-dihydroxytetrahydrofuran-2-yl)methyl)amino)butanoic acid 42

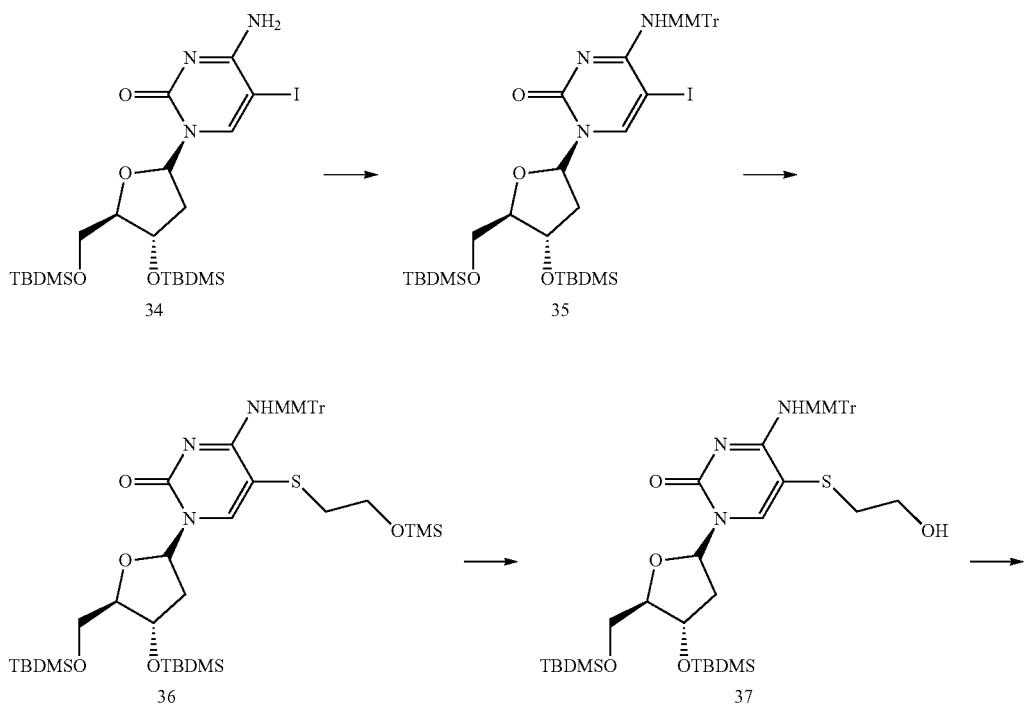

-continued
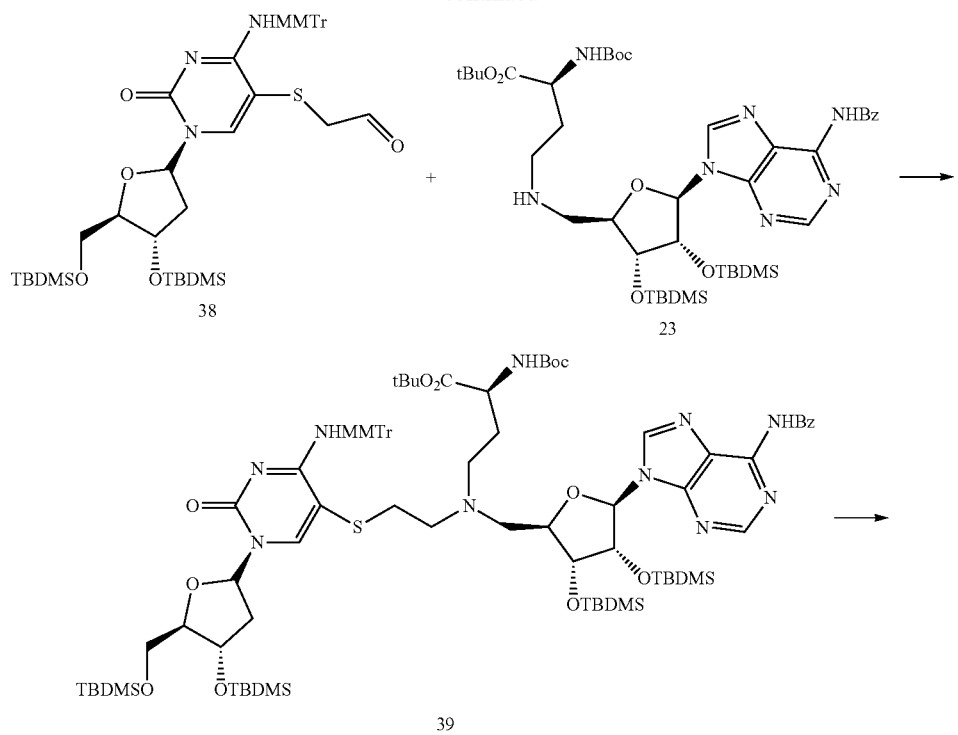
39
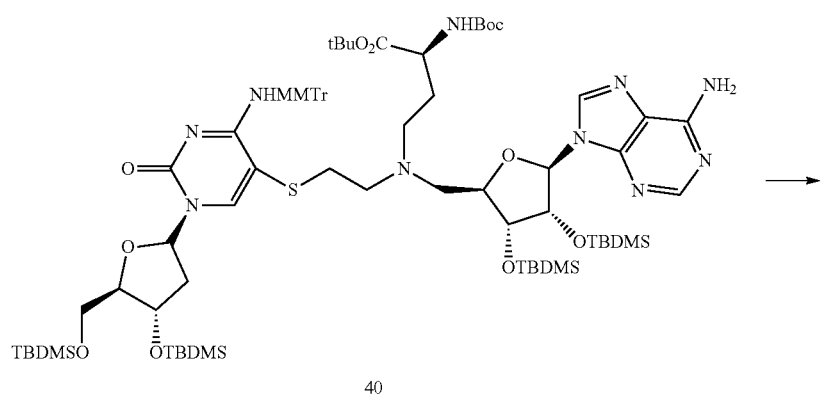
40
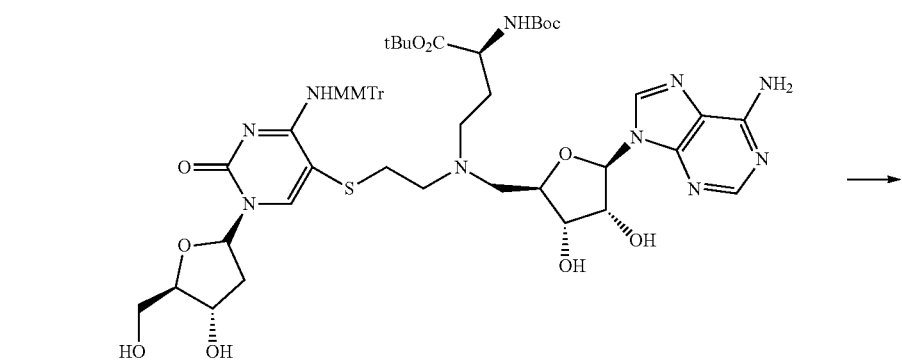
41

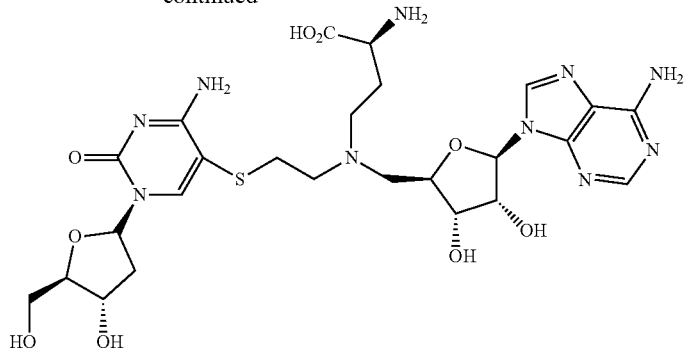

42

To a solution of 3',5'-Bis(tert-butyldimethylsilyl)-5-iodo-2'-deoxycytidine 34 (Samanta B., Seikowski, J., and Höbartner, C., Angewandte Chemie, Int. Ed. 2016, 55, 5, 1912-1916) (3.226 g, 5.55 mmol) in dichloromethane (65 mL) were added silver nitrate (1.13 g, 6.66 mmol), sym-collidine (3 mL, 22.19 mmol) and 4-methoxytrityl chloride (3.53 g, 11.09 mmol). The reaction mixture was stirred at room temperature under argon overnight. The precipitate was filtered through celite and the filtrate diluted with dichloromethane (50 mL). The organic layer was then washed with 5M citric acid (50 mL), sodium bicarbonate (50 mL), brine (50 mL), dried over magnesium sulfate, filtered and concentrated. The residue was purified by silica gel flash chromatography eluting with a petroleum ether-ethyl acetate gradient to give 1-((2S,4S,5R)-4-((tert-butyldimethylsilyl)oxy)-5-(((tert-butyldimethylsilyl)oxy)methyl)tetrahydrofuran-2-yl)-5-iodo-4-(((4-methoxyphenyl)diphenylmethyl)amino)pyrimidin-2(1H)-one 35 (3.802 g, 80% yield) as a pale yellow foam. $R_f$=0.51 (ethyl acetate/petroleum ether, 1/2). $^1$H NMR (500 MHz, CDCl$_3$) δ7.89 (s, 1H), 7.28-7.11 (m, 10H), 6.79-6.73 (m, 3H), 6.68 (s, 1H), 6.08 (dd, J=7.5, 5.8 Hz, 1H), 4.28 (dt, J=5.8, 2.8 Hz, 1H), 3.87 (q, J=2.7 Hz, 1H), 3.79 (dd, J=11.3, 2.7 Hz, 1H), 3.73 (s, 3H), 3.69 (dd, J=11.3, 2.7 Hz, 1H), 2.31 (ddd, J=13.4, 5.8, 2.8 Hz, 1H), 1.83 (ddd, J=13.5, 7.6, 6.2 Hz, 1H), 1.70 (s, 1H), 0.89 (s, 9H), 0.82 (s, 9H), 0.09 (d, J=5.6 Hz, 6H), −0.00 (d, J=1.3 Hz, 6H). $^{13}$C NMR (126 MHz, CDCl$_3$) δ159.38, 158.31, 157.39, 153.34, 145.32, 144.32, 136.33, 130.16, 128.65, 127.89, 126.86, 113.18, 87.97, 86.48, 72.34, 71.73, 62.95, 58.93, 55.17, 42.41, 25.72, 24.27, 20.76, 18.48, 17.97, −4.62, −4.89, −5.12, −5.29. HRMS (m/z) calcd. for $C_{41}H_{57}IN_3O_5Si_2$ [M+H]$^+$ 854.2882, found 854.2877.

2-hydroxyethyl disulfide (352 µL, 2.874 mmol) was dissolved in hexamethyldisilazane (1.20 mL, 5.574 mmol) and chlorotrimethylsilane (730 µL, 5.574 mmol). The reaction mixture was heated under reflux during 2 hours then concentrated under high vacuum. The residue obtained dissolved in dry THF (10 mL) under argon. To a suspension of sodium hydride (60 mass % in oil) (115 mg, 2.874 mmol) in 15 ml of dry tetrahydrofuran was added a solution of 35 (1.227 g, 1.44 mmol) in 15 ml of dry tetrahydrofuran at 0° C. After 30 minutes of stirring, the mixture was cooled at −78° C. and n-butyllithium (1.88 mol/L) in hexane (1.53 mL, 2.874 mmol) was added. The mixture was stirred for another 30 minutes and the solution of trimethyl-[2-(2-trimethylsilyloxyethyldisulfanyl)ethoxy]silane (2.874 mmol) in dry tetrahydrofuran was added. The mixture stirred from −78° C. was allowed to reach room temperature slowly over night. Then, the reaction mixture was quenched with ammonium chloride at 0° C., extracted with ethyl acetate washed with brine, dried over magnesium sulfate filtered and concentrated. The residue was purified by silica gel flash chromatography eluting with a petroleum ether-ethyl acetate gradient to give 1-((2S,4S,5R)-4-((tert-butyldimethylsilyl)oxy)-5-(((tert-butyldimethylsilyl)oxy)methyl)tetrahydrofuran-2-yl)-4-(((4-methoxyphenyl)diphenylmethyl)amino)-5-((2-((trimethylsilyl)oxy)ethyl)thio)pyrimidin-2(1H)-one 36 (448 mg, 35% yield) as a yellowish foam. $R_f$=0.80 (ethyl acetate/petroleum ether, 1/1). $^1$H NMR (500 MHz, CDCl$_3$) δ7.88 (s, 1H), 7.63 (s, 1H), 7.26-7.12 (m, 12H), 6.74 (d, J=8.9 Hz, 2H), 6.15-6.04 (m, 1H), 4.31-4.26 (m, 1H), 3.84 (d, J=3.1 Hz, 1H), 3.80 (dd, J=3.1 Hz, 1H), 3.71 (s, 3H), 3.60 (dd, J=3.1 Hz, 1H), 3.61 (t, J=6.9 Hz, 2H), 2.66 (td, J=6.7, 1.9 Hz, 2H), 2.29 (ddd, J=13.3, 6.0, 3.1 Hz, 1H), 1.83 (dt, J=13.4, 6.8 Hz, 1H), 0.87 (s, 9H), 0.81 (s, 9H), 0.08-0.06 (m, 6H), −0.01 (m, 15H). $^{13}$C NMR (126 MHz, CDCl$_3$) δ162.59, 158.78, 154.62, 146.45, 145.17, 137.16, 130.70, 129.18, 128.39, 127.31, 113.66, 99.11, 88.27, 86.72, 72.61, 71.55, 63.43, 61.80, 55.68, 42.71, 39.76, 26.60, 26.26, −0.00, −4.09, −4.35, −4.75, −4.84. HRMS (m/z) calcd. for $C_{46}H_{70}N_3O_6SSi_3$ [M+H]$^+$ 876.4293, found 876.4296.

Compound 36 (448 mg) was dissolved in methanol (10 mL) and triethylamine (500 µL) was added. The reaction mixture was stirred at room temperature for 3 hours. Then, the reaction mixture was concentrated under high vacuum and the residue purified by silica gel flash chromatography eluting with a petroleum ether-ethyl acetate gradient to give 1-((2S,4S,5R)-4-((tert-butyldimethylsilyl)oxy)-5-(((tert-butyldimethylsilyl)oxy)methyl)tetrahydrofuran-2-yl)-5-((2-hydroxyethyl)thio)-4-(((4-methoxyphenyl)diphenylmethyl)amino)pyrimidin-2(1H)-one 37 (410 mg, Quant.) as a yellowish foam. $R_f$=27 (ethyl acetate/petroleum ether, 1/1). $^1$H NMR (500 MHz, CDCl$_3$) δ7.90 (s, 1H), 7.72 (s, 1H), 7.44-7.10 (m, 12H), 6.75 (d, J=8.9 Hz, 1H), 6.10 (dd, J=7.4, 5.9 Hz, 1H), 4.29 (dt, J=6.1, 3.0 Hz, 1H), 3.85 (q, J=3.1 Hz, 1H), 3.78 (dd, J=11.3, 3.1 Hz, 1H), 3.72 (s, 3H), 3.70 (dd, J=11.3, 3.0 Hz, 1H), 3.63 (t, J=6.0 Hz, 2H), 2.71 (t, J=6.0 Hz, 2H), 2.30 (ddd, J=13.4, 5.9, 3.0 Hz, 1H), 1.84 (ddd, J=13.5, 7.4, 6.2 Hz, 1H), 1.67 (s, 1H), 0.88 (s, 9H), 0.82 (s, 9H), 0.09 (s, 3H), 0.07 (s, 3H), 0.00 (s, 6H). $^{13}$C NMR (126 MHz, CDCl$_3$) δ162.07, 158.26, 153.98, 146.26, 144.64, 136.64, 130.20, 128.70, 127.84, 126.79, 113.11, 98.01, 87.79, 86.24, 72.14, 71.08, 62.97, 60.41, 55.17, 42.16, 39.63, 26.06, 25.74, 18.45, 17.98, −4.61, −4.87, −5.28, −5.37. HRMS (m/z) calcd. for $C_{43}H_{62}N_3O_6SSi_2$ [M+H]$^+$ 804.3898, found 804.3898.

Dess-Martin periodinane (270 mg, 0.67 mmol) was added to a solution of 37 (247 mg, 0.307 mmol) in dry dichloromethane (10 mL) at 0° C. The reaction mixture was stirred under argon for 30 minutes. Then the reaction mixture was allowed to warm to room temperature and stirred for another 30 minutes until TLC showed the reaction was complete. The precipitate was filtered over celite, washed three times with dichloromethane (5 mL) and concentrated. The residue was then engaged into to next step without further purification. The aldehyde 2-((1-((2S,4S,5R)-4-((tert-butyldimethylsilyl)oxy)-5-(((tert-butyldimethylsilyl)oxy)methyl)tetrahydrofuran-2-yl)-4-(((4-methoxyphenyl)diphenylmethyl)amino)-2-oxo-1,2-dihydropyrimidin-5-yl)thio)acetaldehyde 38 obtained was dissolved in dry methanol (10 mL) and a solution of 23 (263 mg, 0.307 mmol) in dry methanol (6 mL) was added. 2-picoline borane complex (22 mg, 0.21 mmol) was added and the mixture stirred at room temperature under argon for 5 hours. The reaction mixture had a pH-5-6. 2-picoline borane complex (101 mg, 0.921 mmol) was added again and the mixture stirred at room temperature under argon overnight. Then the reaction mixture was concentrated, diluted in chloroform (30 mL), washed with saturated aqueous sodium bicarbonate (10 mL), dried over magnesium sulfate, filtered and concentrated. The residue was then purified by silica gel flash column chromatography eluting with a petroleum ether ethyl acetate gradient to give tert-butyl (S)-4-((((2R,3R,4R,5R)-5-(6-benzamido-9H-purin-9-yl)-3,4-bis((tert-butyldimethylsilyl)oxy)tetrahydrofuran-2-yl)methyl)(2-((1-((2S,4S,5R)-4-((tert-butyldimethylsilyl)oxy)-5-(((tert-butyldimethylsilyl)oxy)methyl)tetrahydrofuran-2-yl)-4-(((4-methoxyphenyl)diphenylmethyl)amino)-2-oxo-1,2-dihydropyrimidin-5-yl)thio)ethyl)amino)-2-((tert-butoxycarbonyl)amino)butanoate 39 (180 mg, 36% yield) as a white foam. $R_f$=0.50 (ethyl acetate/petroleum ether, 1/1). $^1$H NMR (500 MHz, CDCl$_3$) δ9.51 (s, 1H), 8.71 (s, 1H), 8.28 7.84 (m, 6H), 7.62-7.52 (m, 2H), 7.45 (dd, J=8.4, 7.1 Hz, 2H), 7.36 (td, J=7.6, 1.2 Hz, 1H), 7.22-7.13 (m, 8H), 7.15-7.04 (m, 3H), 6.74 (d, J=9.0 Hz, 2H), 6.16 (t, J=6.6 Hz, 1H), 5.87 (d, J=5.1 Hz, 1H), 5.27 (d, J=8.3 Hz, 1H), 5.02 (d, J=4.9 Hz, 1H), 4.29 (dt, J=6.0, 2.9 Hz, 1H), 4.13 (d, J=10.0 Hz, 3H), 3.88 (q, J=3.0 Hz, 1H), 3.79 (dd, J=11.4, 3.1 Hz, 1H), 3.71 (s, 4H), 2.87 (dd, J=14.1, 8.2 Hz, 1H), 2.83 2.78 (m, 1H), 2.75-2.65 (m, 2H), 2.60 (dt, J=16.5, 7.2 Hz, 3H), 2.51 (ddd, J=13.5, 8.9, 4.9 Hz, 1H), 2.33 (ddd, J=13.3, 6.0, 3.0 Hz, 1H), 1.87 (dt, J=13.4, 6.6 Hz, 1H), 1.64 (d, J=13.1 Hz, 2H), 1.39 (s, 9H), 1.38 (s, 9H), 0.92 (s, 9H), 0.88 (s, 9H), 0.82 (s, 9H), 0.79 (s, 9H), 0.09 (s, 3H), 0.08 (s, 3H), 0.07 (s, 3H), 0.07 (s, 3H), 0.00 (s, 6H), −0.02 (s, 3H), −0.06 (s, 3H), −0.27 (s, 3H). $^{13}$C NMR (126 MHz, CDCl$_3$) δ171.45, 168.74, 164.89, 162.03, 158.27, 155.46, 154.56, 152.21, 151.49, 150.15, 145.82, 144.63, 144.56, 142.80, 141.57, 136.49, 133.50, 132.74, 132.61, 131.57, 130.09, 128.81, 128.65, 128.43, 128.34, 128.02, 127.88, 127.85, 127.77, 126.84, 124.24, 113.18, 98.61, 94.57, 90.21, 88.02, 86.77, 83.78, 81.87, 79.62, 76.45, 74.38, 73.73, 72.25, 71.14, 63.01, 56.57, 55.16, 54.68, 52.82, 50.87, 42.22, 34.28, 31.94, 29.71, 29.66, 29.36, 28.37, 28.02, 26.10, 25.94, 25.87, 25.75, 22.70, 18.43, 18.05, 17.99, 17.90, 14.11, 0.00, −4.28, −4.43, −4.56, −4.59, −4.64, −4.87, −5.18, −5.33. HRMS (m/z) calcd. for C$_{85}$H$_{128}$N$_{10}$O$_{13}$NaSSi$_4$ [M+Na]$^+$ 1663.8351, found 1663.8358.

Compound 39 (67 mg, 0.041 mmol) was dissolved in 7N ammonia in methanol (18 mL) and the reaction mixture stirred at room temperature under argon overnight. The reaction mixture was then concentrated and purified by silica gel flash column chromatography eluting with a dichloromethane-methanol gradient to give tert-butyl (S)-4-((((2R,3R,4R,5R)-5-(6-amino-9H-purin-9-yl)-3,4-bis((tert-butyldimethylsilyl)oxy)tetrahydrofuran-2-yl)methyl)(2-((1-((2S,4S,5R)-4-((tert-butyldimethylsilyl)oxy)-5-(((tert-butyldimethylsilyl)oxy)methyl)tetrahydrofuran-2-yl)-4-(((4-methoxyphenyl)diphenylmethyl)amino)-2-oxo-1,2-dihydropyrimidin-5-yl)thio)ethyl)amino)-2-((tert-butoxycarbonyl)amino)butanoate 40 (62 mg, Quant.) as an colorless foam. $R_f$=0.08 (petroleum ether/ethyl acetate; 1/1). $^1$H NMR (500 MHz, CDCl$_3$) δ8.22 (s, 1H), 7.90 (s, 1H), 7.84-7.70 (m, 3H), 7.59 (s, 1H), 7.30-7.03 (m, 13H), 6.74 (d, J=8.9 Hz, 2H), 6.10 (dd, J=7.3, 5.8 Hz, 1H), 5.90 (br s, 1H), 5.76 (d, J=5.1 Hz, 1H), 5.29 (d, J=8.1 Hz, 1H), 5.01 (t, J=4.1 Hz, 2H), 4.29 (dt, J=5.9, 2.9 Hz, 1H), 4.15-4.09 (m, 1H), 3.88 (dd, J=3.0 Hz, 1H), 3.71 (s, 3H), 3.70-3.68 (m, 1H), 2.80 (d, J=5.5 Hz, 1H), 2.75-2.63 (m, 4H), 2.55 (q, J=7.3 Hz, 1H), 2.49 (td, J=8.5, 4.4 Hz, 1H), 2.31 (ddd, J=13.2, 5.9, 2.9 Hz, 1H), 2.13-2.04 (m, 1H), 1.81-1.80 (m, 1H), 1.63-1.61 (m, 1H), 1.37 (s, 18H), 0.90 (s, 9H), 0.87 (s, 9H), 0.82 (s, 9H), 0.77 (s, 9H), 0.07 (br s, 6H), 0.06 (s, 3H), 0.04 (s, 3H), −0.00 (s, 6H), −0.08 (s, 3H), −0.30 (s, 3H). $^{13}$C NMR (126 MHz, CDCl$_3$) δ171.48, 169.43, 162.02, 158.28, 155.74, 155.46, 154.22, 152.78, 149.47, 145.85, 144.64, 144.60, 140.47, 136.50, 133.55, 131.73, 130.12, 128.65, 128.45, 127.88, 127.46, 126.85, 120.82, 113.17, 98.70, 90.02, 87.92, 86.61, 83.56, 81.72, 79.52, 74.38, 73.42, 72.34, 71.08, 63.02, 60.35, 56.41, 55.13, 54.56, 52.88, 50.83, 42.12, 34.35, 29.70, 28.34, 27.98, 26.06, 25.85, 25.72, 21.01, 18.40, 18.01, 17.95, 17.87, 14.18, −4.33, −4.47, −4.63, −4.89, −5.01, −5.23, −5.38. HRMS (m/z) calcd. for C$_{78}$H$_{124}$N$_{10}$O$_{12}$NaSSi$_4$ [M+Na]$^+$ 1559.8120, found 1559.8110.

Tetrabutylammonium fluoride (81 μL of a 1M solution in tetrahydrofuran, 81 mmol) was added to a solution of 40 (31 mg, 0.020 mmol) in dry tetrahydrofuran (5 mL), the reaction was stirred at room temperature for 1 hour until TLC showed the reaction was complete. The reaction mixture was concentrated in vacuo. The residue was diluted with chloroform (15 mL) and washed three times with water (5 mL), dried over magnesium sulfate, filtered and concentrated. The residue was then purified by silica gel flash column chromatography eluting with a dichloromethane methanol gradient to afford tert-butyl (S)-4-((((2R,3S,4R,5R)-5-(6-amino-9H-purin-9-yl)-3,4-dihydroxytetrahydrofuran-2-yl)methyl)(2-((1-((2S,4S,5R)-4-hydroxy-5-(hydroxymethyl)tetrahydrofuran-2-yl)-4-(((4-methoxyphenyl)diphenylmethyl)amino)-2-oxo-1,2-dihydropyrimidin-5-yl)thio)ethyl)amino)-2-((tert-butoxycarbonyl)amino)butanoate 41 (20 mg, 92% yield) as an oil. $R_f$=0.05 (10% methanol in dichloromethane). $^1$H NMR (500 MHz, MeOD) δ8.39 (s, 1H), 8.19 (s, 1H), 8.18 (s, 1H), 7.37-7.24 (m, 8H), 7.22-7.16 (m, 4H), 6.82 (d, J=9.0 Hz, 2H), 6.03 (t, J=6.3 Hz, 1H), 5.94 (d, J=4.4 Hz, 1H), 4.70 (dd, J=5.4, 4.3 Hz, 1H), 4.52 (s, 1H), 4.34 (dt, J=6.3, 4.1 Hz, 1H), 4.26 (t, J=5.4 Hz, 1H), 4.09 (m, 2H), 3.90 (q, J=3.4 Hz, 1H), 3.80 (dd, J=12.0, 3.1 Hz, 1H), 3.75 (s, 3H), 3.72 (dd, J=12.0, 3.5 Hz, 1H), 2.92 (dd, J=14.0, 4.4 Hz, 1H), 2.82-2.70 (m, 4H), 2.60 (m, 2H), 2.31 (ddd, J=13.6, 6.3, 4.2 Hz, 1H), 2.10 (dt, J=13.6, 6.4 Hz, 1H), 1.95-1.85 (m, 1H), 1.72-1.61 (m, 1H), 1.40 (s, 9H), 1.39 (s, 9H). $^{13}$C NMR (126 MHz, MeOD) δ172.33, 162.63, 158.60, 155.30, 152.48, 146.49, 144.43, 140.17, 136.32, 129.90, 128.45, 127.55, 126.56, 112.85, 99.93, 89.40, 87.59, 86.61, 82.61, 81.21, 78.04, 73.17, 72.06, 71.02, 70.28, 61.04, 55.86, 54.33, 54.22, 52.77, 50.94, 40.91, 33.82, 27.40, 26.92. HRMS (m/z) calcd. for C$_{54}$H$_{69}$N$_{10}$O$_{12}$S [M+H]$^+$ 1081.4817, found 1081.4816.

Compound 41 (20 mg, 0.018 mmol) was diluted in a 1:1 mixture of 1,4-dioxane/water (10 mL). Resin ion exchange Dowex 50WX8-H+(652 mg) was added and the reaction mixture stirred slowly at room temperature during 48 hours. Filtration of the resin was followed by several washing with water then aqueous ammonia 0.2N (300 mL) and concentrated. The residue was then purified by Sep-Pak® Plus C18 environmental cartridge eluting with a water-methanol gradient to give (S)-2-amino-4-((2-((4-amino-1-((2S,4S,5R)-4-hydroxy-5-(hydroxymethyl)tetrahydrofuran-2-yl)-2-oxo-1,2-dihydropyrimidin-5-yl)thio)ethyl)(((2R,3S,4R,5R)-5-(6-amino-9H-purin-9-yl)-3,4-dihydroxytetrahydrofuran-2-yl)methyl)amino)butanoic acid 42 (9 mg, 75%) as a white solid after freeze-drying. Reverse phase TLC: $R_f$=0.24 (50% methanol in water) $^1$H NMR (500 MHz, D$_2$O) δ8.22 (s, 1H), 8.20 (s, 1H), 8.08 (s, 1H), 6.04 (t, J=6.3 Hz, 1H), 5.96 (d, J=3.8 Hz, 1H), 4.36 (dt, J=6.5, 4.5 Hz, 1H), 4.22 (t, J=4.9 Hz, 2H), 4.00 (td, J=4.4, 3.3 Hz, 1H), 3.81 (dd, J=12.6, 3.3 Hz, 1H), 3.76-3.73 (m, 1H), 3.71 (dd, J=12.5, 4.6 Hz, 1H), 2.89 (d, J=4.9 Hz, 2H), 2.74 (m, 6H), 2.41 (ddd, J=14.0, 6.5, 4.6 Hz, 1H), 2.16 (dt, J=14.0, 6.3 Hz, 1H), 2.04 (dq, J=11.7, 6.5, 5.7 Hz, 1H), 1.92 (dq, J=14.5, 7.1 Hz, 1H). $^{13}$C NMR (126 MHz, D$_2$O) δ174.23, 165.78, 156.44, 155.61, 152.90, 148.70, 147.19, 139.89, 119.10, 99.03, 88.65, 86.86, 86.45, 81.43, 73.13, 71.99, 70.02, 60.82, 55.48, 54.71, 52.97, 51.41, 39.91, 30.85, 26.68. HRMS (m/z) calcd. for $C_{25}H_{37}N_{10}O_9S$ [M+H]$^+$ 653.2466, found 653.2473.

Example 6: Synthesis of (S)-2-amino-4-((2-(4-amino-1-((2S,4S,5R)-4-hydroxy-5-(hydroxymethyl)tetrahydrofuran-2-yl)-2-oxo-1,2-dihydropyrimidin-5-yl)ethyl)-(((2R,3S,4R,5R)-5-(6-amino-9H-purin-9-yl)-3,4-dihydroxytetrahydrofuran-2-yl)methyl)amino)butanoic acid 56

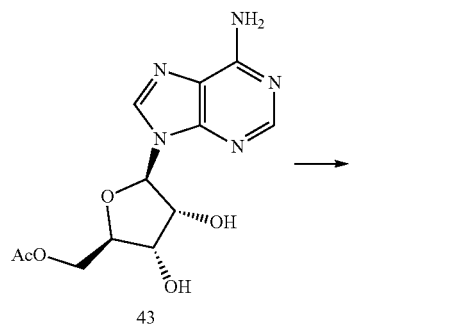

43

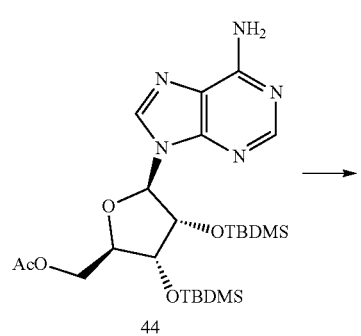

44

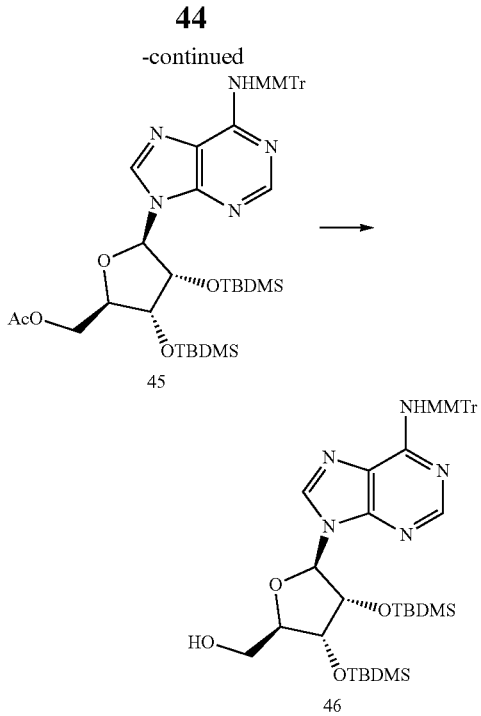

43 (7.469 g, 21.02 mmol) (Tatani, K., Hiratochi, M., Nonaka, Y., Isaji, M., Shuto, S., ACS Med. Chem. Lett., 2015, 6(3), 244-248), tert-butyldimethylsilyl chloride (7.681 g, 50.45 mmol) and imidazole (8.385 g, 121.9 mmol) were dissolved in dry N,N-dimethylformamide (20 mL). The reaction was heated to 70° C. under Ar for 4 hours until TLC showed the reaction was complete. The reaction mixture was diluted with ethyl acetate (200 mL) and washed with water (3×100 mL), dried over anhydrous magnesium sulfate then filtered. The organic layer was concentrated in vacuo and the residue purified by silica gel flash column chromatography eluting with an methanol—ethyl acetate gradient to give ((2R,3R,4R,5R)-5-(6-amino-9H-purin-9-yl)-3,4-bis((tert-butyldimethylsilyl)oxy)tetrahydrofuran-2-yl)methyl acetate 44 (8.136 g, 72% yield). Rf=0.69 (5% ethanol/ethyl acetate). $^1$H NMR (500 MHz, CDCl$_3$) δ8.33 (s, 1H), 7.97 (s, 1H), 5.89 (d, J=4.1 Hz, 1H), 5.85 (s, 2H), 4.90 (t, J=4.2 Hz, 1H), 4.54-4.43 (m, 1H), 4.36 (t, J=4.5 Hz, 1H), 4.33-4.26 (m, 2H), 2.09 (s, 3H), 0.92 (s, 9H), 0.84 (s, 9H), 0.09 (s, 3H), 0.08 (s, 3H), 0.00 (s, 3H), −0.12 (s, 3H). $^{13}$C NMR (126 MHz, CDCl$_3$) δ170.42, 155.55, 152.94, 149.57, 139.81, 120.57, 89.80, 81.90, 74.54, 71.97, 63.22, 25.78, 25.71, 20.79, 18.03, 17.90, −4.39, −4.72, −4.88, −4.98. HRMS (m/z) calcd. for $C_{24}H_{44}N_5O_5$ [M+H]$^+$ 538.2881, found 538.2878.

44 (8.136 g, 15.13 mmol) was dissolved in dry dichloromethane (65 mL). 2,4,6-trimethylpyridine (8.07 mL, 60.51 mmol), 4-methoxytrityl chloride (9.632 g, 30.26 mmol) and silver nitrate (3.09 g, 18.15 mmol) were successively added and the reaction was stirred under Ar for 3 hours until TLC showed the reaction was complete. The reaction mixture was diluted with ethyl acetate (200 mL), filtered over Celite and washed with 10% citric acid (200 mL), brine (200 mL) saturated aqueous sodium bicarbonate (200 mL), dried over anhydrous magnesium sulfate then filtered. The organic layer was concentrated in vacuo and the residue purified by silica gel flash column chromatography eluting with an ethyl acetate—petroleum ether gradient to give ((2R,3R,4R,5R)-3,4-bis((tert-butyldimethylsilyl)oxy)-5-(6-(((4-methoxyphenyl)diphenylmethyl)amino)-9H-purin-9-yl)tetrahydrofuran-2-yl)methyl acetate 45 (12.07 g, 98% yield). Rf=0.17 (20% ethyl acetate/petroleum ether). $^1$H NMR (500 MHz, CDCl$_3$) δ8.01 (s, 1H), 7.89 (s, 1H), 7.40-7.10 (m, 14H), 6.88 (s, 1H), 6.83-6.72 (m, 2H), 5.85 (d, J=4.4 Hz, 1H), 4.87 (t, J=4.3 Hz, 1H), 4.52-4.43 (m, 1H), 4.41 (t, J=4.4 Hz, 1H), 4.34-4.21 (m, 2H), 3.77 (s, 3H), 2.06 (s, 3H), 0.92 (s, 9H), 0.81 (s, 9H), 0.09 (s, 3H), 0.08 (s, 3H), −0.02 (s, 3H), −0.18 (s, 3H). $^{13}$C NMR (126 MHz, CDCl$_3$) δ170.45, 158.33, 154.22, 152.19, 148.46, 145.25, 139.31, 137.30, 130.21, 128.91, 127.84, 126.83, 121.88, 113.14, 89.74, 82.07, 74.44, 72.05, 71.06, 63.31, 55.21, 25.81, 25.71, 20.80, 18.05, 17.91, −4.38, −4.69, −4.93, −5.02. HRMS (m/z) calcd. for C$_{44}$H$_{60}$N$_5$O$_6$Si$_2$ [M+H]$^+$ 810.4082, found 810.4075.

45 (12.07 g, 14.90 mmol) was dissolved in 7N ammonia in methanol (120 mL) and the reaction was stirred for 2 hours at 40° C. until TLC showed the reaction was complete. The reaction mixture was concentrated in vacuo and the residue purified by silica gel flash column chromatography eluting with an ethyl acetate—petroleum ether gradient to give ((2R,3R,4R,5R)-3,4-bis((tert-butyldimethylsilyl)oxy)-5-(6-(((4-methoxyphenyl)diphenylmethyl)amino)-9H-purin-9-yl)tetrahydrofuran-2-yl)methanol 46 (11.15 g, 97% yield). Rf=0.23 (20% ethyl acetate/petroleum ether). $^1$H NMR (500 MHz, CDCl$_3$) δ7.99 (s, 1H), 7.78 (s, 1H), 7.37-7.17 (m, 12H), 7.00 (s, 1H), 6.82-6.74 (m, 2H), 6.70 (dd, J=12.3, 2.0 Hz, 1H), 5.76 (d, J=7.9 Hz, 1H), 4.97 (dd, J=7.9, 4.5 Hz, 1H), 4.29 (d, J=4.6 Hz, 1H), 4.14 (d, J=1.6 Hz, 1H), 3.89 (dt, J=13.1, 1.9 Hz, 1H), 3.78 (s, 3H), 3.71-3.60 (m, 1H), 0.94 (s, 9H), 0.73 (s, 9H), 0.12 (s, 3H), 0.10 (s, 3H), −0.15 (s, 3H), −0.64 (s, 3H). $^{13}$C NMR (126 MHz, CDCl$_3$) δ158.41, 154.80, 151.60, 147.49, 145.04, 145.00, 140.37, 137.08, 130.15, 128.87, 128.85, 127.89, 126.94, 122.73, 113.19, 90.92, 89.66, 74.04, 73.88, 71.32, 63.02, 55.22, 25.82, 25.69, 18.08, 17.81, −4.57, −4.60, −4.67, −6.25. HRMS (m/z) calcd. for C$_{42}$H$_{58}$N$_5$O$_5$Si$_2$ [M+H]$^+$ 768.3977, found 768.3970.

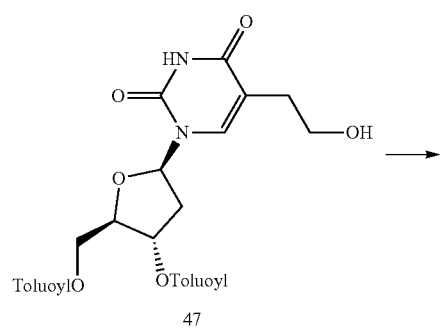

47

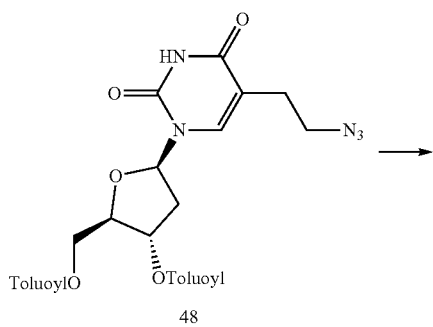

48

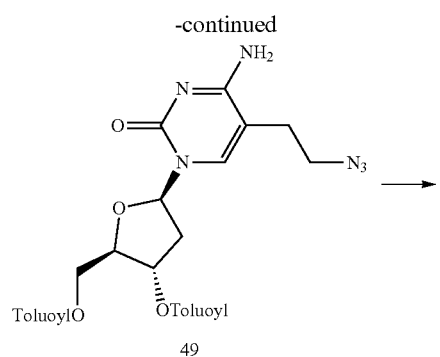

49

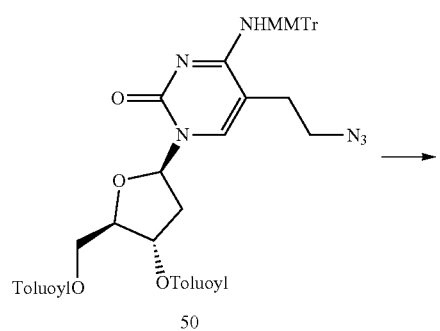

50

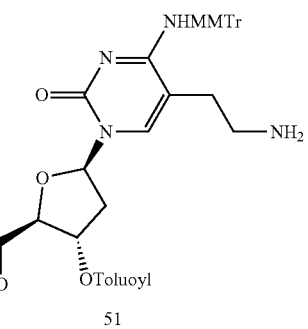

51

Methanesulfonyl chloride (0.411 mL, 5.25 mmol) was added drop-wise to a solution of 47 (Griengl, H., Bodenteich, M., Hayden, W., Wanek, E., Streicher, W., Stutz, P., Bachmayer, H., Ghazzouli, I. and Rosenwirth, B., J. Med. Chem., 1985, 28, 1679-1684) (1.78 g, 3.50 mmol) in dry pyridine (18 mL) under argon. The reaction was warmed to 40° C. and after 30 minutes TLC showed the reaction was complete. The reaction mixture was concentrated in vacuo and the residue dissolved in ethyl acetate (100 mL), washed with saturated aqueous sodium bicarbonate (100 mL), brine (100 mL) then the organic layer was dried over anhydrous magnesium sulfate, filtered and concentrated in vacuo. The crude mesylate was dissolved in dry N,N-dimethylformamide (9 mL). Sodium azide (0.276 g, 4.20 mmol) was added and the reaction heated at 70° C. for 5 hours until TLC showed the reaction was complete. The residue was purified by silica gel flash column chromatography eluting with an ethyl acetate—petroleum ether gradient to give (2R,3S,5R)-5-(5-(2-azidoethyl)-2,4-dioxo-3,4-dihydropyrimidin-1

(2H)-yl)-2-(((4-methylbenzoyl)oxy)methyl)tetrahydrofuran-3-yl 4-methylbenzoate 48 (1.421 g, 76% yield) as a white solid. $R_f$=0.55 (60% ethyl acetate/petroleum ether). $^1$H NMR (500 MHz, CDCl$_3$) δ8.87 (s, 1H), 8.05-7.83 (m, 4H), 7.38 (s, 1H), 7.33-7.22 (m, 5H), 6.44 (dd, J=8.8, 5.4 Hz, 1H), 5.64 (d, J=6.7 Hz, 1H), 4.79 (dd, J=12.2, 2.9 Hz, 1H), 4.65 (dd, J=12.2, 3.8 Hz, 1H), 4.57-4.48 (m, 1H), 3.36-3.21 (m, 2H), 2.74 (ddd, J=14.3, 5.5, 1.5 Hz, 1H), 2.43 (s, 6H), 2.38-2.23 (m, 3H). $^{13}$C NMR (126 MHz, CDCl$_3$) 166.07, 166.02, 162.69, 150.01, 144.64, 144.60, 136.54, 129.85, 129.54, 129.50, 129.30, 126.59, 126.27, 111.47, 85.21, 83.00, 74.87, 64.13, 49.33, 38.19, 27.00, 21.74, 21.71. HRMS (m/z) calcd. for $C_{27}H_{28}N_5O_7$ [M+H]$^+$ 534.1989, found 534.1994.

p-Toluenesulfonyl chloride (2.37 g, 12.3 mmol) was added to a solution of 48 (1.64 g, 3.07 mmol) and N-methylpiperidine (3.02 mL, 24.6 mmol) in dry acetonitrile (66 mL) and the reaction was stirred at room temperature under argon for 1 hour. 28% aqueous ammonia (16 mL) was added in one portion and the reaction stirred at room temperature for 2 hours. The reaction mixture was diluted with ethyl acetate (100 mL), washed with saturated aqueous sodium bicarbonate (3×50 mL), then filtered and dried over anhydrous magnesium sulfate. The organic layer was concentrated in vacuo and the residue purified by silica gel flash column chromatography eluting with a methanol—ethyl acetate gradient to give (2R,3S,5R)-5-(4-amino-5-(2-azidoethyl)-2-oxopyrimidin-1(2H)-yl)-2-(((4-methylbenzoyl)oxy)methyl)tetrahydrofuran-3-yl 4-methylbenzoate 49 (0.925 g, 57% yield) as an oil. $R_f$=0.18 (5% ethanol/ethyl acetate). $^1$H NMR (500 MHz, CDCl$_3$) δ7.95 (d, J=8.2 Hz, 2H), 7.90 (d, J=8.2 Hz, 2H), 7.45 (s, 1H), 7.36-7.16 (m, 4H), 6.42 (dd, J=8.6, 5.4 Hz, 1H), 5.69-5.53 (m, 1H), 4.81 (dd, J=12.1, 2.9 Hz, 1H), 4.62 (dd, J=12.1, 4.0 Hz, 1H), 4.59-4.49 (m, 1H), 3.33-3.13 (m, 2H), 2.92 (ddd, J=14.4, 5.5, 1.5 Hz, 1H), 2.43 (s, 3H), 2.42 (s, 3H), 2.31-2.14 (m, 3H). $^{13}$C NMR (126 MHz, CDCl$_3$) δ166.17, 166.08, 165.08, 155.33, 144.56, 144.47, 139.02, 129.84, 129.53, 129.47, 129.26, 126.63, 126.40, 102.88, 86.64, 83.18, 75.28, 64.30, 50.30, 39.13, 27.65, 21.72, 21.69. HRMS (m/z) calcd. for $C_{27}H_{29}N_6O_6$ [M+H]$^+$ 533.2149, found 533.2149.

49 (0.925 g, 1.74 mmol) was dissolved in dry dichloromethane (19 mL). 2,4,6-trimethylpyridine (0.927 mL, 6.95 mmol), 4-methoxytrityl chloride (1.11 g, 3.47 mmol) and silver nitrate (0.354 g, 2.08 mmol) were successively added and the reaction was stirred under Ar for 2 hours until TLC showed the reaction was complete. The reaction mixture was diluted with ethyl acetate (100 mL), filtered over Celite and washed with 10% citric acid (50 mL), brine (50 mL) saturated aqueous sodium bicarbonate (50 mL), then filtered and dried over anhydrous magnesium sulfate. The organic layer was concentrated in vacuo and the residue purified by silica gel flash column chromatography eluting with an ethyl acetate—petroleum ether gradient to give (2R,3S,5R)-5-(5-(2-azidoethyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 50 (1.228 g, 88% yield). Rf=0.27 (40% ethyl acetate/petroleum ether). $^1$H NMR (500 MHz, DMSO-d6) δ7.89 (dd, J=8.3, 2.8 Hz, 4H), 7.43 (s, 1H), 7.38-7.10 (m, 17H), 6.85-6.78 (m, 2H), 6.19 (dd, J=8.2, 6.3 Hz, 1H), 5.56 (dt, J=5.9, 2.8 Hz, 1H), 4.60 (dd, J=11.8, 4.0 Hz, 1H), 4.51 (dd, J=11.8, 5.2 Hz, 1H), 4.43 (ddd, J=5.2, 4.1, 2.8 Hz, 1H), 3.71 (s, 3H), 3.49 (td, J=6.8, 2.4 Hz, 2H), 2.74-2.60 (m, 2H), 2.48-2.40 (m, 2H), 2.39 (s, 3H), 2.38 (s, 3H). $^{13}$C NMR (126 MHz, DMSO-d6) δ165.47, 165.20, 161.36, 157.44, 153.06, 144.85, 143.99, 143.91, 138.94, 136.66, 129.95, 129.37, 129.27, 128.43, 127.43, 126.56, 126.46, 126.11, 112.71, 104.42, 84.94, 81.14, 74.85, 69.99, 64.23, 54.93, 50.16, 36.60, 26.48, 21.16. HRMS (m/z) calcd. for $C_{47}H_{45}N_6O_7$ [M+H]$^+$ 805.3350, found 805.3342.

50 (0.621 g, 0.772 mmol) was dissolved in dry methanol (16 mL), added 10% palladium on carbon (0.124 g) placed under vacuum then hydrogen three times then stirred under hydrogen for 24 hours. The reaction mixture was filtered over Celite washing with methanol, concentrated in vacuo and then the residue was purified by silica gel flash column chromatography eluting with an methanol—ethyl acetate gradient to give (2R,3S,5R)-5-(5-(2-aminoethyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 51 (0.372 g, 62% yield). Rf=0.18 (5% ethanol/ethyl acetate). $^1$H NMR (500 MHz, DMSO-d6) δ7.99-7.80 (m, 4H), 7.38-7.03 (m, 17H), 6.85-6.70 (m, 2H), 6.21 (dd, J=8.3, 6.3 Hz, 1H), 5.57 (dt, J=5.9, 2.8 Hz, 1H), 4.62 (dd, J=11.8, 3.9 Hz, 1H), 4.49 (dd, J=11.8, 4.8 Hz, 1H), 4.44-4.34 (m, 1H), 3.70 (s, 3H), 2.67-2.53 (m, 2H), 2.44-2.30 (m, 3H), 2.39 (s, 3H), 2.38 (s, 3H), 2.28-2.17 (m, 1H). $^{13}$C NMR (126 MHz, DMSO-d6) δ165.94, 165.69, 163.25, 157.73, 153.82, 145.56, 144.48, 144.43, 138.09, 130.49, 129.89, 129.87, 129.78, 129.06, 127.75, 127.04, 126.97, 126.36, 113.05, 109.61, 85.09, 81.50, 75.44, 70.33, 64.67, 55.36, 42.33, 37.04, 32.80, 21.68, 21.65. HRMS (m/z) calcd. for $C_{47}H_{47}N_4O_7$ [M+H]$^+$779.3445, found 779.3438.

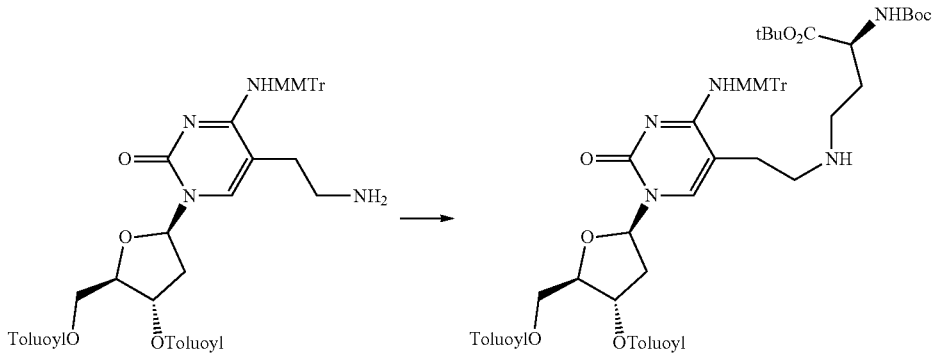

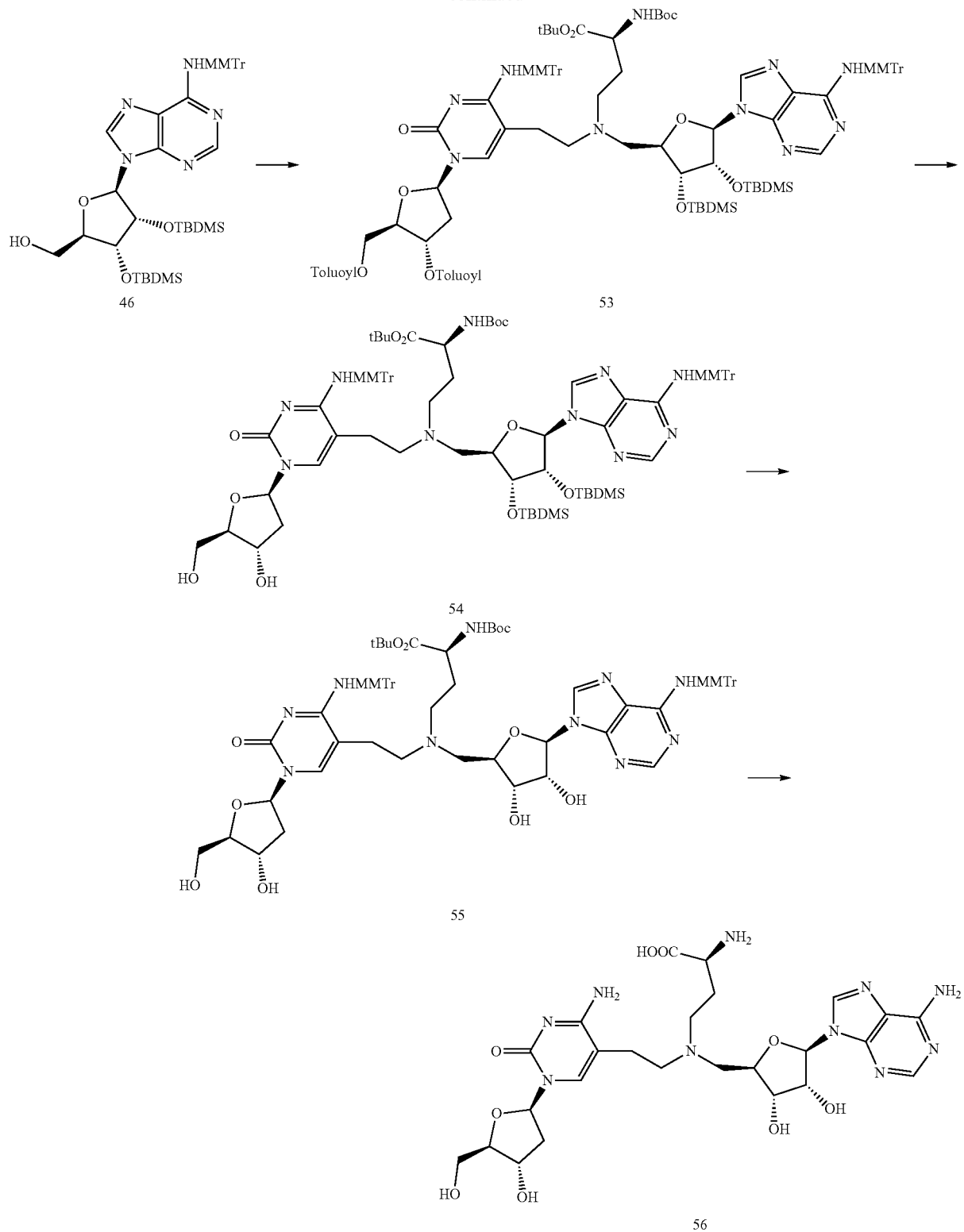

tert-Butyl L-2-((tert-butoxycarbonyl)amino)-4-oxobutanoate (Roberts, S. J, Morris, J. C., Dobson, R. C. J., Baxter, C. L., Gerrard, J. A., ARKIVOC 2004, 166-177; http://hdl.handle.net/2440/34486) (0.125 g, 0.457 mmol) and 51 (0.356 g, 0.457 mmol) were dissolved in dry methanol (9 mL) and the reaction stirred for 5 minutes. 2-Picoline borane complex (0.060 g, 0.548 mmol) was added and the reaction mixture stirred at room temperature for 24 hours. The mixture was concentrated, then diluted with ethyl acetate (50 mL), washed with saturated aqueous sodium bicarbonate (50 mL), brine (50 mL), dried over anhydrous magnesium sulfate, filtered and concentrated. The residue was purified by silica gel flash chromatography eluting with a petroleum ether-ethyl acetate gradient to give (2R,3S,5S)-5-(5-(2-(((S)-4-(tert-butoxy)-3-((tert-butoxycarbonyl)amino)-4-oxobutyl)amino)ethyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 52 (0.331 g, 70% yield). $R_f$=0.30 (60% ethyl acetate/petroleum ether). $^1$H NMR (500 MHz, DMSO-d6) δ 9.86 (s, 1H), 8.00 7.78 (m, 4H), 7.42 7.07 (m, 18H), 6.93 (d, J=7.9 Hz, 1H), 6.79 (d, J=8.9 Hz, 2H), 6.21 (dd, J=8.4, 6.1 Hz, 1H), 5.63-5.50 (m, 1H), 4.63 (dd, J=11.8, 3.8 Hz, 1H), 4.49 (dd, J=11.9, 4.7 Hz, 1H), 4.45-4.36 (m, 1H), 3.71 (s, 3H), 3.71-3.66 (m, 1H), 2.39 (s, 3H), 2.38 (s, 3H), 2.56-2.17 (m, 8H), 1.39 (s, 9H), 1.36 (s, 9H), 1.48-1.26 (m, 2H). $^{13}$C NMR (126 MHz, DMSO-d6) δ171.96, 165.93, 165.69, 162.83, 157.79, 155.91, 153.76, 145.46, 144.48, 144.39, 138.03, 137.19, 130.47, 129.89, 129.86, 129.78, 128.98, 127.81, 127.04, 126.96, 126.41, 113.10, 109.22, 85.16, 81.58, 80.67, 78.51, 75.47, 70.25, 64.73, 55.36, 53.12, 49.66, 46.35, 37.20, 30.34, 29.89, 28.65, 28.10, 21.66. HRMS (m/z) calcd. for $C_{60}H_{70}N_5O_{11}$ [M+H]$^+$ 1036.5072, found 1036.5065.

Dess-Martin periodinane (0.296 g, 0.678 mmol) was added to a solution of 46 (0.347 g, 0.452 mmol) in dry dichloromethane (9 mL) at RT. The reaction mixture was stirred under argon for 30 minutes until TLC showed the reaction was complete. The precipitate was filtered over celite, washed with dichloromethane and the organic layer was quenched with 10% aqueous sodium thiosulfate then filtered and dried over magnesium sulfate and concentrated. A portion of the crude aldehyde (0.270 g, 0.352 mmol), 52 (0.317 g, 0.306 mmol) and 2-picoline borane complex (0.060 g, 0.548 mmol) were dissolved in dry methanol (8 mL) and the reaction stirred at room temperature for 48 hours. The mixture was concentrated, then diluted with ethyl acetate (50 mL), washed with saturated aqueous sodium bicarbonate (50 mL), brine (50 mL), filtered and dried over anhydrous magnesium sulfate. The residue was purified by silica gel flash chromatography eluting with a petroleum ether-ethyl acetate gradient to give (2R,3S,5S)-5-(5-(2-((((2R,3R,4R,5R)-3,4-bis((tert-butyldimethylsilyl)oxy)-5-(6-(((4-methoxyphenyl)diphenylmethyl)amino)-9H-purin-9-yl)tetrahydrofuran-2-yl)methyl)((S)-4-(tert-butoxy)-3-((tert-butoxycarbonyl)amino)-4-oxobutyl)amino)ethyl)-4-(((4-methoxyphenyl)diphenylmethyl)amino)-2-oxopyrimidin-1(2H)-yl)-2-(((4-methylbenzoyl)oxy)methyl)tetrahydrofuran-3-yl 4-methylbenzoate 53 (0.323 g, 59% yield). $R_f$0.16 (40% ethyl acetate/petroleum ether). $^1$H NMR (500 MHz, MeOD) δ8.16 (s, 1H), 7.96-7.88 (m, 2H), 7.87-7.81 (m, 2H), 7.77 (s, 1H), 7.38-7.02 (m, 33H), 6.73 (dd, J=9.0, 2.2 Hz, 4H), 6.21 (dd, J=8.7, 5.5 Hz, 1H), 5.84 (d, J=6.5 Hz, 1H), 5.44 (d, J=6.4 Hz, 1H), 4.92 (dd, J=6.5, 4.5 Hz, 1H), 4.67 (dd, J=12.0, 3.5 Hz, 1H), 4.53 (dd, J=12.0, 4.0 Hz, 1H), 4.45 4.39 (m, 1H), 4.15 (d, J=9.3 Hz, 1H), 4.05-3.99 (m, 1H), 3.97-3.90 (m, 1H), 3.70 (s, 3H), 3.70 (s, 3H), 2.94 (dd, J=14.4, 9.5 Hz, 1H), 2.76-2.67 (m, 1H), 2.58-2.23 (m, 6H), 2.39 (s, 3H), 2.29 (s, 3H), 2.20-2.05 (m, 2H), 1.86-1.72 (m, 1H), 1.65 1.52 (m, 1H), 1.40 (s, 9H), 1.40 (s, 9H), 0.95 (s, 9H), 0.73 (s, 9H), 0.13 (s, 3H), 0.12 (s, 3H), −0.09 (s, 3H), −0.41 (s, 3H). $^{13}$C NMR (126 MHz, MeOD) δ171.79, 166.02, 162.52, 158.45, 158.37, 156.45, 155.27, 154.20, 151.62, 148.52, 145.05, 144.99, 144.62, 144.36, 141.02, 136.96, 130.28, 130.04, 129.40, 129.36, 129.11, 128.92, 128.85, 128.71, 127.34, 127.30, 126.70, 126.63, 126.44, 126.29, 121.27, 112.63, 108.30, 89.36, 86.10, 83.54, 82.69, 81.31, 79.15, 75.55, 74.68, 73.46, 71.29, 71.03, 64.23, 56.48, 54.36, 54.32, 53.65, 53.38, 52.93, 50.62, 37.91, 28.78, 27.45, 27.03, 25.13, 24.92, 22.31, 20.49, 20.30, 17.58, 17.40, −5.20, −5.43, −5.63, −6.44. HRMS (m/z) calcd. for $C_{102}H_{125}N_{10}O_{15}Si_2$ [M+H]$^+$ 1785.8864, found 1785.8870.

53 (0.295 g, 0.165 mmol) was dissolved in 7M ammonia in methanol (6 mL) and the reaction stirred at room temperature for 28 hours. The mixture was concentrated and the residue was purified by silica gel flash chromatography eluting with a methanol-ethyl acetate gradient to give tert-butyl (S)-4-(((((2R,3R,4R,5R)-3,4-bis((tert-butyldimethylsilyl)oxy)-5-(6-(((4-methoxyphenyl)diphenylmethyl)amino)-9H-purin-9-yl)tetrahydrofuran-2-yl)methyl)(2-(1-((2S,4S,5R)-4-hydroxy-5-(hydroxymethyl)tetrahydrofuran-2-yl)-4-(((4-methoxyphenyl)diphenylmethyl)amino)-2-oxo-1,2-dihydropyrimidin-5-yl)ethyl)amino)-2-((tert-butoxycarbonyl)amino)butanoate 54 (0.212 g, 83% yield). $R_f$=0.48 (100% ethyl acetate). $^1$H NMR (500 MHz, MeOD) δ8.08 (s, 1H), 7.89 (s, 1H), 7.73 (s, 1H), 7.39-7.03 (m, 24H), 6.84-6.66 (m, 4H), 6.05 (t, J=6.5 Hz, 1H), 5.81 (d, J=6.3 Hz, 1H), 4.97 (dd, J=6.4, 4.4 Hz, 1H), 4.29 (dt, J=6.4, 3.8 Hz, 1H), 4.25-4.13 (m, 2H), 4.04-3.92 (m, 1H), 3.84 (q, J=3.6 Hz, 1H), 3.78-3.64 (m, 2H), 3.73 (s, 3H), 3.70 (s, 3H), 3.08 (dd, J=14.2, 8.8 Hz, 1H), 2.92-2.70 (m, 3H), 2.68-2.46 (m, 4H), 2.21 (ddd, J=13.4, 6.2, 3.8 Hz, 1H), 2.00 (dt, J=13.4, 6.6 Hz, 1H), 1.94-1.79 (m, 1H), 1.71-1.55 (m, 1H), 1.41 (s, 9H), 1.40 (s, 9H), 0.97 (s, 9H), 0.73 (s, 9H), 0.14 (s, 3H), 0.14 (s, 3H), −0.07 (s, 3H), −0.40 (s, 3H). $^{13}$C NMR (126 MHz, MeOD) δ173.39, 159.89, 159.74, 157.93, 156.89, 155.58, 153.03, 149.91, 146.45, 146.39, 142.18, 139.83, 138.44, 137.96, 131.59, 131.47, 130.16, 128.69, 127.81, 127.62, 122.50, 114.02, 108.53, 90.53, 88.72, 87.45, 85.64, 82.68, 80.54, 76.11, 75.13, 72.55, 72.50, 71.86, 62.71, 57.77, 55.73, 54.83, 54.29, 52.34, 49.00, 41.92, 29.62, 28.83, 28.39, 27.64, 26.53, 26.29, 19.00, 18.78, −3.89, −4.04, −4.24, −5.04. HRMS (m/z) calcd. for $C_{86}H_{113}N_{10}O_{13}$ [M+H]$^+$ 1549.8033, found 1549.8027.

Tetrabutylammonium fluoride (0.297 mL of a 1M solution in tetrahydrofuran, 0.297 mmol) was added to a solution of 54 (0.200 g, 0.129 mmol) in dry tetrahydrofuran (5 mL) and the reaction was stirred at room temperature for 16 hours. The mixture was concentrated and the residue was purified by silica gel flash chromatography eluting with a methanol-ethyl acetate gradient to give tert-butyl (S)-2-((tert-butoxycarbonyl)amino)-4-((((2R,3S,4R,5R)-3,4-dihydroxy-5-(6-(((4-methoxyphenyl)diphenylmethyl)amino)-9H-purin-9-yl)tetrahydrofuran-2-yl)methyl)(2-(1-((2S,4S,5R)-4-hydroxy-5-(hydroxymethyl)tetrahydrofuran-2-yl)-4-(((4-methoxyphenyl)diphenylmethyl)amino)-2-oxo-1,2-dihydropyrimidin-5-yl)ethyl)amino)butanoate 55 (0.242 g, 83% yield). $R_f$=0.26 (5% ethanol/ethyl acetate). $^1$H NMR (500 MHz, MeOD) δ8.13 (s, 1H), 7.88 (s, 1H), 7.78 (s, 1H), 7.40-7.02 (m, 24H), 6.83-6.66 (m, 4H), 6.06 (t, J=6.4 Hz, 1H), 5.80 (d, J=3.7 Hz, 1H), 4.56 (dd, J=5.4, 3.7 Hz, 1H), 4.30 (dt, J=6.3, 3.9 Hz, 1H), 4.22-4.14 (m, 1H), 4.14-4.06 (m, 1H), 4.07-3.99 (m, 1H), 3.84 (q, J=3.6 Hz, 1H), 3.80-3.65 (m, 2H), 3.71 (s, 3H), 3.68 (s, 3H), 2.99-2.90 (m, 1H), 2.90-2.77 (m, 2H), 2.78-2.68 (m, 1H), 2.68-2.52 (m, 4H), 2.27-2.17 (m, 1H), 2.04 (dt, J=13.4, 6.6 Hz, 1H), 1.94-1.83 (m, 1H), 1.71-1.58 (m, 1H), 1.39 (s, 18H). $^{13}$C NMR (126 MHz, MeOD) δ173.62, 163.73, 159.89, 159.76, 158.00, 156.98, 155.39, 153.05, 149.60, 146.46, 146.43, 146.05, 141.14, 139.94, 138.42, 138.14, 131.54, 131.49, 130.17, 130.12, 128.74, 128.70, 127.82, 127.64, 122.01, 114.11, 114.02, 108.37, 91.20, 88.70, 87.45, 83.66, 82.73, 80.60, 74.71, 73.55, 72.46, 72.36, 71.80, 62.68, 57.83, 55.74, 55.01, 54.24, 52.37, 41.93, 29.57, 28.83, 28.38, 27.56, 0.00. HRMS (m/z) calcd. for $C_{74}H_{85}N_{10}O_{13}$ [M+H]$^+$ 1321.6298, found 1321.6289.

55 (139 mg, 0.105 mmol) was dissolved in a 1:1 mixture of 1,4-dioxane/water (28 mL). Dowex 50WX8-H$^+$ ion exchange resin (2.8 g) was added and the reaction mixture stirred at room temperature for 48 hours. The resin was filtered and washed with dioxane (10 mL) then water (10 mL). The product was released from the resin by washing with 0.2M aqueous ammonium hydroxide (250 mL) and then concentrated and finally freeze-dried. The residue was then purified using a Sep-Pak® Plus C18 environmental cartridge eluting with a water-methanol gradient to give (S)-2-amino-4-((2-(4-amino-1-((2S,4S,5R)-4-hydroxy-5-(hydroxymethyl)tetrahydrofuran-2-yl)-2-oxo-1,2-dihydropyrimidin-5-yl)ethyl)(((2R,3S,4R,5R)-5-(6-amino-9H-purin-9-yl)-3,4-dihydroxytetrahydrofuran-2-yl)methyl)amino)butanoic acid 56 (43 mg, 66% yield) as a white solid after freeze-drying. $^1$H NMR (500 MHz, D$_2$O) δ8.21 (s, 1H), 8.10 (s, 1H), 7.41 (s, 1H), 6.03 (t, J=6.5 Hz, 1H), 5.95 (d, J=5.4 Hz, 1H), 4.94 (t, J=5.3 Hz, 1H), 4.37-4.22 (m, 3H), 3.92 (q, J=4.3 Hz, 1H), 3.78 (t, J=6.2 Hz, 1H), 3.72 (dd, J=12.5, 3.3 Hz, 1H), 3.62 (dd, J=12.5, 4.6 Hz, 1H), 3.28-3.05 (m, 2H), 3.07-2.92 (m, 3H), 2.93-2.80 (m, 1H), 2.43-2.24 (m, 3H), 2.20-2.08 (m, 1H), 2.09-1.93 (m, 2H). $^{13}$C NMR (126 MHz, D$_2$O) δ173.86, 164.68, 156.43, 155.45, 152.80, 148.67, 140.73, 138.22, 119.06, 104.80, 88.56, 86.57, 85.89, 81.56, 72.20, 70.07, 60.76, 54.76, 53.92, 51.59, 51.15, 39.60, 26.17, 22.56. HRMS (m/z) calcd. for $C_{25}H_{37}N_{10}O_9$ [M+H]$^+$ 621.2745, found 621.2737.

Example 7: Synthesis of 2-amino-5-[[[4-amino-1-[(2R,4S,5R)-4-hydroxy-5-(hydroxymethyl)tetrahydrofuran-2-yl]-2-oxo-pyrimidin-5-yl]methylamino]methyl]-6-[(2R,3S,4R,5R)-5-(6-aminopurin-9-yl)-3,4-dihydroxy-tetrahydrofuran-2-yl]hexanoic acid 70

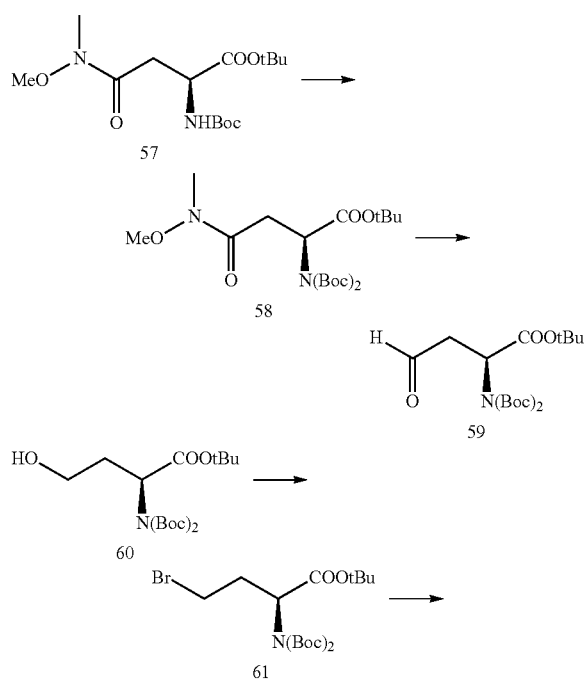

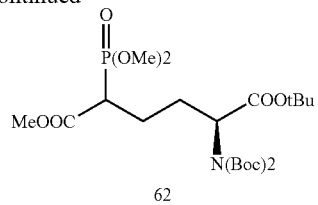

To tert-butyl L-2-(tert-butoxycarbonylamino)-4-[methoxy(methyl)amino]-4-oxo-butanoate 57 (Roberts, S. J., Morris, J. C., Dobson, R. C. J., Baxter, C. L., Gerrard, J. A., ARKIVOC 2004, 166-177) (15.15 g, 45.6 mmol) in dry tetrahydrofuran (250 mL) was added sodium hydride (60% in oil, 1.82 g, 45.6 mmol) and the mixture was stirred for 15 minutes. To this was added Boc anhydride (49.6 g, 23 mmol) and the mixture was heated under reflux for 4 hours and then cooled to room temperature. The product was diluted with water, extracted with dichloromethane and the organic phase was washed with water, brine, dried over magnesium sulfate, filtered and evaporated onto silica gel. Purification by dry flash column chromatography eluting with hexanes, 20% and 30% ethyl acetate gave tert-butyl 2-[bis(tert-butoxycarbonyl)amino]-4-[methoxy(methyl)amino]-4-oxo-butanoate 58 (16, 7 g, 85%) as an oil. $^1$H NMR (500 MHz, CDCl$_3$) δ5.45 (m, 1H), 3.70 (s, 3H), 3.44-2.70 (m, 2H), 3.18 (s, 3H), 1.55 (s, 9H), 1.51 (s, 9H), 1.44 (s, 9H). $^{13}$C NMR (125 MHz, CDCl$_3$) δ169.4, 152.4, 82.9, 81.8, 61.2, 55.6, 33.2, 28.0, 27.9. HRMS (m/z): calcd. for $C_{20}H_{36}N_2O_8$ [M+Na]$^+$ 455.2369, found 455.2365.

To a stirred solution of tert-butyl L-2-[bis(tert-butoxycarbonyl)amino]-4-[methoxy(methyl)amino]-4-oxo-butanoate 58 (16.7 g, 38.6 mmol) in dry tetrahydrofuran (400 mL) at −78° C. under Argon was added dropwise diisobutylaluminiumhydride (0.8 M in cyclohexane, 115.8 mmol, 145 mL) so the T<−70° C. The reaction was stirred at −78° C. for 1 hour and then poured into cold 0.35M potassium hydrogen sulfate and extracted with diethyl ether. The ether extract was washed with 1N hydrochloric acid, saturated aqueous sodium bicarbonate and brine. The solution was filtered through celite and the organic phase was dried over magnesium sulfate, filtered and evaporated onto silica gel. Purification by dry flash column chromatography eluting with hexanes-ethyl acetate gradient gave tert-butyl L-2-[bis(tert-butoxycarbonyl)amino]-4-oxo-butanoate 59 (12.8 g, 89%) as an oil. $^1$H NMR (500 MHz, CDCl$_3$) δ9.78 (s, 1H), 5.42-5.39 (m, 1H), 3.39-2.73 (m, 2H), 1.51 (s, 18H), 1.48 (s, 9H). $^{13}$C NMR (125 MHz, CDCl$_3$) δ198.8, 168.6, 152.1, 83.3, 82.1, 53.8, 44.6, 28.0, 27.9. HRMS(m/z) calcd. for $C_{18}H_{31}NO_7$ [M+Na]$^+$ 396.1998, found 396.2001.

To a solution of 59 (12.8 g, 34.2 mmol) in methanol (200 mL) was added sodium borohydride (1.3 g, 34.2 mmol) and the mixture was stirred at room temperature for 60 minutes. The reaction was diluted with diethyl ether and water and the organic phase was washed with 1N hydrochloric acid, saturated aqueous sodium bicarbonate, brine and dried over magnesium sulfate. After filtration and concentration under vacuum, the residue was evaporated onto silica gel and purification by dry flash column chromatography eluting with hexanes-ethyl acetate gradient gave tert-butyl 2-[bis(tert-butoxycarbonyl)amino]-4-hydroxy-butanoate 60 (9.27 g) as an oil. This product was dissolved in dry dichloromethane (250 mL) with carbon tetrabromide (9.8 g, 29.6 mmol) and cooled to 0° C. To this mixture was added slowly a solution of triphenyl phosphine (7.76 g, 29.6 mmol) in dry dichloromethane (100 mL) so the T<5° C. and then stirred at room temperature for 30 minutes. The mixture was evaporated to a small volume under vacuum at room temperature and applied to a dry flash chromatography column that was eluted with hexanes-ethyl acetate gradient to give tert-butyl 2-[bis(tert-butoxycarbonyl)amino]-4-bromo-butanoate 61 (9.46 g, 87%) as an oil. $^1$H NMR (500 MHz, CDCl$_3$) δ4.97-4.93 (m, 1H), 3.55-3.39 (m, 2H), 2.69-2.62 (m, 2H), 1.51 (s, 18H), 1.46 (s, 9H). $^{13}$C NMR (125 MHz, CDCl$_3$) δ169.1, 152.2, 83.1, 81.7, 57.5, 33.2, 30.3, 28.0, 27.9. HRMS(m/z) calcd. for $C_{18}H_{32}NO_6Br$ [M+Na]$^+$ 460.1311, found 460.1313.

Trimethyl phosphonoacetate (9.4 mL, 64.74 mmol) was added slowly to a stirred suspension of sodium hydride (3.1 g, 77.69 mmol) in dry dimethyl sulfoxide (80 mL) under Argon and the mixture was stirred at room temperature for 70 minutes. A solution of tert-butyl L-2-[bis(tert-butoxycarbonyl)amino]-4-bromo-butanoate 61 (21.58 mmol, 9.46 g) in dry dimethyl sulfoxide (25 mL) was added and the reaction was stirred for 4 hours at room temperature. The mixture was poured into water (300 mL), extracted with diethyl ether and the organic phase was washed with brine, dried over magnesium sulfate, filtered and evaporated. Purification by dry flash column chromatography eluting with hexanes-ethyl acetate gradient gave O-1-tert-butyl-O-6-methyl L-2-[bis(tert-butoxycarbonyl)amino]-5-dimethoxyphosphoryl-hexanedioate 62 (7.3 g, 62%) as an oil. $^1$H NMR (500 MHz, CDCl$_3$) δ4.74-4.68 (m, 1H), 3.81-3.74 (m, 9H), 3.12-2.95 (m, 1H), 2.18-1.83 (m, 4H), 1.51(s, 18H), 1.44(s, 9H). $^{13}$C NMR (125 MHz, CDCl$_3$) δ169.2, 152.3, 82.9, 81.4, 58.6, 58.0, 53.4, 53.2, 52.5, 45.3, 45.0, 44.3, 43.9, 28.0, 27.9, 24.3, 23.9. $^{31}$P NMR (202 MHz, CDCl$_3$): δ24.9. HRMS(m/z) calcd. for $C_{23}H_{42}NO_{11}P$ [M+Na]$^+$ 562.2393, found 562.2393.

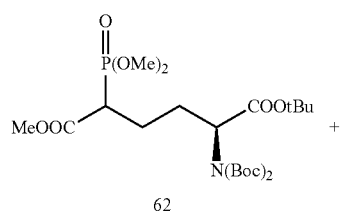

62

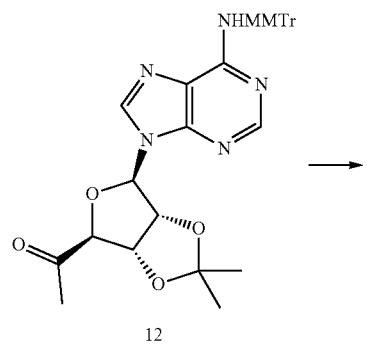

12

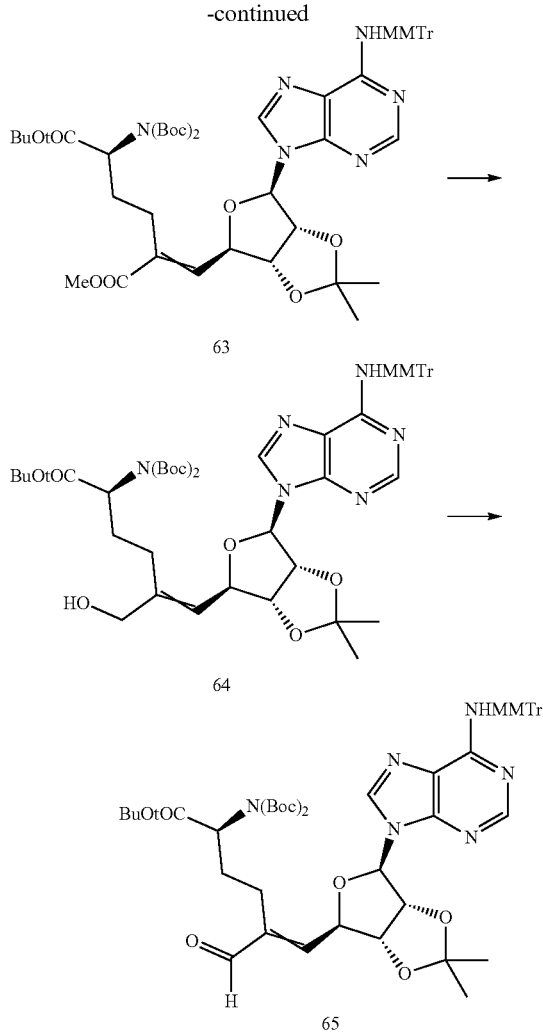

63

64

65

To a solution of the phosphonate 62 (4 mmol, 2.19 g) in dry tetrahydrofuran (50 mL) cooled in an ice bath was added sodium hydride (60%, 160 mg, 4 mmol) and after 15 minutes stirring in the ice bath the aldehyde 12 (see Example 3) (2.3 g, 4 mmol) [dried from benzene as described above] in dry tetrahydrofuran (20 mL) was added. The reaction was stirred in the ice bath for 30 minutes and then saturated aqueous ammonium chloride was added and the product was extracted with dichloromethane, washed with brine dried over magnesium sulfate and evaporated. Purification by silica gel chromatography eluting with hexanes-ethyl acetate gradient gave O-1-tert-butyl O-6-methyl 5-[[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]methylene]-2-[bis(tert-butoxycarbonyl)amino]hexanedioate 63 (2.43 g, 61%) as a gum that was a mixture of E/Z isomers. $^1$H NMR (500 MHz, CDCl$_3$) δ8.13-8.03 (m, 1H), 7.85-7.79 (m, 1H), 7.36-7.18 (m, 11H), 6.94-6.76 (m, 3.5H), 6.06-6.01 (m1.5H), 5.57-5.44 (m, 1H), 5.05-4.90 (m, 2H), 4.76-4.65 (m, 1H), 3.79-3.61 (m, 6H), 2.48-1.83 (m, 4H), 1.52-1.33 (m, 33H). $^{13}$C NMR (125 MHz, CDCl$_3$) δ170.1, 167.1, 158.6, 154.1, 152.6, 148.2, 145.5, 149.5, 138.0, 137.4, 135.1, 134.2, 131.0, 130.3, 129.2, 127.8, 127.1, 121.7, 114.7, 114.4, 113.2, 91.0, 86.3, 85.2, 84.5, 83.7, 82.8, 81.4, 71.2, 58.9, 58.4, 55.2, 51.9, 31.3, 29.3, 28.8, 28.0, 27.2, 25.4, 24.7. HRMS(m/z) calcd. for $C_{54}H_{67}N_6O_{12}$ [M+H]$^+$ 991.4817, found 991.4817.

To a solution of unsaturated ester 63 (830 mg, 0.84 mmol) in dry tetrahydrofuran (10 mL) cooled to −40° C. under Argon was added Diisobutylaluminum hydride solution (7.2 mL, 7 eq, 5.9 mmol, 0.8M in cyclohexane) slowly so the temperature stay at −35° C. and stirred at −40° C. for 2.5 hours. Then added saturated aqueous sodium acetate (25 mL) and the mixture was poured into saturated ammonium chloride (5 mL) and ethyl acetate (25 mL) and stirred for 1 hour and then filtered through celite. The organic phase was dried over magnesium sulfate, filtered and evaporated. Purification by silica gel chromatography eluting with hexanes-ethyl acetate gradient gave tert-butyl 6-[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]-2-[bis(tert-butoxycarbonyl)amino]-5-(hydroxymethyl)hex-5-enoate 64 (375 mg, 46%) as a gum. This alcohol was dissolved in dry dichloromethane (20 mL) and treated with Dess Martin periodinane (199 mg, 0.47 mmol, 1.2 eq) and the mixture was stirring at room temperature for 1 hour. A mixture of saturated aqueous sodium thiosulfate (12.5 mL) and sodium bicarbonate (25 mL) was added and then stirred vigorously for 1 hour. The product was extracted with dichloromethane, dried over magnesium sulfate, filtered and evaporated. Purification by silica gel chromatography eluting with hexanes-ethyl acetate gradient gave tert-butyl 6-[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]-2-[bis(tert-butoxycarbonyl)amino]-5-formyl-hex-5-enoate 65 as a foam (235 mg, 63%) as a foam. [Mixture of E/Z isomers] HRMS (m/z) calcd. for $C_{53}H_{65}N_6O_{12}$ [M+H]$^+$ 961.4711, found 961.4711.

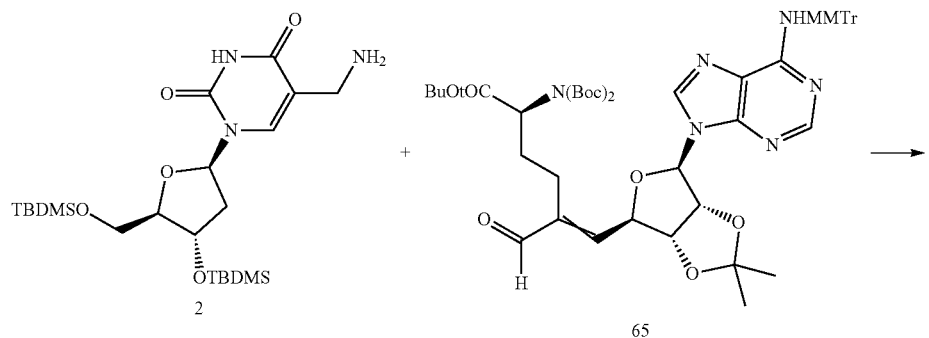

65

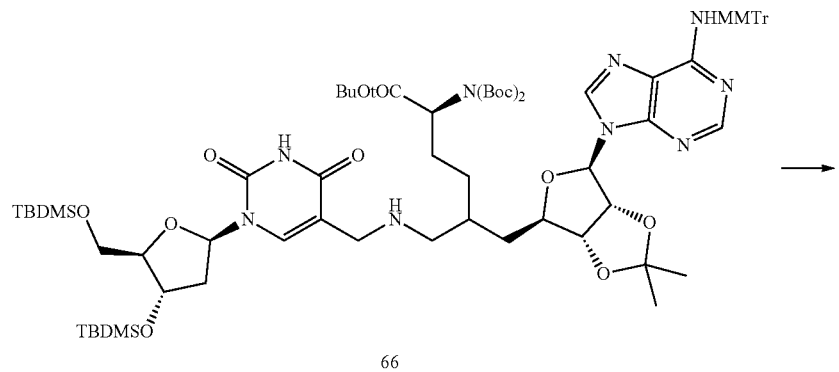

66

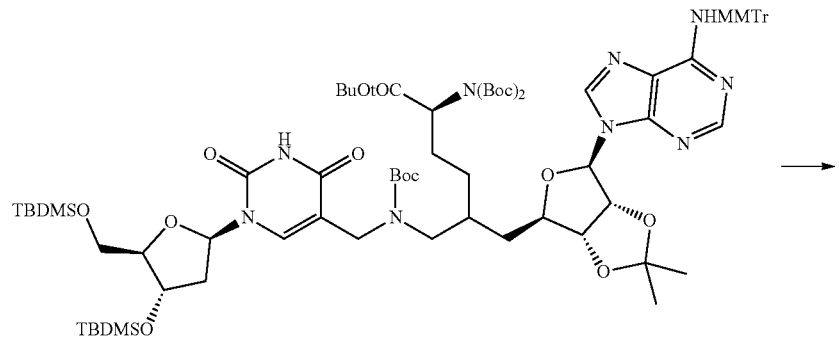

67

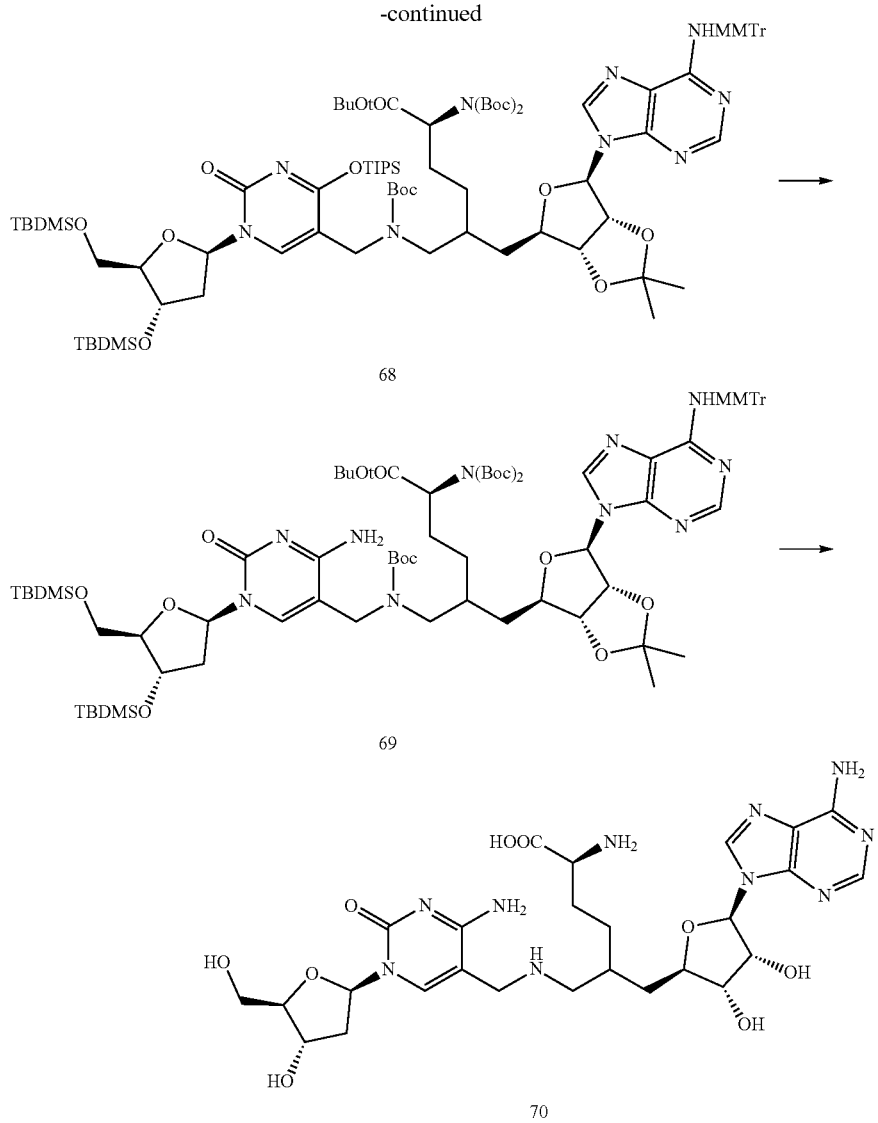

To the aldehyde 65 (190 mg, 0.2 mmol) in absolute ethanol (3 mL) was added the amine 2 (see Example 1) (115 mg, 0.23 mmol, 1.2 eq) and the pH of the mixture was adjusted to 6-7 with acetic acid. Picoline-borane complex (42.4 mg, 2 eq) was added and the mixture stirred for 48 hours. The residue was evaporated onto silica gel and purified by silica gel chromatography eluting with hexane-ethyl acetate gradient followed by 5% 7M methanolic ammonia in dichloromethane to give tert-butyl 5-[[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]methyl]-2-[bis(tert-butoxycarbonyl)amino]-6-[[1-[(2R,4S,5R)-4-[tert-butyl(dimethyl)silyl]oxy-5-[[tert-butyl(dimethyl)silyl]oxymethyl]tetrahydrofuran-2-yl]-2,4-dioxo-pyrimidin-5-yl]methylamino]hexanoate 66 (180 mg, 63%) as a foam. $^1$H NMR (500 MHz, CDCl$_3$) δ8.00-7.75 (m, 2H), 7.5-6.67 (m, 14H), 6.21-6.13 (m, 1H), 5.98-5.93 (m, 1H), 5.57-5.14 (m, 1H), 4.89-4.52 (m, 2H), 4.35-4.28 (m, 1H), 4.16-3.81 (m, 2H), 3.76-3.64 (m, 5H), 3.41-3.25 (m, 2H), 2.52-2.34 (m, 2H), 2.24-1.89 (2H), 1.49-1.25 (m, 39H), 0.87-0.81 (m, 18H), 0.08-0.05 (m, 12H). $^{13}$C NMR (125 MHz, CDCl$_3$) δ174.8, 169.7, 163.2, 158.3, 154.1, 152.4, 149.9, 148.5, 145.2, 138.9, 137.4, 130.4, 129.0, 127.9, 126.9, 121.3, 115.0, 113.2, 89.3, 87.9, 86.3, 84.1, 82.7, 81.1, 72.4, 71.0, 63.1, 59.0, 55.2, 46.7, 41.1, 28.9, 28.3, 28.0, 27.9, 27.2, 25.9, 25.7, 25.4, 21.5, 18.4, 18.0. HRMS(m/z) calcd. for C$_{75}$H$_{110}$N$_9$O$_{15}$Si$_2$ [M+H]$^+$ 1432.7660, found 1432.7651.

To 66 (516 mg, 0.36 mmol) in methanol (15 mL) was added Boc anhydride (94 mg, 0.43 mmol) and the mixture was stirred at room temperature for 1 hour. Concentration under vacuum gave tert-butyl 5-[[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]methyl]-2-[bis(tert-butoxycarbonyl)amino]-6-[tert-butoxycarbonyl-[[1-[(2R,4S,5R)-4-[tert-butyl(dimethyl)silyl]oxy-5-[[tert-butyl(dimethyl)silyl]oxymethyl]tetrahydrofuran-2-yl]-2,4-dioxo-pyrimidin-5-yl]methyl]amino]hexanoate 67 (550 mg) as a gum directly engaged in the next reaction. The crude 67 (115 mg, 0.075 mmol) in dichloromethane (1 mL) was vigorously stirred with 0.1M aqueous sodium carbonate (2 mL), tetrabutylammonium bromide (24 mg, 0.075 mmol) and tri-isopropylbenzene-sulfonyl chloride (340 mg 1.13 mmol) overnight. The mixture was extracted with dichloromethane, washed with sodium bicarbonate, brine, dried over magnesium sulfate, filtered and evaporated. Purification by silica gel chromatography eluting with hexanes-ethyl acetate gradient gave tert-butyl 5-[[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]methyl]-2-[bis(tert-butoxycarbonyl)amino]-6-[tert-butoxycarbonyl-[[1-[(2R,4S,5R)-4-[tert-butyl(dimethyl)silyl]oxy-5-[[tert-butyl(dimethyl)silyl]oxymethyl]tetrahydrofuran-2-yl]-2-oxo-4-(2,4,6-triisopropylphenyl)sulfonyloxy-pyrimidin-5-yl]methyl]amino]hexanoate 68 (55 mg, 40%) as a gum. The crude sulfonate 68 (134 mg, 0.074 mmol) was dissolved in dry dioxane (5 mL) and attached to a balloon filled with ammonia gas and stirred at room temperature for 2 hours. The solvent was evaporated and the product purified by silica gel chromatography eluting with hexanes-ethyl acetate gradient then 5% of 7M $NH_3$ in methanol-dichloromethane to give tert-butyl 5-[[(3aR,4R,6R,6aR)-4-[6-[[(4-methoxyphenyl)-diphenyl-methyl]amino]purin-9-yl]-2,2-dimethyl-3a,4,6,6a-tetrahydrofuro[3,4-d][1,3]dioxol-6-yl]methyl]-6-[[6-amino-3-[(2R,4S,5R)-4-[tert-butyl(dimethyl)silyl]oxy-5-[[tert-butyl(dimethyl)silyl]oxymethyl]tetrahydrofuran-2-yl]-2-oxo-1,6-dihydropyrimidin-5-yl]methyl-tert-butoxycarbonyl-amino]-2-[bis(tert-butoxycarbonyl)amino]hexanoate 69 (43 mg, 38%) as a gum. (Rotamers of Boc) $^1$H NMR (500 MHz, $CDCl_3$) δ8.10-8.02 (m, 1H), 7.86-7.78 (m, 1H), 7.59-6,75 (m, 14H), 6.25-6.14 (m, 1H), 5.99-5.92 (m, 1H), 5.39-5.21 (m, 1H), 4.71-3.89 (m, 7H), 3.84-3.58 (m, 5H), 3.07-2.85 (m, 4H), 2.56-1.91 (m, 2H), 1.83-1.15 (m, 39H), 0.94-0.74 (m, 18H), 0.15-0.02 (m, 12H). $^{13}$C NMR (125 MHz, $CDCl_3$) δ169.5, 169.1, 164.5, 164.3, 158.3, 157.3, 157.0, 155.6, 155.5, 154.1, 152.6, 152.5, 148.3, 145.2, 145.1, 141.0, 140.9, 140.5, 139.2, 139.0, 138.9, 137.3, 130.2, 128.9, 127.8, 126.8, 121.4, 115.0, 114.8, 114.5, 113.1, 101.2, 101.0, 93.0, 90.9, 90.3, 89.8, 89.2, 88.2, 88.1, 88.0, 87.1, 86.9, 86.7, 85.3, 84.7, 84.4, 84.3, 84.1, 84.0, 83.8, 83.7, 82.8, 82.7, 82.0, 81.6, 81.4, 81.2, 81.1, 72.8, 72.4, 72.2, 71.0, 70.6, 70.5, 70.2, 68.9, 66.1, 66.0, 64.9, 64.4, 63.3, 63.0, 62.9, 62.5, 62.1, 59.1, 58.8, 55.2, 49.6, 49.4, 45.4, 44.8, 44.6, 42.2, 42.1, 36.0, 35.6, 33.0, 32.8, 28.9, 28.5, 28.3, 28.2, 27.9, 27.3, 27.2, −4.6, −4.9, −5.3, −5.5. HRMS (m/z) calcd. for $C_{80}H_{119}N_{10}O_{16}Si_2$ [M+H]$^+$ 1531.8344, found 1531.8346.

A solution of the cytosine derivative 69 (36 mg, 0.023 mmol) in tetrahydrofuran (2 mL) was treated with tetrabutylammonium fluoride hydrate (1M in THF, 70 μL, 0.07 mmol, 3 eq) for 4 hours a room temperature and then diluted with ethyl acetate, washed with water, brine dried over magnesium sulfate, filtered and evaporated. Purification with silica gel chromatography eluting with dichloromethane-7M $NH_3$ in methanol gradient followed by the treatment of the residue with cold TFA (0.2 mL) at room temperature for 1 hour and evaporation under high vacuum gave crude deprotected material. Purification by reverse phase $C_{18}$ chromatography eluting with water-methanol gradient gave 2-amino-5-[[[4-amino-1-[(2R,4S,5R)-4-hydroxy-5-(hydroxymethyl)tetrahydrofuran-2-yl]-2-oxo-pyrimidin-5-yl]methylamino]methyl]-6-[(2R,3S,4R,5R)-5-(6-aminopurin-9-yl)-3,4-dihydroxy-tetrahydrofuran-2-yl]hexanoic acid 70 (0.5 mg) TFA salt as a powder after freeze drying. $^1$H NMR (500 MHz, $CDCl_3$) δ8.46-8.33 (m, 3H), 6.17-6.07 (m, 2H), 4.66-4.60 (m, 2H), 4.43-3.69 (m, 10H), 3.25-3.12 (m, 2H), 2.53-1.48 (m, 9H). $^{13}$C NMR (125 MHz, $CDCl_3$) δ172.7, 158.98, 150.1, 148.6, 148.4, 148.2, 148.1, 144.8, 142.8, 96.8, 96.7, 89.2, 87.6, 87.2, 82.0, 81.1, 73.6, 73.4, 70.1, 60.8, 53.4, 50.9, 50.6, 43.6, 39.6, 34.5, 33.8, 32.7, 26.7, 26.2. HRMS (m/z) calcd. for $C_{26}H_{39}N_{10}O_9$ [M+H]$^+$ 635.2901, found 635.2896.

Example 8: (S)-2-amino-4-((5-(6-amino-3-((2R,4S,5R)-4-hydroxy-5-(hydroxymethyl)tetrahydrofuran-2-yl)-4-oxo-3,4-dihydro-1,3,5-triazin-1(2H)-yl)pentyl)(((2R,3S,4R,5R)-5-(6-amino-9H-purin-9-yl)-3,4-dihydroxytetrahydrofuran-2-yl)methyl)amino)butanoic acid 86

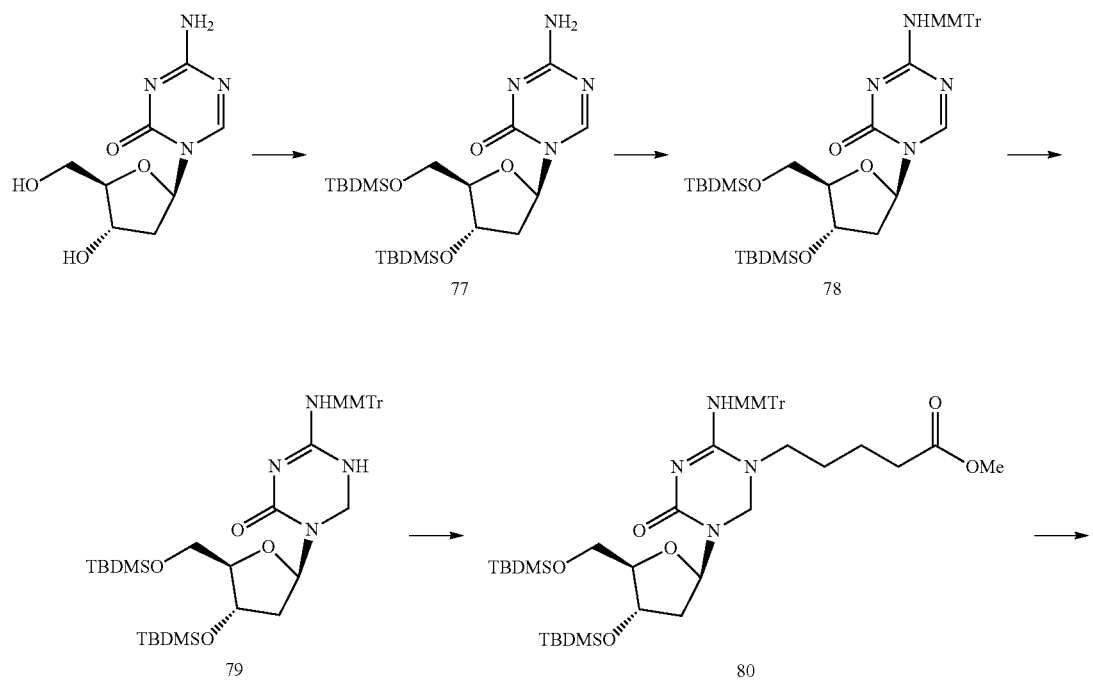

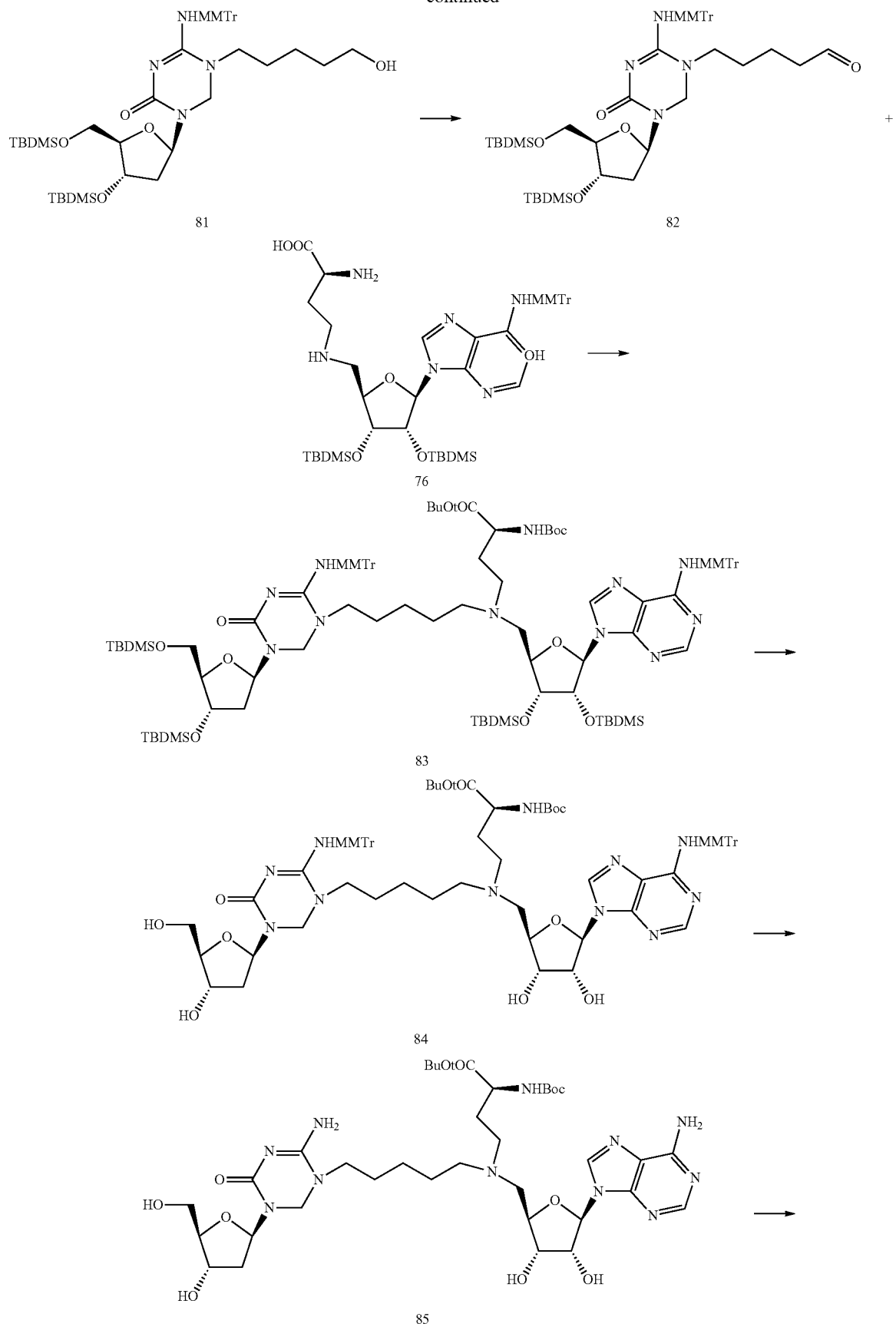

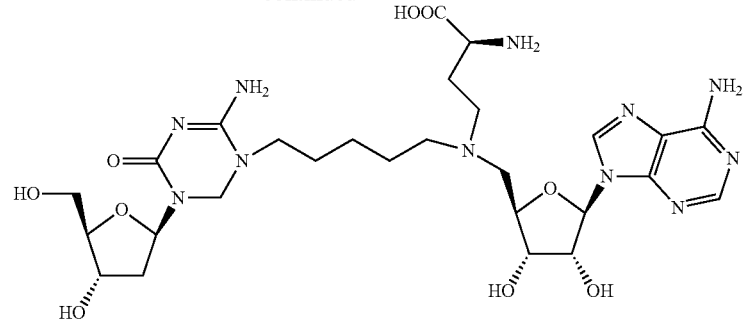

86

Commercially available 5-aza-2'-deoxycytidine (495 mg, 2.17 mmol), tert-butyldimethylsilyl chloride (1.3 g, 8.7 mmol, 4equiv.) and imidazole (0.901 g, 8.7 mmol, 4equiv.) were dissolved in dry N,N-dimethylformamide (7 mL). The reaction was stirred at room temperature, under argon, for 6 hours until TLC showed the reaction was complete. The reaction mixture was diluted with ethyl acetate (20 mL) and washed with water (3×10 mL), dried over anhydrous magnesium sulfate, filtered and concentrated in vacuo. The residue was purified by recrystallization in diethyl ether to afford 4-amino-1-((2R,4S,5R)-4-((tert-butyldimethylsilyl)oxy)-5-(((tert-butyldimethylsilyl)oxy)methyl)tetrahydrofuran-2-yl)-1,3,5-triazin-2(1H)-one 77 (0.990 g, quant.) as a white powder. $R_f$=0.50 (10% methanol/dichloromethane). $^1$H NMR (500 MHz, Chloroform-d) δ8.60 (s, 1H), 6.17 (dd, J=6.4, 5.1 Hz, 1H), 5.63 (s, 1H), 5.37 (s, 1H), 4.40 (dt, J=6.2, 4.8 Hz, 1H), 3.96 (dt, J=4.6, 2.4 Hz, 1H), 3.92 (dd, J=11.5, 2.8 Hz, 1H), 3.77 (dd, J=11.5, 2.2 Hz, 1H), 2.51 (ddd, J=13.5, 6.5, 5.2 Hz, 1H), 2.16 (ddd, J=13.5, 6.3, 5.0 Hz, 1H), 0.92 (s, 9H), 0.88 (s, 9H), 0.11 (s, 3H), 0.11 (s, 3H), 0.07 (s, 3H), 0.06 (s, 3H). $^{13}$C NMR (126 MHz, CDCl$_3$) 166.35, 162.49, 155.93, 87.99, 86.53, 70.54, 62.03, 42.55, 25.94, 25.70, 18.38, 17.95, −0.02, −4.59, −4.92, −5.49. HRMS (m/z) calcd. for $C_{20}H_{41}N_4O_4Si_2$ [M+H]$^+$ 457.2666, found 457.2661.

To a solution of 77 (568 mg, 1.24 mmol) in dry dichloromethane (15 mL) were added silver nitrate (846 mg, 4.97 mmol, 4 equiv.), sym-collidine (665 μL, 4.97 mmol, 4 equiv.) and 4-methoxytrityl chloride (1.59 g, 4.97 mmol, 4 equiv.). The reaction mixture was stirred at room temperature under argon overnight. The precipitate was filtered through celite and the filtrate washed with dichloromethane (20 mL). The organic layer was then washed with 5M citric acid (15 mL), sodium bicarbonate (15 mL), brine (15 mL), dried over magnesium sulfate, filtered and concentrated. The residue was purified by silica gel flash chromatography eluting with a petroleum ether-ethyl acetate gradient to afford 1-((2R,4S,5R)-4-((tert-butyldimethylsilyl)oxy)-5-(((tert-butyldimethylsilyl)oxy)methyl)tetrahydrofuran-2-yl)-4-(((4-methoxyphenyl)diphenylmethyl)amino)-1,3,5-triazin-2(1H)-one 78 (890 mg, 98% yield) as a pale yellow foam. $R_f$=0.62 (ethyl acetate/petroleum ether, 1/1). $^1$H NMR (500 MHz, DMSO-d$_6$, 90° C.) δ8.16 (s, 1H), 7.86 (s, 1H), 7.23-7.16 (m, 7H), 7.14-7.09 (m, 4H), 6.75 (d, J=8.9 Hz, 2H), 5.86 (t, J=6.3 Hz, 1H), 4.30 (q, J=4.8 Hz, 1H), 3.75 (q, J=3.8 Hz, 1H), 3.70 (dd, J=11.4, 3.9 Hz, 1H), 3.67 (s, 3H), 3.62 (dd, J=11.4, 3.8 Hz, 1H), 2.17-2.10 (m, 2H), 0.80 (s, 9H), 0.79 (s, 9H), −0.00 (s, 6H), −0.04 (s, 6H). $^{13}$C NMR (126 MHz, CDCl$_3$) δ170.92, 165.76, 163.69, 158.33, 158.30, 154.59, 154.38, 153.71, 152.63, 144.98, 144.89, 144.40, 137.02, 136.31, 130.24, 129.97, 128.99, 128.78, 128.64, 128.62, 128.19, 127.80, 127.67, 126.82, 125.27, 121.13, 113.10, 87.87, 87.64, 86.22, 86.14, 71.16, 70.76, 70.71, 70.15, 62.36, 61.79, 60.28, 55.11, 42.37, 42.23, 25.98, 25.89, 25.71, 20.97, 18.37, 18.25, 17.93, 14.20, −4.60, −4.89, −4.92, −5.41, −5.55, −5.61. HRMS (m/z) calcd. for $C_{40}H_{57}N_4O_5Si_2$ [M+H]$^+$ 729.3868, found 727.3867.

To a solution of 78 (350 mg, 0.48 mmol) in dry tetrahydrofurane (5 mL) and methanol (19 μL, 0.48 mmol, 1 equiv.) was added sodium borohydride (74 mg, 1.92 mmol, 4equiv.). The reaction was stirred at room temperature under argon for 5 minutes. The reaction mixture was then quenched with methanol (2 mL) and stirred for 30 minutes. The mixture was concentrated in vacuo and purified by silica gel flash chromatography eluting with a petroleum ether-ethyl acetate gradient to afford 1-((2R,4S,5R)-4-((tert-butyldimethylsilyl)oxy)-5-(((tert-butyldimethylsilyl)oxy)methyl)tetrahydrofuran-2-yl)-4-(((4-methoxyphenyl)diphenylmethyl)amino)-5,6-dihydro-1,3,5-triazin-2(1H)-one 79 (322 mg, 92% yield) as a colourless oil. $R_f$=0.39 (ethyl acetate/petroleum ether, 3/7). $^1$H NMR (500 MHz, DMSO-d$_6$) δ8.77 (s, 1H), 7.28-7.11 (m, 10H), 7.08 (d, J=8.8 Hz, 2H), 6.79 (d, J=9.0 Hz, 2H), 6.47 (s, 1H), 5.96 (dd, J=7.9, 6.4 Hz, 1H), 4.13 (dt, J=6.3, 3.3 Hz, 1H), 4.09-3.97 (ABq, J=11.6, 2H), 3.68 (s, 3H), 3.48 (td, J=4.6, 3.9, 2.7 Hz, 1H), 3.45 (d, J=5.4 Hz, 2H), 2.01-1.91 (m, 1H), 1.65 (ddd, J=13.1, 6.4, 3.5 Hz, 1H), 0.81 (s, 9H), 0.77 (s, 9H), −0.00 (d, J=1.6 Hz, 6H), −0.05 (s, 3H), −0.08 (s, 3H). $^{13}$C NMR (126 MHz, DMSO) δ158.01, 152.96, 147.07, 146.09, 145.99, 137.94, 130.27, 128.99, 128.96, 127.81, 126.69, 113.15, 85.49, 82.04, 72.24, 69.88, 63.04, 56.21, 55.43, 40.61, 40.52, 40.44, 40.35, 40.28, 40.18, 40.11, 40.02, 39.85, 39.68, 39.52, 35.82, 26.21, 26.12, 18.36, 18.12, −4.32, −4.49, −5.03, −5.11. HRMS (m/z) calcd. for $C_{40}H_{59}N_4O_5Si_2$ [M+H]$^+$ 731.4024, found 731.4024.

To a solution of 79 (506 mg, 0.69 mmol) in dry N,N-dimethylformamide (15 mL) was added sodium hydride (60 mass %) in oil (55 mg, 1.38 mmol, 2 equiv.) at 0° C. under argon. The reaction mixture was stirred for 20 minutes. Then, methyl 5-bromovalerate (210 μL, 1.38 mmol, 2 equiv.) was slowly added and the mixture stirred overnight at room temperature. The reaction mixture was cooled on ice-water bath then quenched with methanol (4 mL). The reaction mixture was diluted with ethyl acetate (30 mL), washed with water (15 mL), brine (15 mL), dried over magnesium sulfate, filtered and concentrated in vacuo. The residue was purified by silica gel flash chromatography eluting with a petroleum ether-ethyl acetate gradient to give methyl 5-(3-((2R,4S,5R)-4-((tert-butyldimethylsilyl)oxy)-

5-(((tertbutyldimethylsilyl)oxy)methyl)tetrahydrofuran-2-yl)-6-(((4-methoxyphenyl)diphenylmethyl)amino)-4-oxo-3,4-dihydro-1,3,5-triazin-1(2H)-yl)pentanoate 80 (240 mg, 41%) as a colourless oil. $R_f$=0.63 (ethyl acetate/petroleum ether, 3/7). $^1$H NMR (500 MHz, Chloroform-d) δ7.29-7.20 (m, 10H), 7.18-7.11 (m, 4H), 6.76 (d, J=9.0 Hz, 2H), 6.17 (dd, J=8.4, 6.0 Hz, 1H), 4.18 (dt, J=5.8, 2.8 Hz, 1H), 4.03-3.98 (m, 2H), 3.90 (dd, J=9.6, 2.7 Hz, 1H), 3.74 (s, 3H), 3.71 (dd, J=9.6, 2.8 Hz, 1H), 3.67 (q, J=2.9 Hz, 1H), 3.56 (m, 2H), 3.54 (s, 3H), 2.36-2.28 (m, 2H), 1.88 (dd, J=6.1, 3.0 Hz, 1H), 1.86 (dd, J=6.1, 2.8 Hz, 1H), 1.80 (dd, J=8.7, 6.6 Hz, 1H), 1.78-1.72 (m, 1H), 1.71-1.64 (m, 2H), 0.83 (s, 9H), 0.76 (s, 9H), 0.00 (s, 3H), −0.01 (s, 3H), −0.06 (s, 3H), −0.13 (s, 3H). $^{13}$C NMR (126 MHz, CDCl$_3$) δ174.08, 158.04, 153.67, 147.83, 147.77, 144.94, 139.21, 129.99, 128.79, 128.68, 127.95, 127.84, 126.42, 113.20, 86.12, 83.85, 77.32, 77.06, 76.81, 72.15, 71.40, 63.05, 55.14, 51.38, 48.89, 41.83, 37.99, 34.01, 27.83, 25.95, 25.85, 25.75, 22.59, 18.25, 17.96, −4.67, −4.83, −5.46, −5.64. HRMS (m/z) calcd. for $C_{46}H_{69}N_4O_7Si_2$ $[M+H]^+$ 845.4709, found 845.4705.

To a solution of 80 (240 mg, 0.28 mmol) in dry tetrahydrofurane (9 mL) and methanol (12 µL, 0.28 mmol, 1 equiv.) was added lithium borohydride (2.0 mol/L) in THF (1.1 mL, 2.27 mmol, 8 equiv.). The reaction was stirred at room temperature under argon overnight. The reaction mixture was then diluted with chloroform (15 mL) and washed with water (3×10 mL), dried over magnesium sulfate, filtered and concentrated in vacuo. The residue was purified by silica gel flash chromatography eluting with a petroleum ether-ethyl acetate gradient to give 1-((2R,4S,5R)-4-((tert-butyldimethylsilyl)oxy)-5-(((tert-butyldimethylsilyl)oxy)methyl)tetrahydrofuran-2-yl)-5-(5-hydroxypentyl)-4-(((4-methoxyphenyl)diphenylmethyl)amino)-5,6-dihydro-1,3,5-triazin-2(1H)-one 81 (174 mg, 75%) as a colourless oil. $R_f$=0.24 (ethyl acetate/petroleum ether, 1/1). $^1$H NMR (500 MHz, Chloroform-d) δ7.28-7.25 (m, 4H), 7.25-7.20 (m, 5H), 7.18-7.13 (m, 4H), 6.80-6.74 (m, 2H), 6.17 (dd, J=8.4, 6.0 Hz, 1H), 4.18 (dt, J=5.8, 2.7 Hz, 1H), 4.07-3.94 (m, 3H), 3.90 (dd, J=9.6, 2.7 Hz, 1H), 3.74 (s, 3H), 3.71 (dd, J=9.5, 2.8 Hz, 1H), 3.68 (q, J=3.1 Hz, 1H), 3.60-3.53 (m, 4H), 1.87 (ddd, J=13.1, 6.1, 2.8 Hz, 1H), 1.83-1.77 (m, 2H), 1.76-1.71 (m, 1H), 1.63-1.54 (m, 2H), 1.41 (tt, J=9.6, 6.4 Hz, 2H), 0.83 (s, 9H), 0.76 (s, 9H), −0.00 (s, 3H), −0.01 (s, 3H), −0.06 (s, 3H), −0.13 (s, 3H). $^{13}$C NMR (126 MHz, CDCl$_3$) δ158.05, 153.79, 147.88, 147.82, 144.93, 139.20, 130.00, 128.81, 127.81, 126.41, 113.20, 86.11, 83.87, 72.14, 71.40, 63.04, 62.94, 55.15, 48.93, 42.19, 37.98, 32.47, 27.91, 25.94, 25.84, 25.74, 23.21, 18.24, 17.95, −4.68, −4.84, −5.47, −5.64. HRMS (m/z) calcd. for $C_{45}H_{69}N_4O_6Si_2$ $[M+H]^+$ 817.4756, found 817.4750.

Compound 81 (37 mg, 0.045 mmol) and Dess-Martin periodinane (30 mg, 0.068 mmol, 1.5 equiv) were placed in the high vacuum for 1 hour then cooled on ice-water bath and dissolved with dry dichloromethane (3 mL) under argon. Then the reaction mixture was allowed to warm to room temperature and stirred for another 30 minutes until TLC showed the reaction was complete. The precipitate was filtered over celite, washed with dichloromethane (15 mL) and concentrated. The residue was then engaged into to next step without further purification. The aldehyde derivative 82 was then dissolved in dry methanol (3 mL) and a solution of 76 (46 mg, 0.045 mmol, 1 equiv.) in dry methanol (3 mL) was added. 2-picoline borane complex (9 mg, 0.091 mmol, 2 equiv.) was added and the mixture stirred at room temperature under argon for 5 hours. The reaction mixture had a pH-5-6. 2-picoline borane complex (9 mg, 0.091 mmol, 2 equiv.) was added again and the mixture stirred at room temperature under argon for 48 hours. The reaction mixture was concentrated, diluted in chloroform (7 mL), washed with saturated aqueous sodium bicarbonate (3 mL), dried over magnesium sulfate, filtered and concentrated in vacuo. The residue was then purified by silica gel flash column chromatography eluting with a petroleum ether ethyl acetate gradient to give tert-butyl (S)-4-((((2R,3R,4R,5R)-3,4-bis((tert-butyldimethylsilyl)oxy)-5-(6-(((4-methoxyphenyl)diphenylmethyl)amino)-9H-purin-9-yl)tetrahydrofuran-2-yl)methyl)(5-(3-((2R,4S,5R)-4-((tert-butyldimethylsilyl)oxy)-5-(((tert-butyldimethylsilyl)oxy)methyl)tetrahydrofuran-2-yl)-6-(((4-methoxyphenyl)diphenylmethyl)amino)-4-oxo-3,4-dihydro-1,3,5-triazin-1(2H)-yl)pentyl)amino)-2-((tert-butoxycarbonyl)amino)butanoate 83 (58 mg, 70%) as a colourless oil. $R_f$=0.41 (ethyl acetate/petroleum ether, 3/7). $^1$H NMR (500 MHz, Chloroform-d) δ8.00 (s, 1H), 7.84 (s, 1H), 7.36-7.31 (m, 4H), 7.31-7.28 (m, 4H), 7.26-7.14 (m, 17H), 6.88 (s, 1H), 6.78 (dd, J=8.9, 4.4 Hz, 4H), 6.21 (dd, J=8.3, 6.0 Hz, 1H), 5.80 (d, J=5.6 Hz, 1H), 5.50 (d, J=8.1 Hz, 1H), 4.97 (t, J=4.7 Hz, 1H), 4.21 (dt, J=5.9, 2.8 Hz, 1H), 4.12 (m, 3H), 4.05-3.96 (m, 2H), 3.93 (dd, J=9.6, 2.6 Hz, 1H), 3.77 (s, 3H), 3.76 (s, 3H), 3.75-3.72 (m, 1H), 3.70 (q, J=2.9 Hz, 1H), 3.59 (d, J=3.0 Hz, 2H), 2.92 (dd, J=13.8, 5.7 Hz, 1H), 2.71-2.59 (m, 2H), 2.55-2.45 (m, 2H), 2.39 (m, 1H), 1.90 (ddd, J=12.9, 6.1, 2.8 Hz, 2H), 1.82-1.65 (m, 2H), 1.54-1.45 (m, 1H), 1.40 (br s, 10H), 1.39 (s, 9H), 1.35-1.28 (m, 2H), 0.92 (s, 9H), 0.86 (br s, 11H), 0.79 (s, 9H), 0.75 (s, 9H), 0.09 (d, J=2.4 Hz, 6H), 0.03 (s, 3H), 0.02 (s, 3H), −0.03 (s, 3H), −0.10 (s, 3H), −0.34 (s, 3H). $^{13}$C NMR (126 MHz, CDCl$_3$) δ171.71, 171.07, 158.29, 158.02, 155.51, 154.24, 153.63, 152.04, 148.58, 147.93, 147.88, 145.32, 144.94, 140.00, 139.16, 137.42, 130.22, 129.99, 128.94, 128.79, 127.78, 126.76, 126.37, 122.12, 113.19, 113.10, 89.47, 86.06, 83.88, 83.82, 81.47, 79.30, 74.31, 73.48, 72.11, 71.36, 71.05, 63.03, 56.69, 55.18, 55.11, 54.74, 53.19, 50.91, 48.89, 42.42, 38.01, 35.43, 31.92, 31.58, 29.69, 29.65, 29.51, 29.35, 28.35, 28.31, 28.00, 26.70, 25.87, 25.84, 25.73, 25.25, 22.68, 18.23, 18.02, 17.95, 17.88, 14.09, 11.40, −0.02, −4.36, −4.45, −4.64, −4.68, −4.84, −5.26, −5.47, −5.65. HRMS (m/z) calcd. for $C_{100}H_{148}N_{11}O_{13}Si_4$ $[M+H]^+$ 1823.0335, found 1823.0326.

Tetrabutylammonium fluoride (254 µL of a 1M solution in tetrahydrofuran, 0.254 mmol, 8 equiv.) was added to a solution of 83 (22 mg, 0.032 mmol) in dry tetrahydrofuran (5 mL), the reaction was stirred at room temperature, under argon, overnight. The reaction mixture was concentrated in vacuo. The residue was diluted with dichloromethane (10 mL) and washed with water (3×5 mL), dried over magnesium sulfate, filtered and concentrated in vacuo. The residue was then purified by silica gel flash column chromatography eluting with a dichloromethane—methanol gradient to afford tert-butyl (S)-2-((tert-butoxycarbonyl)amino)-4-((((2R,3S,4R,5R)-3,4-dihydroxy-5-(6-(((4-methoxyphenyl)diphenylmethyl)amino)-9H-purin-9-yl)tetrahydrofuran-2-yl)methyl)(5-(3-((2R,4S,5R)-4-hydroxy-5-(hydroxymethyl)tetrahydrofuran-2-yl)-6-(((4-methoxyphenyl)diphenylmethyl)amino)-4-oxo-3,4-dihydro-1,3,5-triazin-1(2H)-yl)pentyl)amino)butanoate 84 (22 mg, 51%) as a colourless oil. $R_f$=0.26 (dichloromethane/methanol, 10/1). $^1$H NMR (500 MHz, Chloroform-d) δ8.19 (s, 1H), 8.00 (s, 1H), 7.44 (dd, J=8.4, 1.3 Hz, 1H), 7.34-7.16 (m, 25H), 6.86-6.75 (m, 4H), 6.08 (d, J=8.5 Hz, 1H), 6.00 (d, J=6.0 Hz, 1H), 4.81-4.66 (m, 1H), 4.45 (br s, 1H), 4.30 (br s, 1H), 4.23-4.15 (m, 2H), 4.08-4.03 (m, 1H), 3.94-3.84 (m, 2H), 3.79 (m, 1H), 3.77 (s, 3H), 3.76 (s, 3H), 3.59 (dd, J=11.7, 3.3 Hz, 1H), 3.51-3.43 (m, 1H), 2.89 (m, 1H), 2.72-2.59 (m, 2H), 2.51 (br s, 1H), 2.42 (br s, 1H), 2.36-2.16 (m, 1H), 2.13-2.07 (m, 1H), 1.98 (m, 1H), 1.82 (m, 1H), 1.71 (s, 1H), 1.65-1.54 (m, 2H), 1.45 (s, 9H), 1.43 (s, 9H). $^{13}$C NMR (126 MHz, CDCl$_3$) δ158.25, 158.13, 154.35, 154.04, 152.23, 145.11, 138.69, 138.68, 137.19, 130.29, 129.93, 128.98, 128.69, 128.48, 127.89, 127.75, 126.75, 126.56, 120.79, 113.26, 113.05, 88.57, 85.85, 85.45, 80.04, 74.14, 72.28, 71.87, 71.27, 71.09, 62.99, 58.86, 56.73, 55.21, 53.92, 52.82, 50.83, 41.92, 37.37, 31.92, 29.69, 28.36, 28.05, 25.51, 23.93, 23.76, 22.68, 19.70, 14.10, 13.59. HRMS (m/z) calcd. for C$_{76}$H$_{92}$N$_{11}$O$_{13}$ [M+H]$^+$ 1366.6876, found 1366.6869.

Compound 84 (80 mg, 0.059 mmol) was dissolved in aqueous acetic acid 70% (10 mL) and stirred at room temperature for 5 hours. The reaction mixture was then concentrated in vacuo and the residue purified by silica gel flash column chromatography eluting with a dichloromethane-methanol-aqueous ammonia (5:2:0.5) mixture to afford tert-butyl (S)-4-((5-(6-amino-3-((2R,4S,5R)-4-hydroxy-5-(hydroxymethyl)tetrahydrofuran-2-yl)-4-oxo-3,4-dihydro-1,3,5-triazin-1(2H)-yl)pentyl)(((2R,3S,4R,5R)-5-(6-amino-9H-purin-9-yl)-3,4-dihydroxytetrahydrofuran-2-yl)methyl)amino)-2-((tert-butoxycarbonyl)amino)butanoate 85 (41 mg, 85%) as a colourless oil. R$_f$=0.57 (dichloromethane-methanol-aqueous ammonia; 5/2/0.5). $^1$H NMR (500 MHz, Deuterium Oxide) δ8.29 (s, 1H), 8.23 (s, 1H), 6.07 (dd, J=8.0, 6.5 Hz, 1H), 6.01 (d, J=4.6 Hz, 1H), 4.46-4.34 (m, 2H), 4.30 (dd, J=6.8, 3.5 Hz, 1H), 4.26-4.20 (m, 2H), 3.88 (br s, 1H), 3.83 (dt, J=5.6, 3.9 Hz, 1H), 3.70 (dd, J=12.3, 4.0 Hz, 1H), 3.62 (dd, J=12.3, 5.6 Hz, 1H), 3.56-3.48 (m, 2H), 3.21-3.13 (m, 1H), 2.94-2.80 (m, 2H), 2.59 (t, J=7.6 Hz, 2H), 2.49 (t, J=7.8 Hz, 2H), 2.20 (ddd, J=14.5, 8.0, 6.7 Hz, 1H), 2.09-2.02 (m, 2H), 1.88 (br s, 1H), 1.73 (br s, 1H), 1.62 (q, J=8.2 Hz, 1H), 1.48 (p, J=7.5 Hz, 2H), 1.41-1.36 (m, 1H), 1.35 (s, 6H), 1.33 (s, 9H), 1.21 (dt, J=12.0, 7.4 Hz, 2H). $^{13}$C NMR (126 MHz, D$_2$O) δ174.72, 155.66, 154.91, 153.90, 152.89, 148.88, 140.34, 119.01, 88.28, 85.12, 83.86, 83.49, 72.99, 72.24, 70.91, 61.74, 55.71, 53.68, 53.20, 50.38, 48.91, 42.07, 35.59, 27.59, 27.39, 27.13, 24.88, 23.51, 20.54, 19.17, 13.28, 12.83. HRMS (m/z) calcd. for C$_{36}$H$_{60}$N$_{11}$O$_{11}$ [M+H]$^+$ 822.4474, found 822.4483.

Compound 85 (11 mg, 0.014 mmol) was diluted in a (3:1) mixture of TFA/water (1 mL) and stirred at room temperature for 10 minutes. The reaction mixture was then co-evaporated several times with water (6×10 mL), ethanol (30 mL) and water again (20 mL). The residue was then purified by Sep-Pak® Plus C18 environmental cartridge eluting with a water-methanol gradient to give (S)-2-amino-4-((5-(6-amino-3-((2R,4S,5R)-4-hydroxy-5-(hydroxymethyl)tetrahydrofuran-2-yl)-4-oxo-3,4-dihydro-1,3,5-triazin-1(2H)-yl)pentyl)(((2R,3S,4R,5R)-5-(6-amino-9H-purin-9-yl)-3,4-dihydroxytetrahydrofuran-2-yl)methyl)amino)butanoic acid 86 (4 mg, 45%) as a white solid. R$_f$ on RP-18=0.86 (water/methanol; 1/1). $^1$H NMR (500 MHz, Deuterium Oxide) δ8.37 (d, J=3.8 Hz, 2H), 6.13 (d, J=4.1 Hz, 1H), 6.09 (t, J=7.2 Hz, 1H), 4.84 (br s, 1H), 4.51-4.43 (m, 2H), 4.34 (dt, J=6.6, 3.5 Hz, 1H), 3.91 (dt, J=5.3, 3.6 Hz, 1H), 3.84-3.76 (m, 1H), 3.78-3.69 (m, 2H), 3.68-3.61 (m, 2H), 3.60-3.50 (m, 1H), 3.51-3.42 (m, 1H), 3.28-3.20 (m, 2H), 2.32 (dq, J=16.3, 8.0 Hz, 1H), 2.22 (ddd, J=14.3, 7.9, 6.5 Hz, 1H), 2.15 (ddd, J=14.2, 6.5, 3.6 Hz, 2H), 1.67 (br s, 2H), 1.55-1.43 (m, 2H), 1.32 (s, 1H), 1.25 (s, 1H). $^{13}$C NMR (126 MHz, D2O) δ172.85, 154.54, 151.13, 148.43, 142.48, 141.95, 119.41, 115.20, 89.80, 85.70, 84.50, 78.28, 72.72, 71.80, 70.76, 61.51, 54.75, 54.34, 52.80, 52.26, 48.73, 42.41, 35.76, 25.93, 24.91, 22.39, 21.98. HRMS (m/z) calcd. for C$_{27}$H$_{44}$N$_{11}$O$_9$ [M+H]$^+$ 666.3323, found 666.3326.

Example 9: shDNMT1 CD-fragment Expression and Purification for Kinetic Assays

Human DNMT1 C-terminal catalytic domain gene was codon-optimised for *E. coli* by DNA2.0. The gene was cloned into the pD431-SR vector, KanR resistance, inducible by IPTG. The codon-optimisation gave yields 5 to 10 times greater than previously published reports (e.g. Song, J., Rechkoblit, O., Bestor, T. H., and Patel, D. J., (2011) Science 331(6020): 1036-1040; and Song, 3., Teplova, M., Ishibe-Murakami, S., and Patel, D. J., (2012) Science 335 (6069): 709-712). The protein construct has N-terminal His-tag, a SUMO tag, a SUMO protease cleavage site, and the DNMT-catalytic domain.

For expression, the plasmid was transformed into BL21 Star or BL21 (DE3) pLysS cells. Both give similar results. Enzyme production was initiated from colonies selected from a fresh agar plate, instead of from frozen glycerol stocks. Cultures initiated from glycerol stocks gave poorer yields.

Growing the cells and the protein purification requires 4 days' preparation time. Minimising purification time improves yields. The procedure was initiated from fresh unfrozen cell pellets. The cell lysate was filtered using a Whatman #1 filter paper funnel prior loading to columns. The purification procedure has 4 major steps: Ni-NTA column, ULP1 cleavage, Heparin column, and size-exclusion column. FPLC is important as fine gradient control is required.

Filtered cell lysate supplemented with freshly prepared 1 mM DTT was pump loaded to a Ni-NTA column. Buffer A also requires fresh DTT, as the preparation requires large volume washes at 20 mM imidazole to remove unwanted proteins and reach baseline absorbance at 280 nm. Step gradients to 50 and 100 mM imidazole DNMT1 were followed by elution of DNMT1 near 150 mM imidazole. The pooled DNMT1 fractions included truncated fusion proteins of different lengths, and with a distinct full-length protein at >100 KDa. Subsequent cleavage by ULP1 can down-shift these protein molecular weights as indicated by SDS-PAGE.

The ULP1 cleavage was carried out on ice or in a cold room in the same imidazole elution buffer. Pooled proteins were stored in capped Falcon tubes to minimise oxygen exchange. All buffers were supplemented with 1 mM of fresh DTT. Test quantities of ULP1 were established as needed to complete the digestion overnight. The reaction was monitored by altered protein masses by SDS-PAGE.

Fully digested DNMT1 was furthered purified by Heparin column chromatography. Truncated proteins did not bind to heparin and were found in flow through. The full length protein was eluted by >500 mM NaCl. If the imidazole buffer had 250-300 mM NaCl, no dialysis was needed between the Ni-NTA and the heparin steps. Ideally, the protein was 95% pure after this step. Pooled DNMT1 fractions were concentrated by 50 KD molecular weight retention Amicon filtration.

Concentrated DNMT1 was loaded onto a gel-filtration column and the early main peak containing the large MW protein collected. The purified protein was stored in screw-cap tubes at −80° C.

Example 10: DNMT1 Inhibition Assay

DNMT1 inhibitors were assayed by measuring the transfer of radioactivity from tritiated S-adenosylmethionine (SAM) to double-stranded DNA (Du, Q., Z. Wang, Z., and Schramm, V. L., Proc. Natl. Acad. Sci. USA, 2016, 113, 2916-2921). The double stranded DNA molecule contains exactly one hemimethylated CpG located in the centre of the sequence. The design allows one methylation occurrence per DNA molecule, preventing any processive methylation along or across the strand.

[Me-$^3$H] S-Adenosyl methionine ([Me-$^3$H]-SAM) was enzymatically synthesized using bacterial chlorinase (SaIL) enzyme (Nat Chem Biol. 2008 Jan.; 4 (1):69-74. Epub 2007 Dec. 2. Discovery and characterization of a marine bacterial SAM-dependent chlorinase. Eustáquio AS[1], Pojer F, Noel J P, Moore B S.), starting from 5'-Chloro-5'-deoxyadenosine and L-[Methyl-$^3$H]-Methionine (Org Biomol Chem. 2016 Jul. 14; 14(26):6189-92. doi: 10.1039/c6ob00844e. Epub 2016 Jun. 6. Chemoenzymatic synthesis and utilization of a SAM analog with an isomorphic nucleobase. Vranken C[1], Fin A, Tufar P, Hofkens J, Burkart M D, Tor Y.). A reaction (500 µL) containing 500 µCi L-[Methyl-3H]-Methionine (PerkinElmer), 0.3 mM unlabeled methionine, 1 mM 5'-Chloro-5'-deoxyadenosine, 50 mM phosphate buffer pH 7.6 and 20 µM SaIL enzyme was incubated at room temperature. After 2 hours of incubation, reaction was stopped using 50 mM sulfuric acid. The [Me-$^3$H]-SAM was purified using C-18 reverse-phase HPLC using a gradient (buffer A: 50 mM ammonium acetate pH 4.3; buffer B: 0.1% acetic acid and 50% acetonitrile). The fractions containing [Me-$^3$H]-SAM were pooled and lyophilized overnight. Purified [Me-$^3$H]-SAM was always kept frozen at −80° C. until further use.

The DNMT1 assays were carried to determine the IC$_{50}$ with transition state analogs. The reaction (100 µL) containing 50 mM Tris-HCl pH 8.0, 100 mM KCl, 50 ug/mL BSA, 2 mM DTT, 1 µM freshly prepared [Me-3H]-SAM, 1 µM 26 bp hemimethylated DNA substrate and varying concentrations of each inhibitor (0-100 1 µM), incubated at 37° C. with 100 nM DNMT1. The reaction fractions (50 µL) were taken at 2 hours. The methylated DNA was purified by using Micro Bio-spin P-30 columns (Bio-Rad). Purified samples were mixed with 10 mL of scintillation liquid (PerkinElmer), and counted for radioactivity in a Tricarb 2910 TR scintillation counter (PerkinElmer). The values obtained in the absence of DNMT1 in the reaction were used as controls. The assay data were analyzed using GraphPad Prism for IC$_{50}$ calculations. The hemimethylated DNA sequences used in the assays contained 26 bp, as follows: 26a oligo 5'-CTACCTTGGTATCGATTGGTATGAGT-3' [SEQ ID No. 1], and 26bm oligo 5'-ACTCATACCAAT/iMe-dC/GATACCAAGGTAG-3' [SEQ ID No. 2], where iMe-dC is a 5-methyl-C base.

IC$_{50}$ values were obtained from plots of percent inhibition versus inhibitor concentration. The results are shown in Table 1.

TABLE 1

Inhibition of DNMT1

| Compound | Structure | IC$_{50}$(µM) |
|---|---|---|
| 7 | 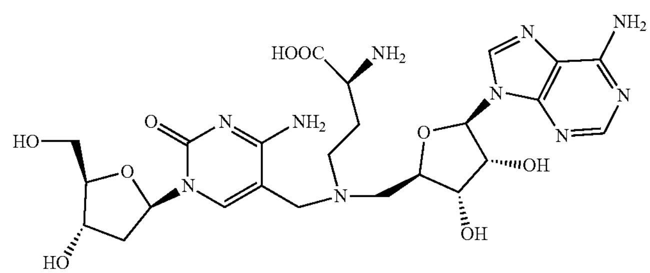 [SMILES: Nc1nc(=O)n([C@H]2C[C@H](O)[C@@H](CO)O2)cc1CN(CC[C@H](N)C(=O)O)C[C@H]1O[C@@H](n2cnc3c(N)ncnc32)[C@H](O)[C@@H]1O] | 0.7 ± 0.1 |
| 10 | 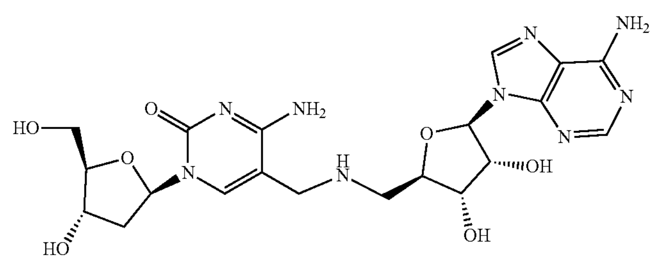 [SMILES: Nc1nc(=O)n([C@H]2C[C@H](O)[C@@H](CO)O2)cc1CNC[C@H]1O[C@@H](n2cnc3c(N)ncnc32)[C@H](O)[C@@H]1O] | 1.1 ± 0.2 |
| 21 | 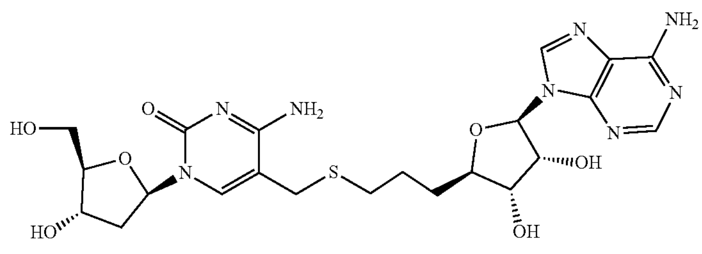 [SMILES: Nc1nc(=O)n([C@H]2C[C@H](O)[C@@H](CO)O2)cc1CSCCC[C@H]1O[C@@H](n2cnc3c(N)ncnc32)[C@H](O)[C@@H]1O] | 3.6 ± 0.2 22 |

TABLE 1-continued

Inhibition of DNMT1

| Compound | Structure | IC$_{50}$(μM) |
|---|---|---|
| 33 | 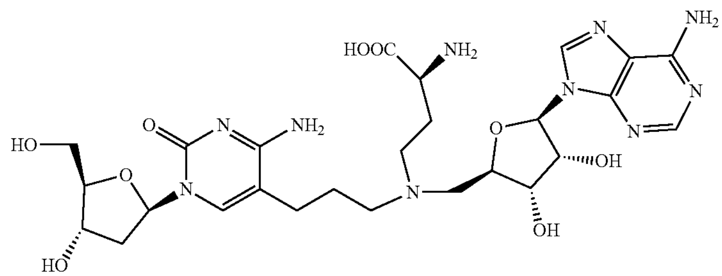 | 0.8 ± 0.1 |
| 42 | 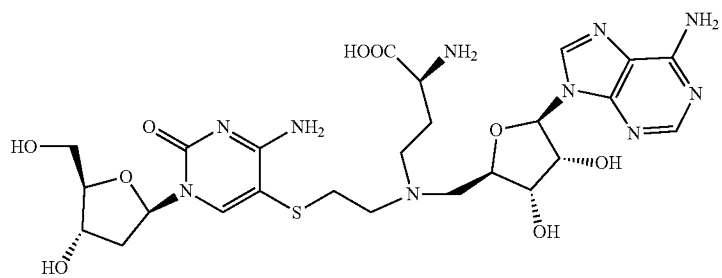 [SMILES: Nc1nc(=O)n([C@H]2C[C@H](O)[C@@H](CO)O2)cc1SCCN(CC[C@H](N)C(=O)O)C[C@H]1O[C@@H](n2cnc3c(N)ncnc32)[C@H](O)[C@@H]1O] | 15.4 ± 6.2 |
| 56 | 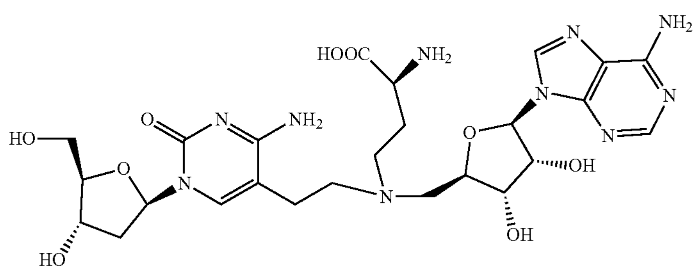 [SMILES: Nc1nc(=O)n([C@H]2C[C@H](O)[C@@H](CO)O2)cc1CCN(CC[C@H](N)C(=O)O)C[C@H]1O[C@@H](n2cnc3c(N)ncnc32)[C@H](O)[C@@H]1O] | 1.9 ± 0.1 |
| 70 | 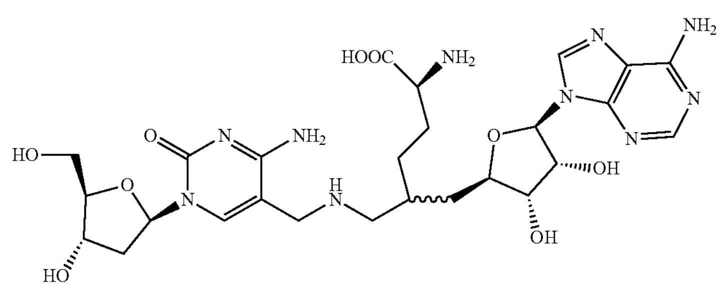 [SMILES: Nc1nc(=O)n([C@H]2C[C@H](O)[C@@H](CO)O2)cc1CNCC(CC[C@H](N)C(=O)O)C[C@H]1O[C@@H](n2cnc3c(N)ncnc32)[C@H](O)[C@@H]1O] | 2.2 ± 0.5 |
| 86 | 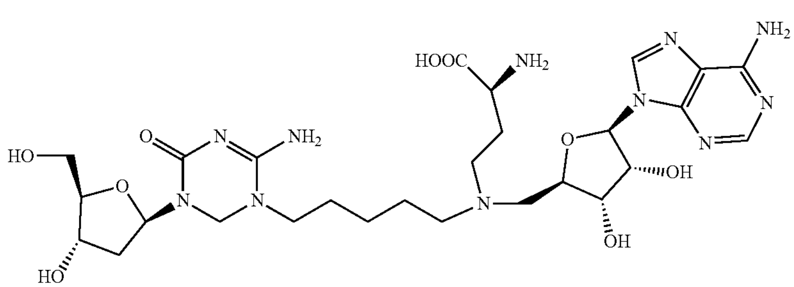 [SMILES: NC1=NC(=O)N([C@H]2C[C@H](O)[C@@H](CO)O2)CN1CCCCCN(CC[C@H](N)C(=O)O)C[C@H]1O[C@@H](n2cnc3c(N)ncnc32)[C@H](O)[C@@H]1O] | 6.0 ± 1.8 |

Although the invention has been described by way of example, it should be appreciated the variations or modifications may be made without departing from the scope of the invention. Furthermore, when known equivalents exist to specific features, such equivalents are incorporated as if specifically referred to in the specification.

The invention claimed is:

1. A compound of formula (I):

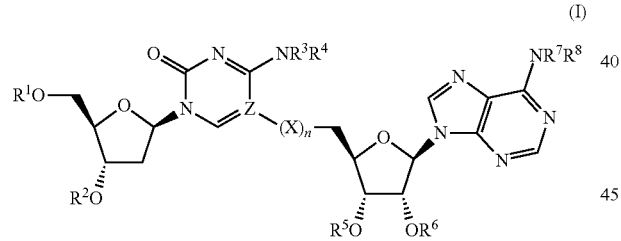

wherein:

each X is independently selected from (i) CH2, (ii) CHY, (iii) NH, and (iv) NY, or one X is S and another X is NY, and provided that no more than one X is CHY or NY, where Y is:

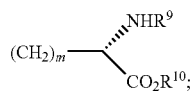

$R^1$ to $R^{10}$ are each independently selected from the group comprising H, $C_1$-$C_3$ alkyl, and $C_1$-$C_3$ acyl;

Z is C or N, where - - - represents a double bond when Z is C or a single bond when Z is N;

m is 2; and n is 2, 3, 4, 5 or 6.

2. A compound as claimed in claim 1, wherein Z is C.

3. A compound as claimed in claim 1, wherein Z is N.

4. A compound as claimed in claim 1, wherein at least one X is $CH_2$ or CHY.

5. A compound as claimed in claim 1, wherein at least one X is NH or NY.

6. A compound as claimed in claim 1, having the formula (II):

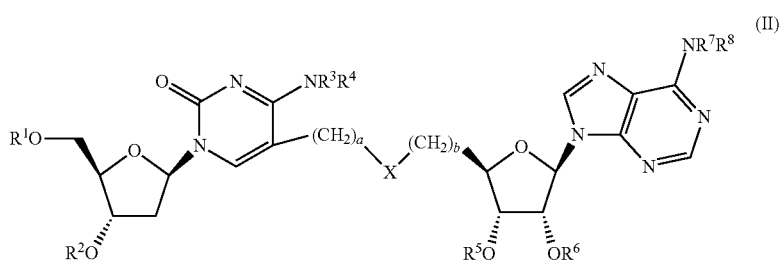

wherein:
X is NH or NY;
a and b are each 1, 2 or 3; and
Y and $R^1$ to $R^8$ are as defined in claim 1.

7. A compound as claimed in claim 6, wherein a and b are both 1.

8. A compound as claimed in claim 6, wherein X is NY.

9. A compound as claimed in claim 6, wherein a is 2 or 3 and b is 1.

10. A compound as claimed in claim 6, wherein a is 1 and b is 3.

11. A compound as claimed in claim 1, wherein one X is S and another X is NY, or one X is NH and another X is CHY.

12. A compound as claimed in claim 1, wherein one or more of $R^1$ to $R^8$ is H and the others are $C_1$-$C_3$ alkyl or $C_1$-$C_3$ acyl.

13. A compound as claimed in claim 1, wherein all of $R^1$ to $R^8$ is H.

14. A compound selected from the group consisting of:

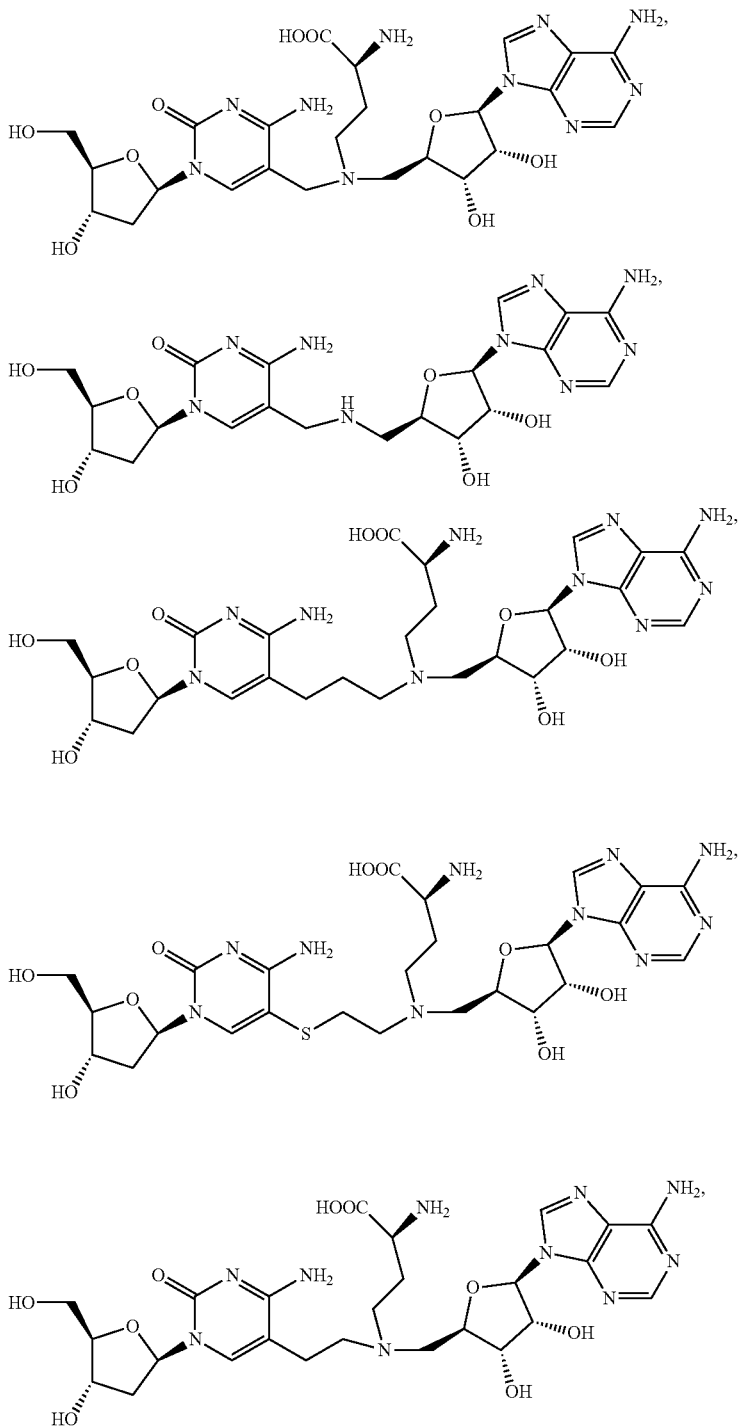

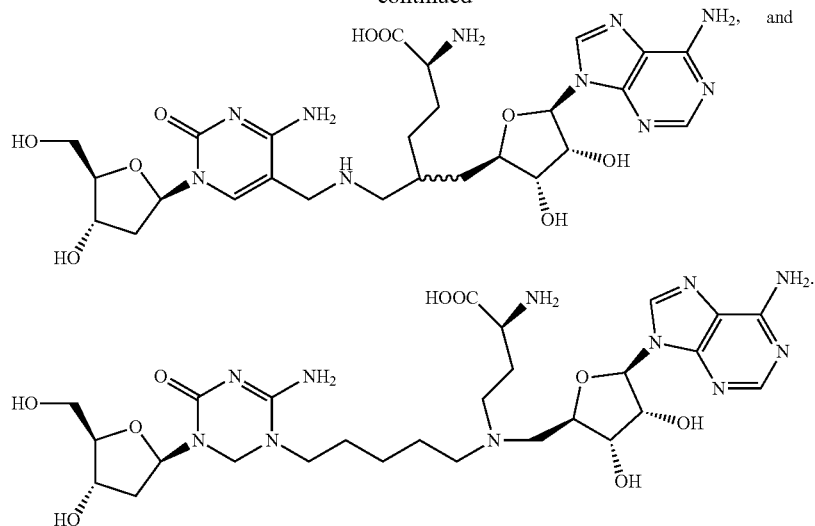

15. A pharmaceutical composition comprising a compound of claim 1 and a pharmaceutically acceptable carrier.

16. A method for inhibiting DNA methyltransferase 1 in a subject in need thereof, the method comprising administering to the subject, a therapeutically effective amount of a compound of formula (I):

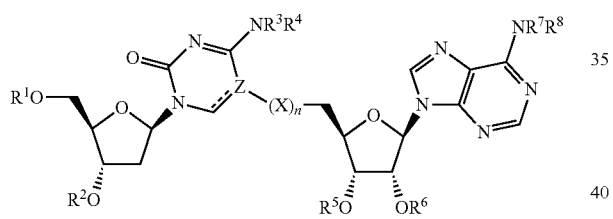

(I)

wherein:

each X is independently selected from (i) $CH_2$, (ii) CHY, (iii) NH, (iv) NY, and (v) S, and provided that no more than one X is CHY or NY, where Y is:

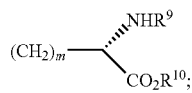

$R^1$ to $R^{10}$ are each independently selected from the group comprising H, $C_1$-$C_3$ alkyl, and $C_1$-$C_3$ acyl;

Z is C or N, where - - - represents a double bond when Z is C or a single bond when Z is N;

m is 2; and n is 2, 3, 4, 5 or 6.

* * * * *